(12) United States Patent
Szoka, Jr. et al.

(10) Patent No.: US 8,956,646 B2
(45) Date of Patent: Feb. 17, 2015

(54) ZWITTERIONIC LIPIDS

(75) Inventors: Francis C. Szoka, Jr., San Francisco, CA (US); Colin Walsh, Belmont, CA (US); Vincent Venditto, San Francisco, CA (US); Juliane Nguyen, San Francisco, CA (US); Emily Perttu, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/816,882

(22) PCT Filed: Aug. 15, 2011

(86) PCT No.: PCT/US2011/047780
§ 371 (c)(1),
(2), (4) Date: Apr. 26, 2013

(87) PCT Pub. No.: WO2012/024233
PCT Pub. Date: Feb. 23, 2012

(65) Prior Publication Data
US 2013/0216607 A1 Aug. 22, 2013

Related U.S. Application Data

(60) Provisional application No. 61/373,817, filed on Aug. 14, 2010.

(51) Int. Cl.
| C07C 229/00 | (2006.01) |
| C07C 229/12 | (2006.01) |
| A61K 9/127 | (2006.01) |
| C07C 279/14 | (2006.01) |
| C07C 309/14 | (2006.01) |
| C07F 9/09 | (2006.01) |
| C07F 9/54 | (2006.01) |
| C07F 9/6509 | (2006.01) |
| C07J 9/00 | (2006.01) |
| C40B 40/04 | (2006.01) |
| A61K 47/18 | (2006.01) |
| A61K 47/28 | (2006.01) |
| C07J 41/00 | (2006.01) |

(52) U.S. Cl.
CPC ............ *C07C 229/12* (2013.01); *A61K 9/1272* (2013.01); *C07C 279/14* (2013.01); *C07C 309/14* (2013.01); *C07F 9/091* (2013.01); *C07F 9/54* (2013.01); *C07F 9/650958* (2013.01); *C07J 9/00* (2013.01); *C40B 40/04* (2013.01); *A61K 47/186* (2013.01); *A61K 47/28* (2013.01); *C07J 41/0055* (2013.01)
USPC ........... 424/450; 424/400; 514/784; 552/544; 554/107

(58) Field of Classification Search
None
See application file for complete search history.

(56) References Cited

U.S. PATENT DOCUMENTS

| 4,053,585 | A | | 10/1977 | Allison et al. |
| 4,186,183 | A | | 1/1980 | Steck et al. |
| 4,235,871 | A | | 11/1980 | Papahadjopoulos et al. |
| 4,261,975 | A | | 4/1981 | Fullerton et al. |
| 4,485,054 | A | | 11/1984 | Mezei et al. |
| 4,501,728 | A | | 2/1985 | Geho et al. |
| 4,774,085 | A | | 9/1988 | Fidler |
| 4,824,603 | A | * | 4/1989 | Moller et al. ............... 510/122 |
| 4,837,028 | A | | 6/1989 | Allen |
| 4,946,787 | A | | 8/1990 | Eppstein et al. |
| 2004/0171572 | A1 | | 9/2004 | Wheeler |
| 2005/0239669 | A1 | * | 10/2005 | Krzysik et al. ............. 510/130 |
| 2007/0081963 | A1 | * | 4/2007 | Oh et al. .................... 424/70.14 |
| 2008/0145413 | A1 | * | 6/2008 | Panzner et al. ............. 424/450 |
| 2008/0306153 | A1 | * | 12/2008 | Panzner et al. ............. 514/558 |

FOREIGN PATENT DOCUMENTS

| WO | WO 91/17424 | 11/1991 |
| WO | WO 2012/024233 | 2/2012 |

OTHER PUBLICATIONS

K Sarmini, E Kenndler. "Ionization constants of weak acids and bases in organic solvents." Journal of Biochemical and Biophysical Methods, vol. 38, 1999, pp. 123-137.*
W Jiang. "Zwitterionic Separation Materials for Liquid Chromatography and Capillary Electrophoresis: Synthesis,Characterization and Application for Inorganic Ion and Biomolecule Separations." Thesis, Umea University (Sweden), 2003, pp. i-x and 1-53.*
L Nong, Z Zhong. "Synthesis and Properties Study of Phosphate Amphoteric Surfactants" Huaxue Yanjiu Yu Yingyong, vol. 15(3), 2003, pp. 435-436, in Chinese.*
CAS Registry Record for 857686-24-9. Entered STN Jul. 29, 2005, 2 printed pages.*
CAS Registry Record for 203796-71-8. Entered STN Apr. 8, 1998, 6 printed pages.*
W Reusch. "Virtual Textbook of Organic Chemistry." "Aromaticity". http://www2.chemistry.msu.edu/faculty/reusch/VirtTxtJml/react3.htm#rx8. Accessed from Web Apr. 24, 2014, 11 printed pages.*
Deamer et al., "Large Volume Liposomes by an Ether Vaporization Method", *Biochem. et Biophyis. Acta.*, 443: 629-634 (1976).

(Continued)

*Primary Examiner* — Frederick Krass
*Assistant Examiner* — Isaac Shomer
(74) *Attorney, Agent, or Firm* — Morgan, Lewis & Bockius LLP; Jeffry S. Mann

(57) ABSTRACT

In various embodiments, the present invention provides zwitterionic lipids, encapsulants incorporating these zwitterionic lipids and such encapsulants encapsulating one or more bioactive agent. An exemplary bioactive agent is a nucleic acid. Also provided are pharmaceutical formulations of the encapsulants and methods of using such formulations to deliver a bioactive agent to a subject in treating or diagnosing disease in that subject.

17 Claims, 35 Drawing Sheets

(56) References Cited

OTHER PUBLICATIONS

Fraley et al., "Entrapment of a bacterial plasmid in phospholipid vesicles: Potential for gene transfer", *Proc. Natl. Acad. Sci. U.S.A.*, 76(7): 3348-3352 (1979).

Hope et al., "Generation of Multiamellar and Unilamellar Phospholipid Vesicles", *Chemistry and Physics of Lipids*, 40: 89-107 (1986).

Huang et al., "Thiocholesterol-Based Lipids for Ordered Assembly of Bioresponsive Gene Carriers", *Molecular Therapy*, 11(3): 409-417 (2005).

Mayer et al., "Vesicles of variable sizes produced by a rapid extrusion procedure", *Biochem. et Biophyis. Acta.*, 858: 161-168 (1986).

Obata et al., "Evaluation of pH-responsive liposomes containing amino acid-based zwitterionic lipids for improving intracellular drug deliverty in vitro and in vivo", *Journal of Controlled Release*, 142: 267-276 (2010).

Szoka, Jr. et al., "Procedure for preparation of liposomes with large internal aqueous space and high capture by reverse-phase evaporation", Proc. Natl. Acad. Sci. U.S.A., 75(8): 4194-4198 (1978).

Szoka, Jr., F., "Comparative Properties and Methods of Preparation of Lipid Vesicles (Liposomes)", *Ann. Rev. Biopys. Bioeng.*, 9: 467-508 (1980).

Williams et al., "Low density lipoprotein receptor-independent hepatic uptake of a synthetic, cholesterol-scavenging lipoprotein: Implications for the treatment of receptor-deficient atherosclerosis", *Proc. Natl., Acad. Sci., U.S.A.*, 85: 242-246 (1988).

Jones et al., "Acylcarnitines: Role in brain", *Progress in Lipid Research*, vol. 49, pp. 61-75 (2010).

\* cited by examiner

FIGURE 29

| | encapsulation efficiency | size | zeta potential |
|---|---|---|---|
| DOBA-Q/DOPE/DMG-PEG (60/30/10) | 74% | 56.3 nm PDI 0.198 | -6.3 mV |
| CarChems/DOPE/DMG-PEG (60/30/10) | 75% | 88.5 nm PDI 0.263 | -3.9 mV |
| DOMPA-Q/DOPE/DMG-PEG (60/30/10) | 65% | 80.9 nm PDI 0.298 | -9.5 mV |
| DOPA-Q/DOPE/DMG-PEG (60/30/10) | 80% | 67.8 nm PDI 0.212 | -17 mV |

FIGURE 30

| | encapsulation efficiency | size | zeta potential |
|---|---|---|---|
| DOBA-Q/DOPE/DMG-PEG (60/30/10) | 74% | 56.3 nm PDI 0.198 | - 6.3 mV |
| DOBA-Q/DlinPE/DMG-PEG (60/30/10) | 53% | 80.5 nm PDI 0.212 | - 7.9 mV |
| DOBA-Q/Chol/DMG-PEG (60/30/10) | 91% | 82.7 nm PDI 0.301 | - 6.5 mV |
| DOBA-Q/C6Chems/DMG-PEG (60/30/10) | 88% | 78.5 nm PDI 0.242 | - 3.9 mV |
| CarChems/DOPE/DMG-PEG (60/30/10) | 75% | 88.5 nm PDI 0.263 | - 3.9 mV |
| CarChems/DOPE/DGDG (60/30/10) | 86% | 129.9 nm PDI 0.201 | - 4.7 mV |
| CarChems/DOPC/DMG-PEG/DGDG (60/30/10) | 79% | 89.2 nm PDI 0.192 | - 8.0 mV |

FIGURE 31
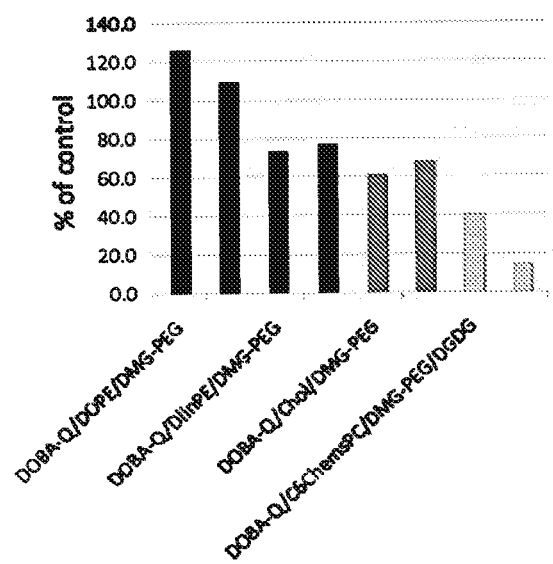
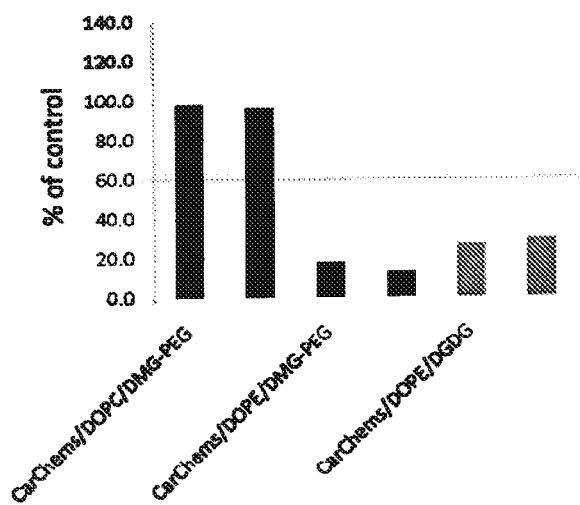

ZWITTERIONIC LIPIDS

CROSS-REFERENCE TO RELATED APPLICATIONS

This application claims the benefit of U.S. Application 61/373,817, filed Aug. 14, 2010, which is incorporated by reference.

STATEMENT AS TO RIGHTS TO INVENTIONS MADE UNDER FEDERALLY SPONSORED RESEARCH OR DEVELOPMENT

This invention was made with Government support under Grant Nos. R01 GM061851 and R01 EB003008, awarded by the National Institutes of Health. The Government has certain rights in the invention.

FIELD OF THE INVENTION

The present invention relates to zwitterionic lipids and particles and delivery agents including zwitterionic lipids that are useful for delivering various molecules to cells.

BACKGROUND OF THE INVENTION

Liposomes are small vesicles composed of amphipathic lipids arranged in spherical bilayers. Liposomes are usually classified as small unilamellar vesicles (SUV), large unilamellar vesicles (LUV), or multi-lamellar vesicles (MLV). SUVs and LUVs, by definition, have only one bilayer, whereas MLVs contain many concentric bilayers. Liposomes may be used to encapsulate various materials, by trapping hydrophilic compounds in the aqueous interior or between bilayers, or by trapping hydrophobic compounds within the bilayer.

Liposomes exhibit a wide variety of characteristics, depending upon their size, composition, and charge. For example, liposomes having a small percentage of unsaturated lipids tend to be slightly more permeable, while liposomes incorporating cholesterol or other sterols tend to be more rigid and less permeable. Liposomes may be positive, negative, or neutral in charge, depending on the hydrophilic group. For example, choline-based lipids impart a positive charge, phosphate and sulfate based lipids contribute a negative charge, and glycerol-based lipids and sterols are generally neutral in solution.

Liposomes have been employed to deliver biologically active material. See for example Allison, U.S. Pat. No. 4,053,585, which disclosed the administration of several antigens in negatively-charged liposomes, optionally including killed *M. tuberculosis*. Fullerton et al., U.S. Pat. No. 4,261,975, disclosed the use of separated influenza membranes, with hemagglutinin spikes attached, which is bound to liposomes for use in influenza vaccines.

Lipids having headgroups that are environmentally sensitive are desirable because the net charge of these molecules can be cationic, neutral, or anionic as dictated by the pH of the surrounding environment. Of particular interest are lipids with headgroups that are transiently cationic. Lipids with transiently cationic headgroups can convert into a non-lamellar phase upon a change in pH, and will deliver their contents into the cytoplasm. Cytoplasmic DNA delivery will enable high gene transfer. Transiently cationic lipids should also facilitate encapsulation of negatively charged nucleic acids, and promote the delivery of nucleic acids to the cytosol while maintaining low cytotoxicity and reduced immunoreactivity in vivo.

In addition to this transient cationic behavior, lipids that disperse in aqueous solution and form small (30-300 nm) bilayer structures are of interest as these lipids should be able to encapsulate small molecules as well as nucleic acids either by themselves or as a component in a liposomal formulation.

Lipid vesicles (liposomes) can be formed by a variety of techniques that, in general, start with "dry" lipids that are introduced into an aqueous phase (D. Lasic, *J. Theor. Biol.* (1987) 124:35-41). Once the lipid is hydrated, liposomes form spontaneously. Techniques have been developed to control the number of lamellae in the liposomes and to produce a defined particle size. The available procedures are satisfactory for most applications where small amounts of material are needed (G. Gregoriadis, "Liposome Technology" I-III (Boca Raton, Fla., CRC Press, Inc.), 1984). However, for the manufacture of vesicles on a large scale, the lipid hydration step can be a severe constraint on vesicle production. Furthermore, a method of synthesizing a liposome incorporating a zwitterionic lipid that allows for the reliable engineering of parameters such as liposome diameter, and amount of encapsulated bioactive substance encapsulated would represent an advance in the art. Accordingly, new methods for forming lipid vesicles are desirable.

Thus, there is a need in the art for lipids that are transiently cationic and methods of making encapsulents from these lipids. The present invention answers these and other needs.

SUMMARY OF THE INVENTION

In various embodiments, the invention provides novel, transiently cationic zwitterionic lipids that are particle forming delivery agents useful for delivering bioactive agents to cells. The invention also provides compositions, and methods of use for the study, diagnosis, and treatment of traits, diseases and conditions that respond to a bioactive agent, e.g., the modulation of gene expression and/or activity in a subject or organism. In various embodiments, the invention relates to novel zwitterionic lipids, and microparticles, nanoparticles and transfection agents that effectively transfect or deliver bioactive agents, such as, to relevant cells and/or tissues, such as in a subject or organism. Such novel cationic lipids, microparticles, nanoparticles and transfection agents are useful, for example, in compositions for preventing, inhibiting, or treating diseases, conditions, or traits in a cell, tissue, subject or organism.

In various embodiments, the present invention provides a family of zwitterionic lipids, particles containing these lipids and methods of using these particles in therapeutic, diagnostic and investigational applications. Exemplary zwitterionic lipids of the invention include a quaternary ammonium moiety and a carboxylic acid moiety. In various embodiments, the lipid includes one or more hydrophobic chains covalently bound to carnitine, or an analogue thereof. In various embodiments, the invention provides zwitterionic lipids based on a betaine headgroup (FIG. 16). Exemplary zwitterionic lipids of the invention include a hydrophobic chain bound to carnitine, or an analogue thereof, via derivatization of the carnitine hydroxyl group. In various embodiments, the zwitterionic lipids of the invention are based upon a betaine structure bearing one or more hydrophobic chains. In exemplary embodiments, the lipids include a guanidino group. In various embodiments the zwitterlipids contain two groups that can provide a positive charge.

In various embodiments, the invention provides lipids based upon carnitine or betaine that are zwitterionic at neutral pH but become cationic when the carboxylate is protonated at an acidic pH, such as the pH of the endosome. In various embodiments, the invention provides zwitterlipid-based particles loaded with a bioactive agent that can deliver their contents into the cytoplasm. Cytoplasmic DNA delivery enables high gene transfer. Cytoplasmic RNAi delivery enables mRNA knockdown. See, for example, FIGS. 17-31.

The zwitterlipids have two other advantages over currently used lipids: 1) they provide a unique platform for assembly of a nucleic acid (e.g., DNA) carrier; 2) they eliminate the immune stimulatory toxicity associated with traditional cationic lipids.

In exemplary embodiments, the invention provides a zwitterionic lipid according to Formula I:

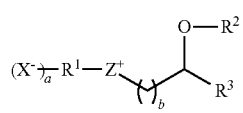

wherein $X^-$ is a fixed or a titratable anionic moiety. Exemplary anionic moieties include,

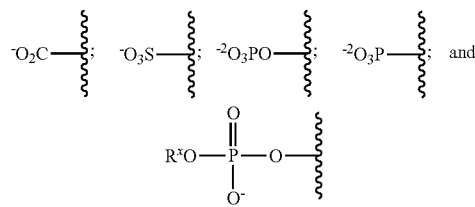

wherein $R^x$ is selected from H and substituted or unsubstituted alkyl.

In Formula I, the index a is selected from the integers 1, 2, 3, 4, 5, 6, or higher. The index b is selected from the integers 0, 1, 2, 3, 4, 5, 6, 7, 8, 9, 10, 11, 12, 13, 14, 15, 16, 17, 18 or higher. The symbol $R^1$ represents a linker moiety. Exemplary linker moieties include substituted or unsubstituted alkyl, substituted or unsubstituted heteroalkyl, substituted or unsubstituted aryl, and substituted or unsubstituted heteroaryl. The symbol $Z^+$ represents a fixed or titratable cation. Exemplary cations include:

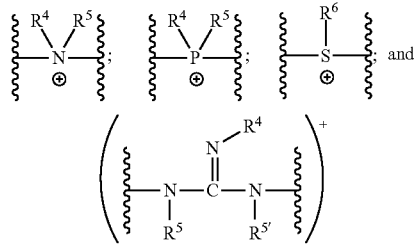

In exemplary embodiments, $R^4$, $R^5$ and $R^{5'}$ are independently H, substituted or unsubstituted alkyl, substituted or unsubstituted heteroalkyl; substituted or unsubstituted aryl or substituted or unsubstituted heteroaryl. In various embodiments, $R^6$ is selected from substituted or unsubstituted alkyl, substituted or unsubstituted heteroalkyl; substituted or unsubstituted aryl or substituted or unsubstituted heteroaryl.

$R^2$ and $R^3$ are members independently selected from H, substituted or unsubstituted alkyl, substituted or unsubstituted heteroalkyl; substituted or unsubstituted aryl and substituted or unsubstituted heteroaryl. In exemplary embodiments, at least one of $R^2$ and $R^3$ is other than H. In exemplary embodiments, both $R^2$ and $R^3$ are other than H.

In various embodiments, the zwitterionic lipid of the invention includes $R^2$ and $R^3$ groups which are independently selected from unbranched and branched alkyl groups, each of which is optionally substituted with one or more "alkyl group substituent" as that term is defined herein. In various embodiments, one of $R^2$ and $R^3$ is unbranched and the other member is branched. Representative zwitterionic lipids of the invention include an $R^2$ and/or $R^3$ group comprising a subunit which is terminated with a reactive functional group. In various embodiments, the subunit is a member selected from a $C_6$-$C_{12}$ fluorocarbyl and a $C_6$-$C_{12}$ hydrocarbyl moiety; in exemplary lipids, this subunit is a component of an unbranched chain.

In various embodiments, the invention provides a zwitterionic lipid according to Formula VII:

wherein $X^-$ is a member selected from:

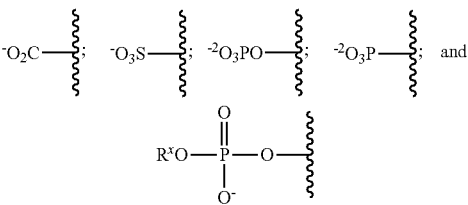

wherein $R^x$ is selected from H and substituted or unsubstituted alkyl.

The index a is selected from the integers 1, 2, 3, 4, 5, 6 or higher. The symbol $R^1$ is a member selected from substituted or unsubstituted alkyl, substituted or unsubstituted heteroalkyl, substituted or unsubstituted aryl, and substituted or unsubstituted heteroaryl. The cation $Y^+$ is selected from:

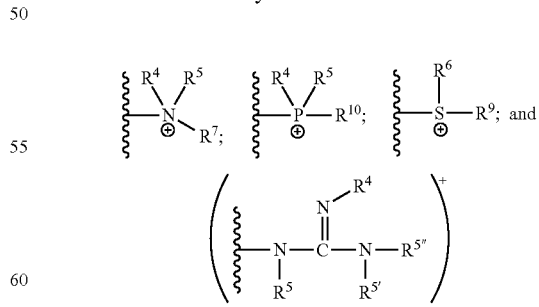

in which $R^4$, $R^5$, $R^{5'}$, $R^{5''}$ and $R^7$ are independently H, substituted or unsubstituted alkyl, substituted or unsubstituted heteroalkyl; substituted or unsubstituted aryl and substituted or unsubstituted heteroaryl. $R^8$, $R^9$ and $R^{10}$ are members independently selected from substituted or unsubstituted alkyl, substituted or unsubstituted heteroalkyl; substituted or unsubstituted aryl or substituted or unsubstituted heteroaryl. $R^2$ is as discussed in the context of Formula I.

In a further embodiment, the invention provides an encapsulant incorporating a zwitterionic lipid of the invention and such an encapsulant incorporating a bioactive agent encapsulated therein. Also provided are pharmaceutical formulations including a zwitterionic lipid of the invention, and such formulations incorporating an encapsulant with an entrapped bioactive agent. Methods of using the lipids and encapsulants in diagnosis and therapy are also provided.

Additional embodiments, objects and advantages are apparent from the detailed description that follows.

BRIEF DESCRIPTION OF THE DRAWINGS

FIG. 29 is a table showing ZNLP encapsulating siRNA: hydrodynamic diameter and zeta potential: siRNA was encapsulated into ZNLP from various zwitterionic lipids.

Formulations showed neutral/negative zeta potential at pH 7.4. ZNLP displayed small sizes with relatively high siRNA encapsulation efficiency.

FIG. 30 is a table showing the effect of helper lipids on size and encapsulation efficiency: Changing helper lipid and lipid composition affects size and encapsulation efficiency of ZNLP. DOBA-Q formed small lipid vesicles≤80 nm. DIinPE decreases encapsulation efficiency of siRNA in DOBA-Q formulation most likely due to less dense packing. CarChems/DOPE/DGDG shows larger sizes due to the lack of PEG-shielding. All lipid formulations display negative/neutral zeta potential.

FIG. 31 shows the results of a knockdown experiment in mice, the effect of various ZNLP formulations on ApoB knockdown in mouse liver: Mice were injected with 5 mg/kg of ApoB siRNA. After 48 h ApoB mRNA level was quantified in liver using a branched DNA assay. Control animals were injected with Tris buffered glucose.

Figure 32:
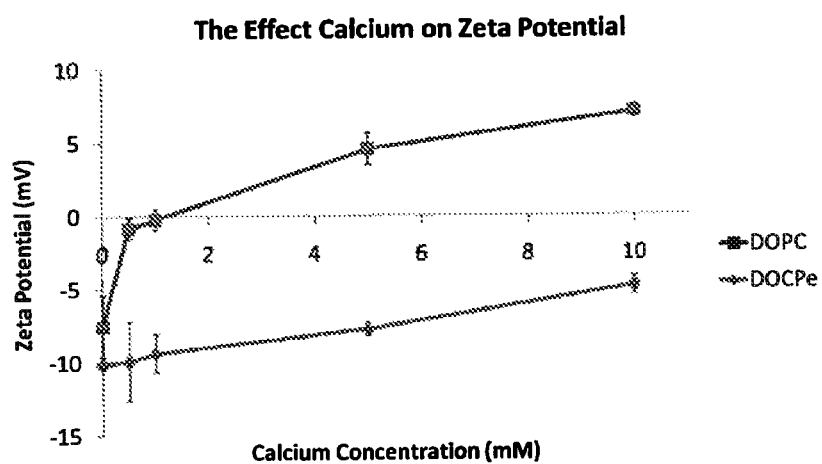

FIG. 32 shows the effect of calcium on zeta potential for DOPC and DOCPe.

Figure 33:
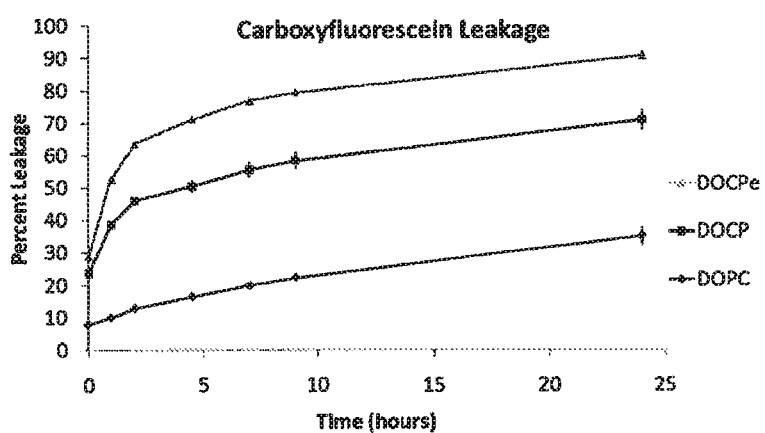

FIG. 33 shows carboxyfluorescein leakage as a function of time for DOCPe, DOCP and DOPC.

Figure 34:
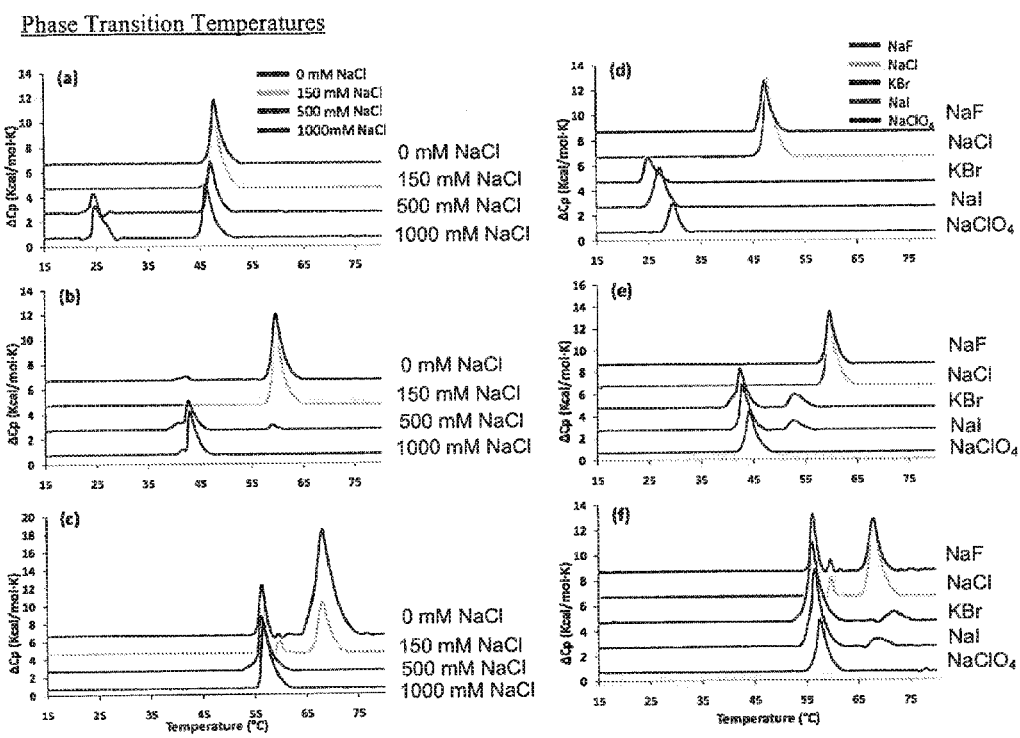

FIG. 34 shows DSC traces of phase transition temperatures for DMSB, DPSB, and DSSB (a-c) at four NaCl concentrations (a) DMSB, (b) DPSB, (c) DSSB and (d-f) with 150 mM NaF, NaCl, KBr, NaI, and $NaClO_4$ (d) DMSB, (e) DPSB (f) DSSB. All buffers contain 10 mM HEPES, pH 7.4. Preparations were made at 26 mM SB lipid by thin film rehydration at 80° C., followed by brief 20 second bursts of sonication at 80° C. (~2-4 times) to make dispersions of large bilayer fragments.

Figure 35:
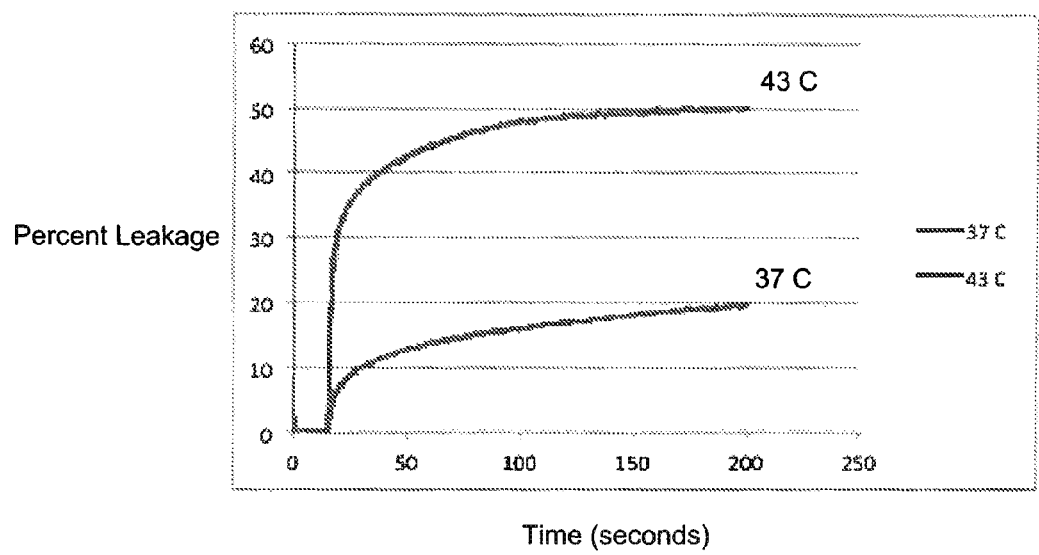

FIG. 35 shows leakage kinetics at two different temperatures.

DETAILED DESCRIPTION OF THE EMBODIMENTS

I. Abbreviations

Abbreviations used herein generally have standard, accepted meanings within the lipid and synthetic organic chemistry arts. "FGZA" refers to First Generation Assymmetric Bolaamphiphiles." "SGZA" refers to Second Generation Assymetric Bolaamphiphiles.

II. Introduction

In various embodiments, the present invention provides lipids with zwitterionic betaine head groups, which contain a cationic or protonatable moiety, e.g., an amine, and an anion, e.g., a carboxylate or phosphate. Lipids of the invention may also include additional cationic and/or anionic moieties, which can be fixed or titratable. Exemplary lipids of the invention become cationic upon protonation of the anion. The net charge of these molecules can therefore be cationic, neutral, or anionic, and is dictated by the pH of the surrounding environment. The pKa of the lipid, defined as the pH at which the net charge of the lipid changes, is engineerable according to the principles set forth herein and, generally, depends upon the nature of the cation(s) and anion(s) in the structure and the composition of the linker region between the charged groups. The transient cationic nature of exemplary lipids of the invention facilitates the encapsulation of bioactive agents, such as negatively charged nucleic acids or proteins with the appropriate pI. The zwitterionic lipids of the invention promote the delivery of nucleic acids to the cytosol while maintaining low cytotoxicity and reduced immunoreactivity in vivo.

III. Definitions

Where substituent groups are specified by their conventional chemical formulae, written from left to right, they optionally equally encompass the chemically identical substituents, which would result from writing the structure from right to left, e.g., —$CH_2O$— is intended to also recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. In some embodiments, each of the above terms (e.g., "alkyl," "heteroalkyl," "aryl" and "heteroaryl") refers to unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR', —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si) and boron (B).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "Linker" or "L", as used herein, refers to a single covalent bond or a series of stable covalent bonds incorporating 1-30 nonhydrogen atoms selected from the group consisting of C, N, O, S and P that covalently attach the components of the zwitterionic head group and/or the headgroup to the hydrophobic chains of the lipids.

Exemplary linkers include a moiety that includes —C(O) NR—, —C(O)O—, —NR—, —S—, —O—, and the like.

Exemplary linkers are cleavable linkers. A "cleavable linker" is a linker that has one or more cleavable groups that may be broken by the result of a reaction or condition. The term "cleavable group" refers to a moiety that allows for release of a portion of the lipid from the remainder of the lipid or a conjugation partner of the lipid from the lipid. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available.

In an exemplary embodiment, cleavage of the cleavable linker results in separation of a cationic group (e.g., Z$^+$ and/or Z$^{a+}$) or an anionic group (X$^-$) or a hydrophobic chain from the remainder of the lipid. In various embodiments, this results in a more biologically tolerable lipid. In various embodiments, the cationic or anionic group is associated (e.g., by ionic bonding) with a bioactive agent, which is released from the remainder of the lipid by the cleavage. An exemplary cleavable group, an ester, is cleavable group that may be cleaved by hydrolysis in acidic or basic milieu, resulting in a carboxylate-containing fragment and a hydroxyl-containing product. Other exemplary cleavable groups are ketal, acetal, hydrazone and vinylether groups. Exemplary cleavable groups in the compounds of the invention are cleavable in acidic milieu, preferably mildly acid milieu, e.g., at a pH of about 5 to about 7, e.g., from about 6 to about 7.

The linker can be used to attach the compound to another component of a conjugate, such as a targeting moiety (e.g., antibody, ligand, non-covalent protein-binding group, etc.), an analyte, a biomolecule, a drug and the like.

The term "lipid" refers to any compound having a balance of hydrophobic and hydrophilic groups, which is capable of forming a bilayer such that a hydrophobic portion of the lipid material orients toward the bilayer while a hydrophilic portion orients toward the aqueous phase. Hydrophilic characteristics derive from the presence of hydroxyl, phosphato, phosphono, carboxylic, sulfato, amino, sulfhydryl, guanadino, and other like groups. Hydrophobicity is conferred by the inclusion of groups that include, but are not limited to, long chain saturated and unsaturated aliphatic hydrocarbon groups, aliphatic fluorocarbon groups and such groups substituted by one or more aromatic, cycloaliphatic or heterocyclic group(s).

The term "zwitterionic lipid," as used herein, refers to a lipid comprised of a zwitterionic head group and one or more hydrophobic chains linked through one or more covalent bonds.

"Zwitterionic head group," as used herein, refers to a multifunctional group, which at a given pH with the range of 2-10 is zwitterionic and at some other lower pH within the same range is cationic. The cationic and negative charges are either permanent or pH dependent. The cationic nature may arise from any number of primary, secondary, tertiary or quaternary amines, guanadines or non-nitrogenous cations, e.g., phosphonium, sulfonium, etc. The anionic portion can consist of any number of sulfonates, phosphates, phosphonates or carboxylates.

"Hydrophobic chain," as used herein, refers to a hydrophobic group or hydrocarbon chain comprised of alkyl, heteroalkyl, aryl, or heteroaryl moieties in any combination. Exemplary alkyl groups are a hydrocarbon or fluorocarbon group having from 6 to 24 carbon atoms, containing any number of branch points, cyclic structures or points of unsaturation alone such as the cis-9-octadecene (oleoyl) or cis,cis-9,12-octadecadiene (linoleyl) or in combination such as the oleyl and linoleyl. A hydrophobic group also includes the fused ring system of cholesterol and other sterols "Linker regions," as used herein, refers to moieties connecting the zwitterionic head group to one or more hydrophobic chains. The linker regions generally include a "linkage fragment," which is formed between a reactive functional group on a zwitterionic head group precursor and a hydrophobic chain precursor, which results in the formation of a covalent bond between the head group and the hydrophobic chain (the "linkage fragment").

"Titratable group," as used herein refers to a group that can be protonated or deprotonated at a pH from about 3 to about 10, preferably from about 5 to about 8, more preferably from about 5.5-7. An exemplary titratable group is a primary, secondary or tertiary amine. In contrast, a "fixed group" is essentially permanently charged under biologically relevant conditions (e.g., isotonic salt, pH 7.4). An exemplary fixed cation is a tetraalkyl quaternary ammonium cation.

The term "neutral" refers to any of a number of lipid species which exist in an uncharged form. Such lipids include, for example diacylglyceride, tocopherol and cholesterol.

The term "non-cationic lipid" refers to any neutral lipid as described above as well as anionic lipids. Examples of anionic lipids include cardiolipin, diacylphosphatidylglycerol, diacylphosphatidylserine and diacylphosphatidic acid.

The term "cationic lipid" refers to any of a number of lipid species which carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the present invention. These include, for example, LIPOFECTIN™ (commercially available cationic liposomes comprising DOTMA and DOPE, from GIBCO/BRL, Grand Island, N.Y., USA); LIPOFECTAMINE™; (commercially available cationic liposomes comprising DOSPA and DOPE, from GIBCO/BRL); and TRANSFECTAM™. (commercially available cationic lipids comprising DOGS from Promega Corp., Madison, Wis., USA).

As used herein, "nucleic acid" means any natural or non-natural nucleoside, or nucleotide and oligomers and polymers thereof, e.g., DNA, RNA, single-stranded, double-stranded, triple-stranded or more highly aggregated hybridization motifs, and any chemical modifications thereof. Modifications include, but are not limited to, conjugation with a compound or a construct that includes a linker that tethers the compound to the nucleic acid, and those providing the nucleic acid with a group that incorporates additional charge, polarizability, hydrogen bonding, electrostatic interaction, fluxionality or functionality to the nucleic acid. Exemplary modifications include the attachment of one or more conjugation partner to the nucleic acid, at any position. Exemplary conjugation partners include hydrophobic or hydrophilic moieties, minor groove binders, intercalating agents, quenchers, chelating agents, metal chelates, amino acids, peptides, solid supports, and other groups that are usefully attached to nucleic acids. Exemplary nucleic acids of the invention include one or more dye moiety of the invention bound thereto.

Unless otherwise specified, the term nucleic acid is used interchangeably with gene, DNA, cDNA, RNA, mRNA, oligonucleotides both single and double stranded and RNAi also known as short interfering RNA, shRNA. The term specifically encompasses ribozymes; nucleic acid cloning and/or expression vectors such as plasmids; genetically engineered viral genomes, expression cassettes, and chromosomes from mammalian (especially human) sources. The nucleic acid can comprise DNA, RNA or chimeric mixtures or derivatives or modified versions thereof.

Exemplary modified nucleic acids include, but are not limited to, peptide nucleic acids (PNAs), those with phosphodiester group modifications (e.g., replacement of O⁻ with OR, NR, or SR), 2'-, 3'- and 5'-position sugar modifications, modifications to the base moiety, e.g., 5-position pyrimidine modifications, 8-position purine modifications, modifications at exocyclic amines, substitution of 4-thiouridine, substitution of 5-bromo or 5-iodo-uracil; backbone modifications, i.e., substitution of $P(O)O_3$ with another moiety, methylations, unusual base-pairing combinations such as the isobases, isocytidine and isoguanidine and the like. Nucleic acids can also include non-natural bases, e.g., nitroindole. Non-natural bases include bases that are modified with a conjugation partner. Modifications within the scope of "nucleic acid" also include 3' and 5' modifications with one or more conjugation partner.

In addition to the naturally occurring "nucleobases," adenine, cytosine, guanine and thymine, nucleic acids optionally include bases modified at the sugar or the pyrimidine or purine moiety attached to the sugar. For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine. In another embodiment, the nucleic acid comprises at least one modified sugar moiety including, but not limited to, arabinose, 2-fluoroarabinose, xylulose, and hexose.

In yet another embodiment, the nucleic acid comprises at least one modified phosphate backbone including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof.

Furthermore, "nucleic acid" includes those species in which one or more internucleotide bridge does not include phosphorus: the bridge being optionally modified with a compound of the invention or a linker arm-cyanine dye construct. An exemplary bridge includes a substituted or unsubstituted alkyl or substituted or unsubstituted heteroalkyl moiety in which a carbon atom is the locus for the interconnection of two nucleoside sugar residues (or linker moieties attached thereto) and a compound of the invention or a linker construct that includes a compound of the invention. The discussion above is not limited to moieties that include a carbon atom as the point of attachment; the locus can also be another appropriate linking atom, such as nitrogen or another atom.

The term "therapeutically effective amount," as used herein, means that amount of a bioactive agent encapsulated in a particle comprising a zwitterionic lipid of the present invention which is effective for producing some desired therapeutic effect in at least a sub-population of cells in an animal and thereby treating or preventing a disease treatable or preventable by the bioactive agent at a reasonable benefit/risk ratio applicable to any medical treatment.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al, *Journal of Pharmaceutical Science*, 66: 1-19 (1977)). Certain specific compounds of the present invention contain both basic and acidic functionalities that allow the compounds to be converted into either base or acid addition salts.

"Low boiling point organic solvent," refers to an organic solvent with a boiling point less than or equal to about 100° C.

A "hydrophilic polymer" as used herein refers to long chain highly hydrated flexible neutral polymers attached to lipid molecules. Examples include, but are not limited to polyethylene glycol (PEG), polyethylene glycol derivatized with phosphatidyl ethanolamine (PEG-PE), polyethylene glycol derivatized with a steroid (e.g., cholesterol), and polyethylene glycol derivatized with distearoyl-sn-glycero-3-phosphatidylethanolamine (PEG-DSPE). Other polymers include: hydroxypropylmethacrylamide, polyoxazolines and polyvinylpyrrolidone. Such polymers typically have a molecular weight in the range of 1000-10,000. Preferably, the molecular weight for PEG is approximately 2000.

"Transfection" refers to contacting a living cell with a nucleic acid, for example, as part of a lipid:nucleic acid complex.

"Transfection activity" refers to the efficiency of introducing a nucleic acid into a living cell. Transfection efficiency may be measured by determining the amount of expression of a reporter gene that has been transfected into the cell as an encapsulated component of a particle of the invention, for example, by fluorescent or functional assays.

"Bioactive agents" include, for example, antibodies (e.g., monoclonal, chimeric, humanized etc.), cholesterol, hormones, antivirals, peptides, proteins, chemotherapeutics, small molecules, vitamins, co-factors, nucleic acids (e.g., nucleosides, nucleotides, oligonucleotides, enzymatic nucleic acids, antisense nucleic acids, triplex forming oligonucleotides, 2,5-A chimeras, allozymes, aptamers, decoys and analogs thereof, and small nucleic acid molecules, such as short interfering nucleic acid (siNA), short interfering RNA (siRNA), double-stranded RNA (dsRNA), micro-RNA (miRNA), and short hairpin RNA (shRNA) molecules). Thus, the bioactive agent may be any of a variety of different agents, which may be adapted for a variety of different uses including, but not limited to pharmaceutical, nutriceutical, cosmeceutical, and diagnostic applications. Exemplary agents include, but are not limited to, anti-cancer chemotherapeutics (e.g., doxorubicin, danorubicin, camptothecin, cisplatin, gemcitabine and the like), antibiotics (e.g., antibacterials, antifungals such as amphotericin B, antivirals, anti-parasitic agents, and the like), analgesics, anesthetics, anti-acne agents, biomolecules (e.g., nucleic acids (e.g., RNA, DNA, siRNA, and the like), polypeptides (e.g., peptides, including recombinant polypeptides and peptides, including naturally or chemically modified polypeptides and peptides (e.g., PEGylated polypeptides)), antibodies and the like), antigenic substances (e.g., which may be a component of a vaccine), and the like. In some embodiments, a bioactive agent is a drug. A drug is commonly understood in the art to be a substance used in the diagnosis, treatment, or prevention of a disease or as a component of a medication, and includes, but is not limited to, substances recognized or defined as such by the U.S. Food and Drug Administration. Example of drugs in addition to those described herein include, for example, those described in US Patent Application Publication 20110028460 A1. In some embodiments, a bioactive agent is an anti-cancer chemotherapeutic. Accordingly, a wide variety of bioactive agents may be encapsulated and delivered to a subject through the compounds, compositions and methods of the invention, such as, for example, the inverse zwitterlipids and the sulfobetaine zwitterlipids described in the Examples.

IV. The Embodiments

Lipids

In the discussion that follows, titratable anions and cations are generally shown in their ionized form. It will be readily apparent to those of skill in the art that Applicants are also disclosing species in which which either or both the anionic or cationic group is in its non-ionized form.

In exemplary embodiments, the invention provides a zwitterionic lipid according to Formula I:

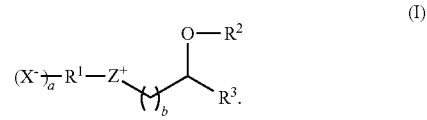

wherein $X^-$ is a fixed or a titratable anionic moiety. Exemplary anionic moieties include,

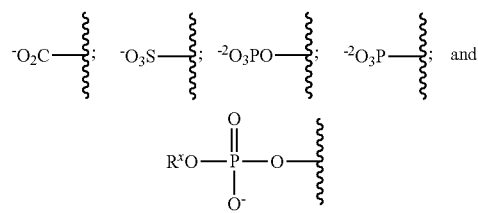

wherein $R^x$ is selected from H and substituted or unsubstituted alkyl. In some embodiments, $R^x$ is selected from $C_1$, $C_2$, $C_3$, $C_4$, $C_5$ and $C_6$ alkyl.

In Formula I, the index a is selected from the integers 1, 2, 3, 4, 5, 6, or higher. The index b is selected from the integers 0, 1, 2, 3, 4, 5, 6, 7, 8, 9, 10, 11, 12, 13, 14, 15, 16, 17, 18 or higher. The symbol $R^1$ represents a linker moiety. Exemplary linker moieties include substituted or unsubstituted alkyl, substituted or unsubstituted heteroalkyl, substituted or unsubstituted aryl, and substituted or unsubstituted heteroaryl. The symbol $Z^+$ represents a fixed or titratable cation. Exemplary cations include:

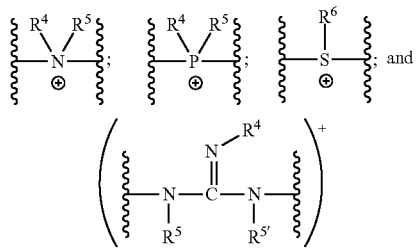

In exemplary embodiments, $R^4$, $R^5$ and $R^{5'}$ are independently H, substituted or unsubstituted alkyl, substituted or unsubstituted heteroalkyl; substituted or unsubstituted aryl or substituted or unsubstituted heteroaryl. In various embodiments, $R^6$ is selected from substituted or unsubstituted alkyl, substituted or unsubstituted heteroalkyl; substituted or unsubstituted aryl or substituted or unsubstituted heteroaryl.

$R^2$ and $R^3$ are members independently selected from H, substituted or unsubstituted alkyl, substituted or unsubstituted heteroalkyl; substituted or unsubstituted aryl and substituted or unsubstituted heteroaryl. In exemplary embodiments, at least one of $R^2$ and $R^3$ is other than H. In exemplary embodiments, both $R^2$ and $R^3$ are other than H.

In various embodiments, the zwitterionic lipid of the invention includes $R^2$ and $R^3$ groups which are independently selected from unbranched and branched alkyl groups, each of which is optionally substituted with one or more "alkyl group substituent" as that term is defined herein. In various embodiments, one of $R^2$ and $R^3$ is unbranched and the other member is branched. Representative zwitterionic lipids of the invention include an $R^2$ and/or $R^3$ group comprising a subunit which is terminated with a reactive functional group. In various embodiments, the subunit is a member selected from a $C_6$-$C_{12}$ fluorocarbyl and a $C_6$-$C_{12}$ hydrocarbyl moiety; in exemplary lipids, this subunit is a component of an unbranched chain.

When a component of the zwitterionic lipids of the invention includes a reactive functional group, these groups are preferably those discussed herein under the heading "Reactive Functional Groups." Exemplary reactive functional groups of use in compounds of the invention include hydroxyl, amine, carboxylic acid, aldehyde, carboxylic acid ester, and thiol.

With respect to the structure according to Formula I, the groups $R^2$ and $R^3$ are optionally substituted with one or more fixed or titratable anion and/or cation. In an exemplary embodiment, one or both of $R^2$ and $R^3$ is independently substituted with a cation of a primary, secondary or tertiary amine moiety or a guanidinyl cation. The amines can be aliphatic or aromatic amines. It will be appreciated that $R^2$ and $R^3$ can be substituted with other cations in addition to or instead of these. Similarly, one or both of $R^2$ and $R^3$ is independently substituted with an anion of a carboxylic acid, sulfonic acid, phosphonic acid, phosphoric acid, or other anionic species.

The ratio of anionic:cationic groups, and their nature (i.e., fixed or titratable) can be selected to provide a desired pKa for a particular application. In exemplary embodiments, the pKa of the lipid is appropriate for delivery of a nucleic acid into a cell, and the liposome releases the nucleic acid into the cytosol at a moderately acidic pH (e.g., from about 5 to about 7).

In an exemplary embodiment, the combination of cations and anions in the zwitterionic lipid provides a lipid with a $pK_a$ of from about 5 to 10, for example, from about 5 to about 8, or from about 5.5 to about 7. In an exemplary embodiment, the lipid includes 1, 2, 3, 4, 5, or 6 fixed or titratable cationic groups and 1, 2, 3, 4; 5, or 6 fixed or titratable anionic groups. Exemplary lipids include 1 or more titratable anionic group and 1, 2, 3, 4, 5, or 6 titratable or fixed cationic groups. In various embodiments, the lipid includes 1 or more titratable anionic groups and 1 or 2 or more titrable cationic group.

The $R^2$ and $R^3$ moieties of the zwitterionic lipid of the invention are optionally independently internally substituted with one or more heteroatom (e.g., $R^2$ and/$R^3$ is optionally a heteroalkyl moiety). These heteroatoms are optionally charged in a titratable or fixed mode.

Exemplary heteroatoms are set forth herein and include, without limitation, sulfur, oxygen, phosphorus, silicon, etc. In an exemplary embodiment, one or more of $R^2$ and $R^3$ comprises a thioether moiety.

In various embodiments, the invention provides a zwitterionic lipid according to Formula II:

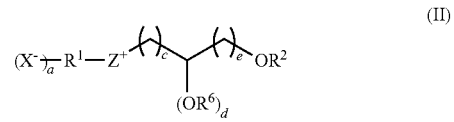

(II)

wherein the indices c and e are independently selected from the integers 1, 2, 3, 4, 5, 6, 7, 8, 9, 10, 11, 12, 13, 14, 15, 16, 17, 18 or higher. The index d is selected from the integers 0 and 1. The radical $R^6$ is a substituted or unsubstituted alkyl, a substituted or unsubstituted heteroalkyl, a substituted or unsubstituted aryl or a substituted or unsubstituted heteroaryl moiety.

As discussed above in the context of Formula I and $R^2$ and $R^3$, either or both of $R^2$ and $R^6$ are optionally substituted with one or more fixed or titratable anion and/or cation. In an exemplary embodiment, the combination of cations and anions in the zwitterionic lipid provides a lipid with a $pK_a$ of from about 5 to 10, for example, from about 5.5 to about 8, or from about 6 to about 8. In an exemplary embodiment, the lipid includes 1, 2, 3, 4, 5, or 6 fixed or titratable cationic groups and 1, 2, 3, 4, 5, or 6 fixed or titratable anionic groups. Exemplary lipids include 1 or more titratable anionic group and 1, 2, 3, 4, 5, or 6 titratable or fixed cationic groups. In various embodiments, the lipid includes 1 or more titratable anionic groups and 1 or 2 or more titrable cationic group.

The $R^2$ and $R^6$ moieties of the zwitterionic lipid of the invention are optionally independently internally substituted with one or more heteroatom (e.g., $R^2$ and/$R^6$ is optionally a heteroalkyl moiety). These atoms are optionally charged in a fixed or titratable mode. Exemplary heteroatoms are set forth herein and include, without limitation, sulfur, oxygen, phosphorus, silicon, etc. In an exemplary embodiment, one or more of $R^2$ and $R^6$ comprises a thioether moiety.

In exemplary embodiments, the invention provides a zwitterionic lipid according to Formulae III and IV:

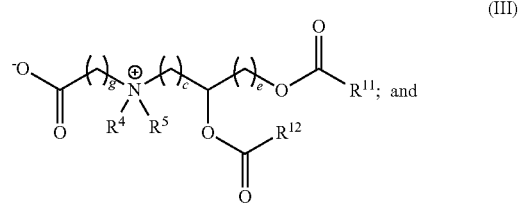

(III)

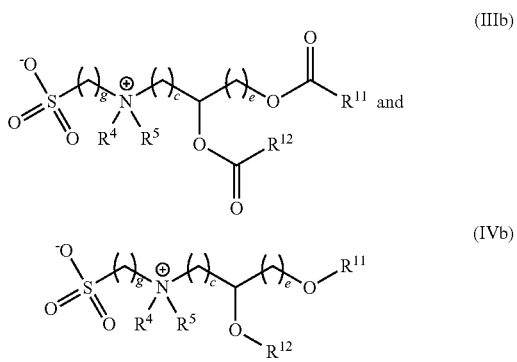

(IV)

wherein the index g is selected from the integers 1, 2, 3, 4, 5, 6, 7, 8, 9, 10, 11, 12, 13, 14, 15, 16, 17, 18, 19 and 20. The index c is selected from the integers 1, 2, 3, 4, 5, 6, 7, 8, 9, 10, 11, 12, 13, 14, 15, 16, 17 and 18. The index e is selected from the integers 1, 2, 3, 4, 5, 6, 7, 8, 9, 10, 11, 12, 13, 14, 15, 16, 17 and 18. $R^{11}$ and $R^{12}$ are members independently selected from substituted or unsubstituted alkyl, substituted or unsubstituted heteroalkyl; substituted or unsubstituted aryl and substituted or unsubstituted heteroaryl. In some embodiments, $R^4$ and $R^5$ are substituted or unsubstituted alkyl. In some embodiments, $R^4$ and $R^5$ are independently selected from $C_1$, $C_2$, $C_3$, $C_4$, $C_5$ and $C_6$ alkyl. In exemplary embodiments, $R^4$ and $R^5$ are methyl. In some embodiments, $R^{11}$ and $R^{12}$ are independently selected substituted or unsubstituted alkyl. In some embodiments, $R^{11}$ and $R^{12}$ are independently selected substituted or unsubstituted heteroalkyl. In some embodiments, $R^{11}$ and $R^{12}$ are independently selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, the index g is selected from the integers 1, 2, 3, 4, 5 and 6. In exemplary embodiments, the index g is 1. In exemplary embodiments, the index g is 2. In exemplary embodiments, the index g is 3. In some embodiments, the index c is selected from the integers from 1, 2, 3, 4, 5 and 6. In exemplary embodiments, the index c is 1. In some embodiments, the index e is selected from the integers from 1, 2, 3, 4, 5 and 6. In exemplary embodiments, the index e is 1.

In exemplary embodiments, the invention provides a zwitterionic lipid according to Formulae IIIa and IVa:

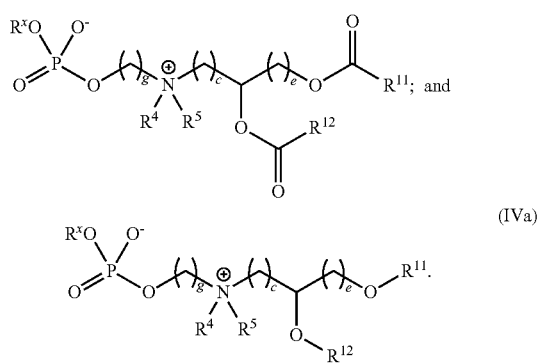

(IIIa)

(IVa)

wherein $R^x$ is selected from H and substituted or unsubstituted alkyl and is optionally present; the index g is selected from the integers 1, 2, 3, 4, 5, 6, 7, 8, 9, 10, 11, 12, 13, 14, 15, 16, 17, 18, 19 and 20; the index c is selected from the integers 1, 2, 3, 4, 5, 6, 7, 8, 9, 10, 11, 12, 13, 14, 15, 16, 17 and 18; the index e is selected from the integers 1, 2, 3, 4, 5, 6, 7, 8, 9, 10, 11, 12, 13, 14, 15, 16, 17 and 18; and $R^{11}$ and $R^{12}$ are members independently selected from substituted or unsubstituted alkyl, substituted or unsubstituted heteroalkyl, substituted or unsubstituted aryl and substituted or unsubstituted heteroaryl. In some embodiments, $R^x$ is H. In some embodiments, $R^x$ is not present. In some embodiments, $R^x$ is selected from $C_1$, $C_2$, $C_3$, $C_4$, $C_5$ and $C_6$ alkyl. In exemplary embodiments, $R^x$ is ethyl. In some embodiments, $R^4$ and $R^5$ are substituted or unsubstituted alkyl. In some embodiments, $R^4$ and $R^5$ are independently selected from $C_1$, $C_2$, $C_3$, $C_4$, $C_5$ and $C_6$ alkyl. In exemplary embodiments, $R^4$ and $R^5$ are methyl. In some embodiments, $R^{11}$ and $R^{12}$ are independently selected substituted or unsubstituted alkyl. In some embodiments, $R^{11}$ and $R^{12}$ are independently selected substituted or unsubstituted heteroalkyl. In some embodiments, $R^{11}$ and $R^{12}$ are independently selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{72}$, $C_{23}$, $C_{24}$, $C_{25}$, $C_{26}$, $C_{27}$, $C_{28}$, $C_{29}$ and $C_{30}$ alkyl. In some embodiments, the index g is selected from the integers 1, 2, 3, 4, 5 and 6. In exemplary embodiments, the index g is 1. In exemplary embodiments, the index g is 2. In exemplary embodiments, the index g is 3. In some embodiments, the index c is selected from the integers from 1, 2, 3, 4, 5 and 6. In exemplary embodiments, the index c is 1. In some embodiments, the index e is selected from the integers from 1, 2, 3, 4, 5 and 6. In exemplary embodiments, the index e is 1.

In exemplary embodiments, the invention provides a zwitterionic lipid according to Formulae IIIb and IVb:

(IIIb)

(IVb)

wherein the index g is selected from the integers 1, 2, 3, 4, 5, 6, 7, 8, 9, 10, 11, 12, 13, 14, 15, 16, 17, 18, 19 and 20; the index c is selected from the integers 1, 2, 3, 4, 5, 6, 7, 8, 9, 10, 11, 12, 13, 14, 15, 16, 17 and 18; the index e is selected from the integers 1, 2, 3, 4, 5, 6, 7, 8, 9, 10, 11, 12, 13, 14, 15, 16, 17 and 18; and $R^{11}$ and $R^{12}$ are members independently selected from substituted or unsubstituted alkyl, substituted or unsubstituted heteroalkyl, substituted or unsubstituted aryl and substituted or unsubstituted heteroaryl. In some embodiments, $R^4$ and $R^5$ are substituted or unsubstituted alkyl. In some embodiments, $R^4$ and $R^5$ are independently selected from $C_1$, $C_2$, $C_3$, $C_4$, $C_5$ and $C_6$ alkyl. In exemplary embodiments, $R^4$ and $R^5$ are methyl. In some embodiments, $R^{11}$ and $R^{12}$ are independently selected substituted or unsubstituted alkyl. In some embodiments, $R^{11}$ and $R^{12}$ are independently selected substituted or unsubstituted heteroalkyl. In some embodiments, $R^{11}$ and $R^{12}$ are independently selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, the index g is selected from the integers 1, 2, 3, 4, 5 and 6. In exemplary embodiments, the index g is 1. In exemplary embodiments, the index g is 2. In exemplary embodiments, the index g is 3. In some embodiments, the index c is selected from the integers from 1, 2, 3, 4, 5 and 6. In exemplary embodiments, the index c is 1.

In some embodiments, the index e is selected from the integers from 1, 2, 3, 4, 5 and 6. In exemplary embodiments, the index e is 1.

Further exemplary compounds of the invention include those of Formulae V and VI:

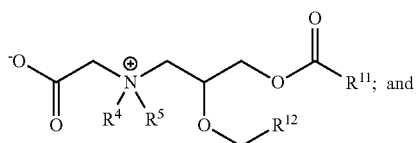
(V)

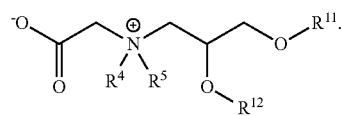
(VI)

As discussed above in the context of $R^2$ and $R^3$, either or both of $R^{11}$ and $R^{12}$ are optionally substituted with one or more fixed or titratable anion and/or cation. In an exemplary embodiment, the combination of cations and anions in the zwitterionic lipid provides a lipid with a $pK_a$ of from about 5 to 10, for example, from about 5.5 to about 8, or from about 6 to about 7. In an exemplary embodiment, the lipid includes 1, 2, 3, 4, 5, or 6 fixed or titratable cationic groups and 1, 2, 3, 4, 5, or 6 fixed or titratable anionic groups. Exemplary lipids include 1 or more titratable anionic group and 1, 2, 3, 4, 5, or 6 titratable or fixed cationic groups. In various embodiments, the lipid includes 1 or more titratable anionic groups and 1 or 2 or more titrable cationic group.

The $R^{11}$ and $R^{12}$ moieties of the zwitterionic lipid of the invention are optionally independently internally substituted with one or more heteroatom (e.g., $R^{11}$ and/or $R^{12}$ is optionally a heteroalkyl moiety). Exemplary heteroatoms are set forth herein and include, without limitation, sulfur, oxygen, phosphorus, silicon, etc. In an exemplary embodiment, one or more of $R^{11}$ and $R^{12}$ comprises a thioether moiety.

In an exemplary embodiment according to each of Formulae I-VI, $Z^+$ is:

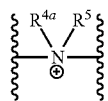

and either or both $R^4$ and $R^5$ are H. In some embodiments, $R^4$ and $R^5$ are independently selected from $C_1$, $C_2$, $C_3$, $C_4$, $C_5$ and $C_6$ alkyl. In exemplary embodiments, $R^4$ and $R^5$ are methyl.

In various embodiments according to Formulae I-VI, the zwitterionic lipid further comprises a group which is a member selected from:

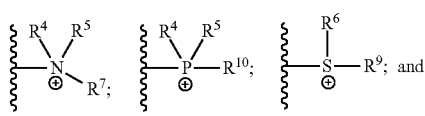

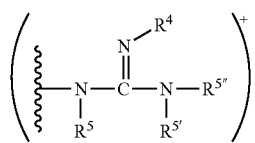

wherein $R^4$, $R^5$, $R^{5'}$, $R^{5''}$ and $R^7$ are independently H, substituted or unsubstituted alkyl, substituted or unsubstituted heteroalkyl, substituted or unsubstituted aryl or substituted or unsubstituted heteroaryl. $R^8$, $R^9$ and $R^{10}$ are members independently selected from substituted or unsubstituted alkyl, substituted or unsubstituted heteroalkyl; substituted or unsubstituted aryl or substituted or unsubstituted heteroaryl.

In various embodiments, the invention provides a zwitterionic lipid according to Formula VII:

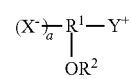
(VII)

wherein $X^-$ is a member selected from:

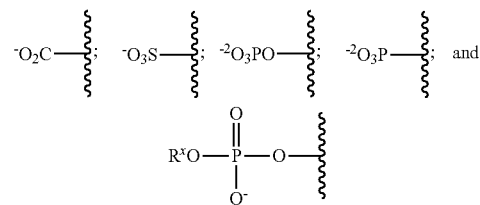

wherein $R^x$ is selected from H and substituted or unsubstituted alkyl. In some embodiments, $R^x$ is selected from $C_1$, $C_2$, $C_3$, $C_4$, $C_5$ and $C_0$ alkyl.

The index a is selected from the integers 1, 2, 3, 4, 5, 6 or higher. The symbol $R^1$ is a member selected from substituted or unsubstituted alkyl, substituted or unsubstituted heteroalkyl, substituted or unsubstituted aryl, and substituted or unsubstituted heteroaryl. The cation $Y^+$ is selected from:

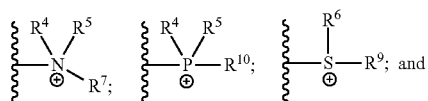

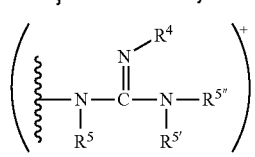

wherein $R^4$, $R^5$, $R^{5'}$, $R^{5'}$ and $R^7$ are independently H, substituted or unsubstituted alkyl, substituted or unsubstituted heteroalkyl; substituted or unsubstituted aryl and substituted or unsubstituted heteroaryl. $R^8$, $R^9$ and $R^{10}$ are members independently selected from substituted or unsubstituted alkyl, substituted or unsubstituted heteroalkyl; substituted or unsubstituted aryl or substituted or unsubstituted heteroaryl. $R^2$ is as discussed in the context of Formulae I-VI.

In various embodiments, the invention provides a zwitterionic lipid having a formula selected from:

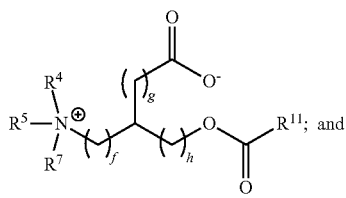
(VIII)

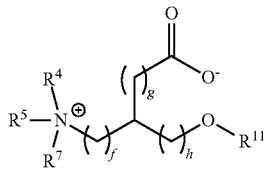
(IX)

wherein $R^4$, $R^5$, $R^7$ and $R^{11}$ are as discussed above; and f, g and h are independently selected from the integers from 0, 1, 2, 3, 4, 5, 6, 7, 8, 9, 10, 11, 12, 13, 14, 15, 16, 17, 18, 19, 20.

In various embodiments, the invention provides a zwitterionic lipid according to Formulae X and XI:

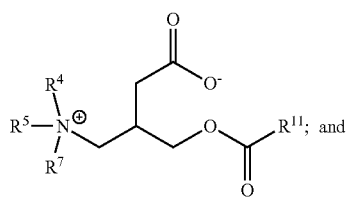
(X)

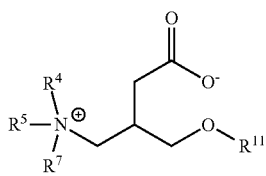
(XI)

in which $R^4$, $R^5$, $R^7$ and $R^{11}$ are as discussed above.

In exemplary embodiments, the lipids according to Formulae VII to XI further comprise one or more moiety which is a member selected from:

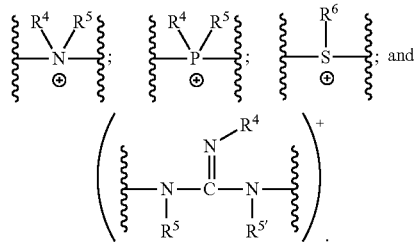

In exemplary embodiments, $R^4$, $R^5$ and $R^{5'}$ are independently H, substituted or unsubstituted alkyl, substituted or unsubstituted heteroalkyl; substituted or unsubstituted aryl or substituted or unsubstituted heteroaryl. In various embodiments, $R^6$ is selected from substituted or unsubstituted alkyl, substituted or unsubstituted heteroalkyl; substituted or unsubstituted aryl or substituted or unsubstituted heteroaryl.

Representative zwitterionic lipids of the invention according to Formulae I-XI comprise at least one $Z^{a+}$ group, wherein $Z^{a+}$ is a member selected from:

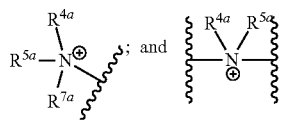

and a combination thereof. In exemplary embodiments, at least one of $R^{4a}$, $R^{5a}$ and $R^{7a}$ is H.

In an exemplary embodiment, the combination of cations ($Z^+$ and $Z^{a+}$) and anions in the zwitterionic lipid according to Formulae I-XI provides a lipid with a $pK_a$ of from about 5 to 10, for example, from about 5.5 to about 8, or from about 6 to about 7. In an exemplary embodiment, the lipid includes 1, 2, 3, 4, 5, or 6 fixed or titratable cationic groups and 1, 2, 3, 4, 5, or 6 fixed or titratable anionic groups. Exemplary lipids include 1 or more titratable anionic group and 1, 2, 3, 4, 5, or 6 titratable or fixed cationic groups. In various embodiments, the lipid includes 1 or more titratable anionic groups and 1 or 2 or more titrable cationic group.

In exemplary embodiments, the zwitterionic lipid of the invention has a pKa greater than 5. Exemplary lipids of the invention have a pKa from about 5.5 to about 8, e.g., from about 6 to about 7.

The $R^{4a}$, $R^{5a}$ and $R^{7a}$ moieties of the zwitterionic lipid of the invention are optionally independently internally substituted with one or more heteroatom (e.g., $R^{4a}$, $R^{5a}$ and/or $R^{7a}$) is optionally a heteroalkyl moiety). Exemplary heteroatoms are set forth herein and include, without limitation, sulfur, oxygen, phosphorus, silicon, etc. In an exemplary embodiment, one or more of $R^{4a}$, $R^{5a}$ and/or $R^{7a}$ comprises an ether and/or thioether moiety.

Representative zwitterionic lipids of the invention include a substituted or unsubstituted heterocycloalkyl moiety (e.g., morpholino and piperizinyl) and/or a ketal moiety and one or more of $Z^+$ and $Z^{a+}$ in any combination. The ketal moiety is a substituent of any of the linker or hydrophobic chains alone or in any combination (e.g., $R^1$, $R^2$, $R^3$, $R^6$, $R^{11}$, $R^{12}$ or any subunits thereof). An exemplary ketal moiety has the formula:

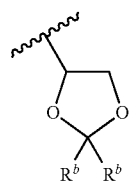

in which each $R^b$ is independently selected from sos alkyl, heteroalkyl, aryl, heteroaryl, or alkyl group substituents as that term is defined herein. Exemplary hydrophobic chains on such a lipid include oleyl (C18:1) and/or linoleyl (C18:2).

Examples of some double-cationic zwitterlipids with fixed and/or titratable cations according the invention include:

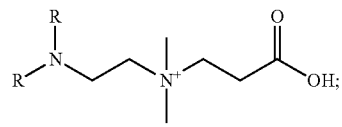

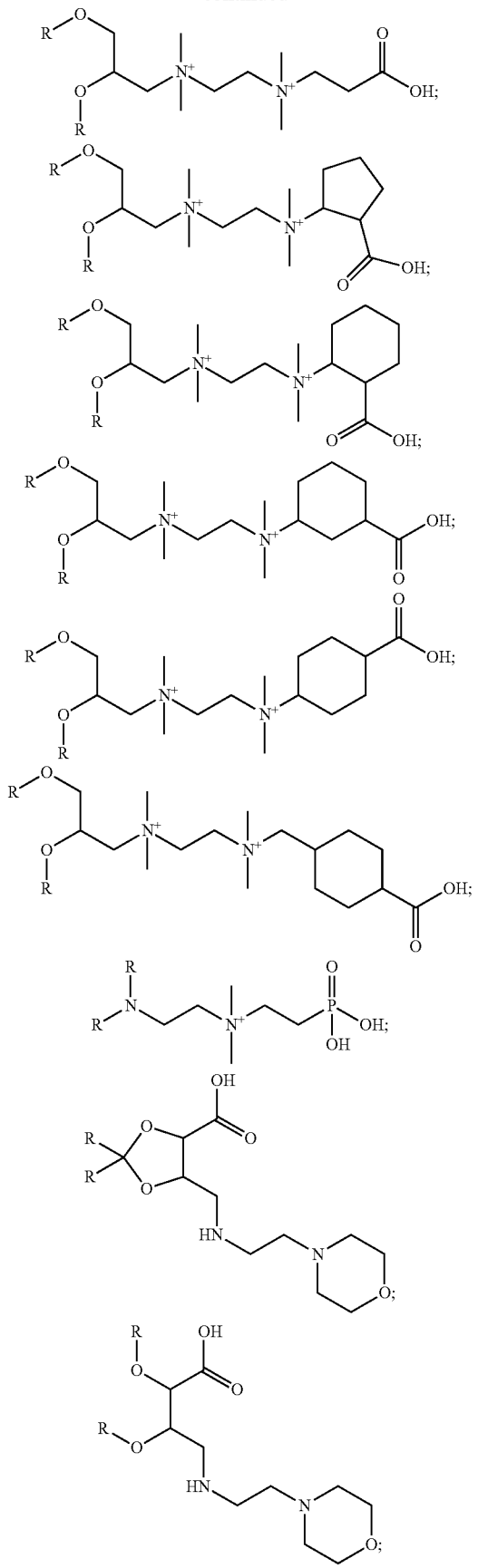

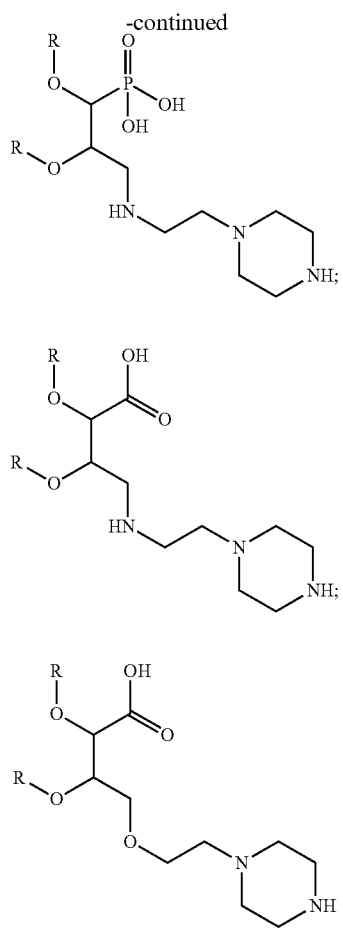

in which each R group is independently selected and correspond to $R^2$, $R^3$, $R^6$, $R^{11}$ and $R^{12}$ as set forth hereinabove.

Figure 1:
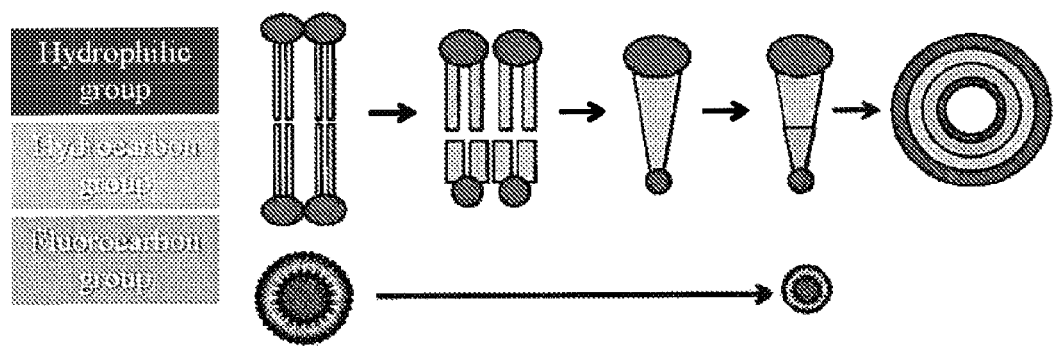
FIG. 1 is a schematic diagram showing the development of zwitterionic asymmetric bolaamphiphiles.
Figure 2:
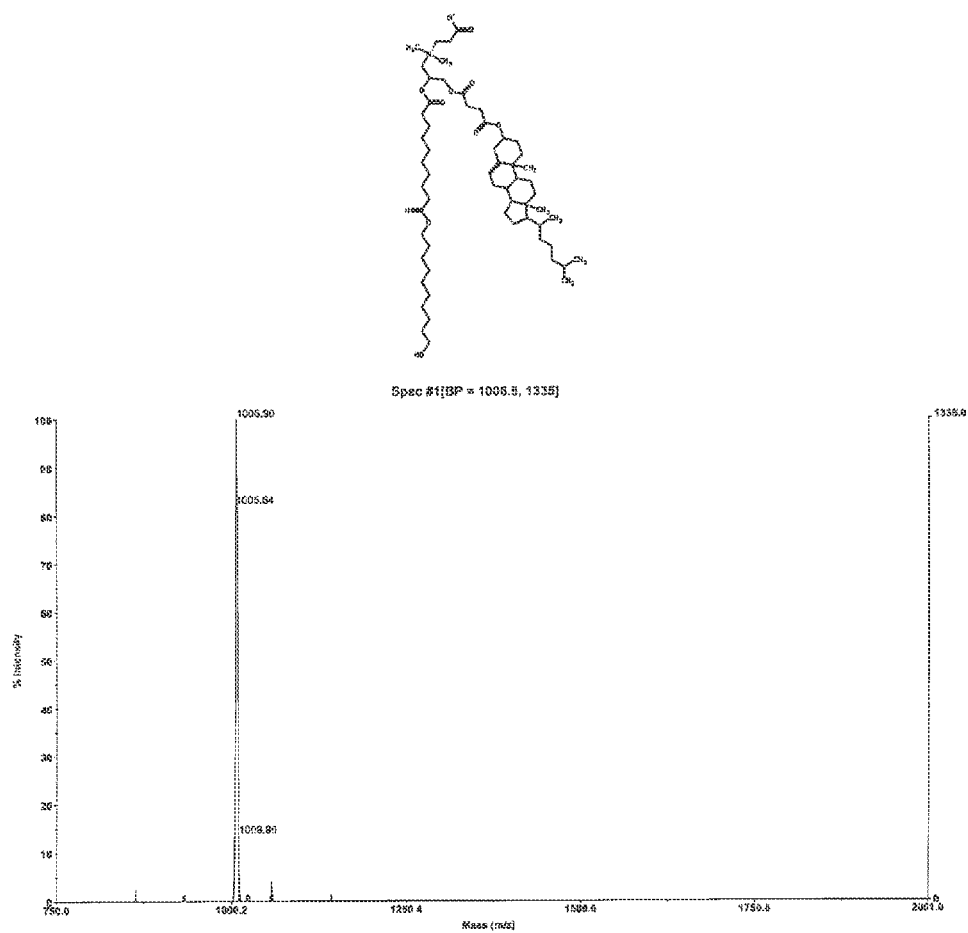
FIG. 2 is a MALDI spectrum of a compound of the invention.
Figure 3:
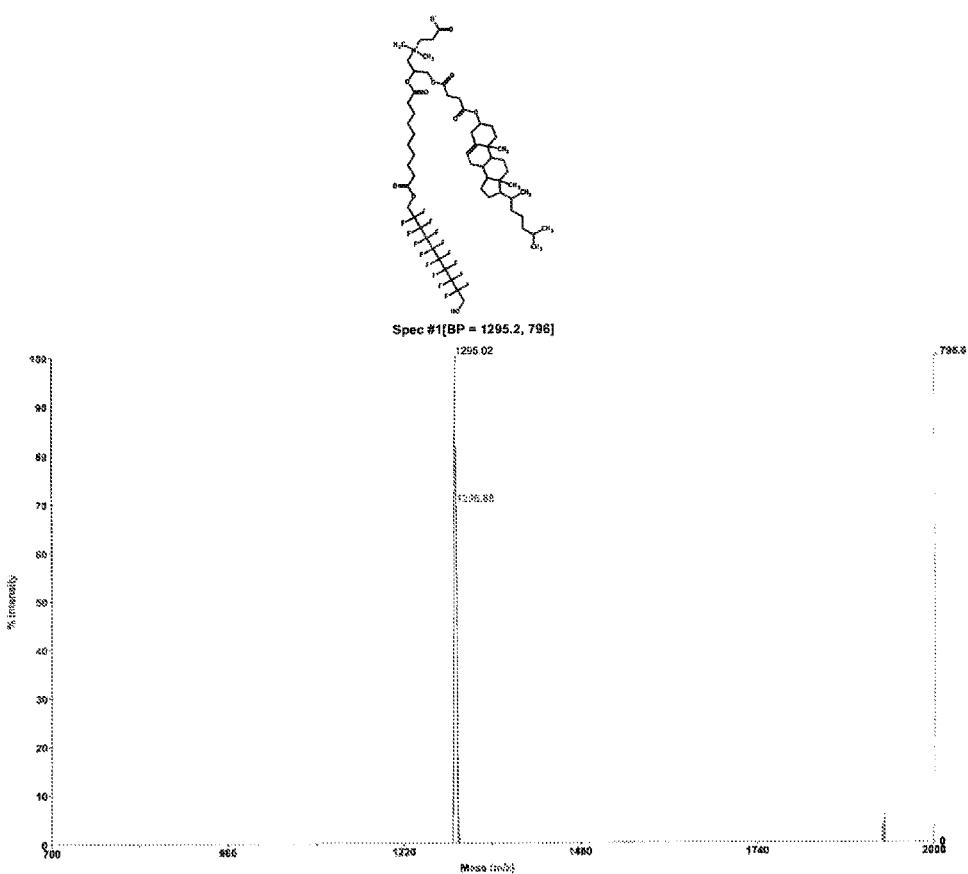
FIG. 3 is a MALDI spectrum of a compound of the invention.
Figure 4:
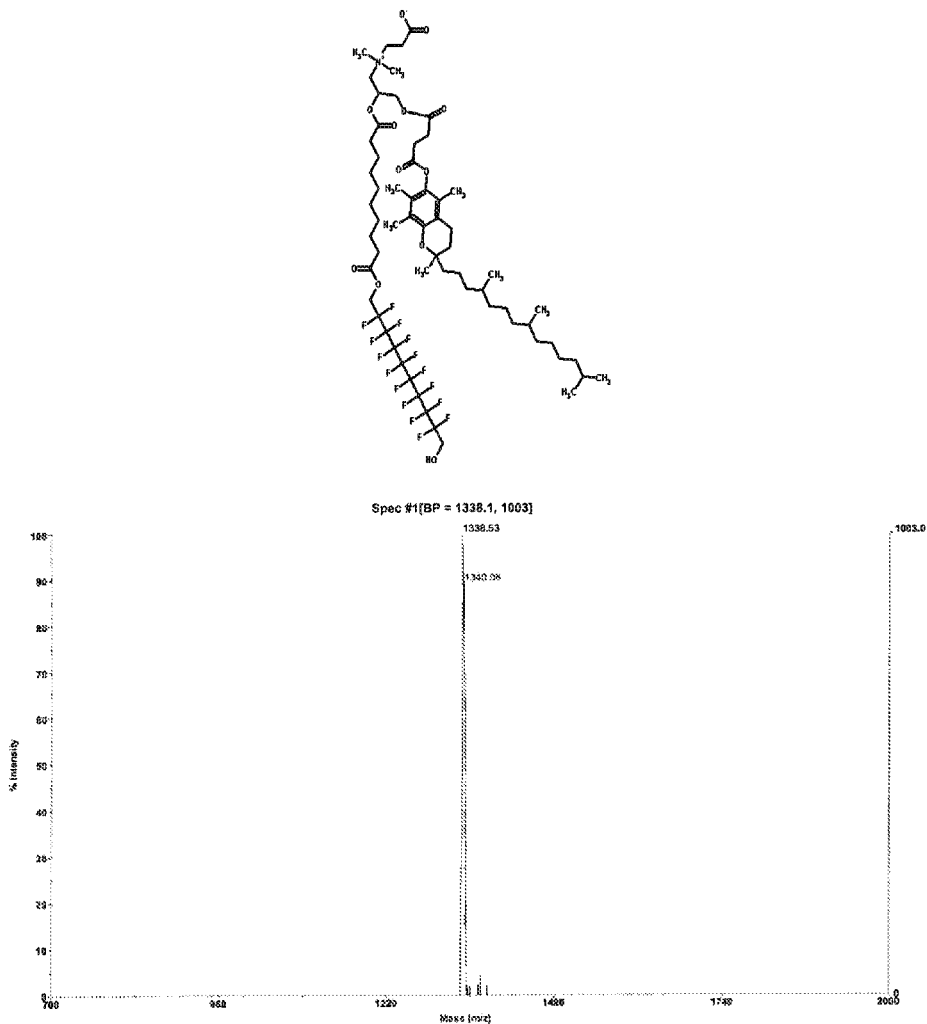
FIG. 4 is a MALDI spectrum of a compound of the invention.
Figure 5:
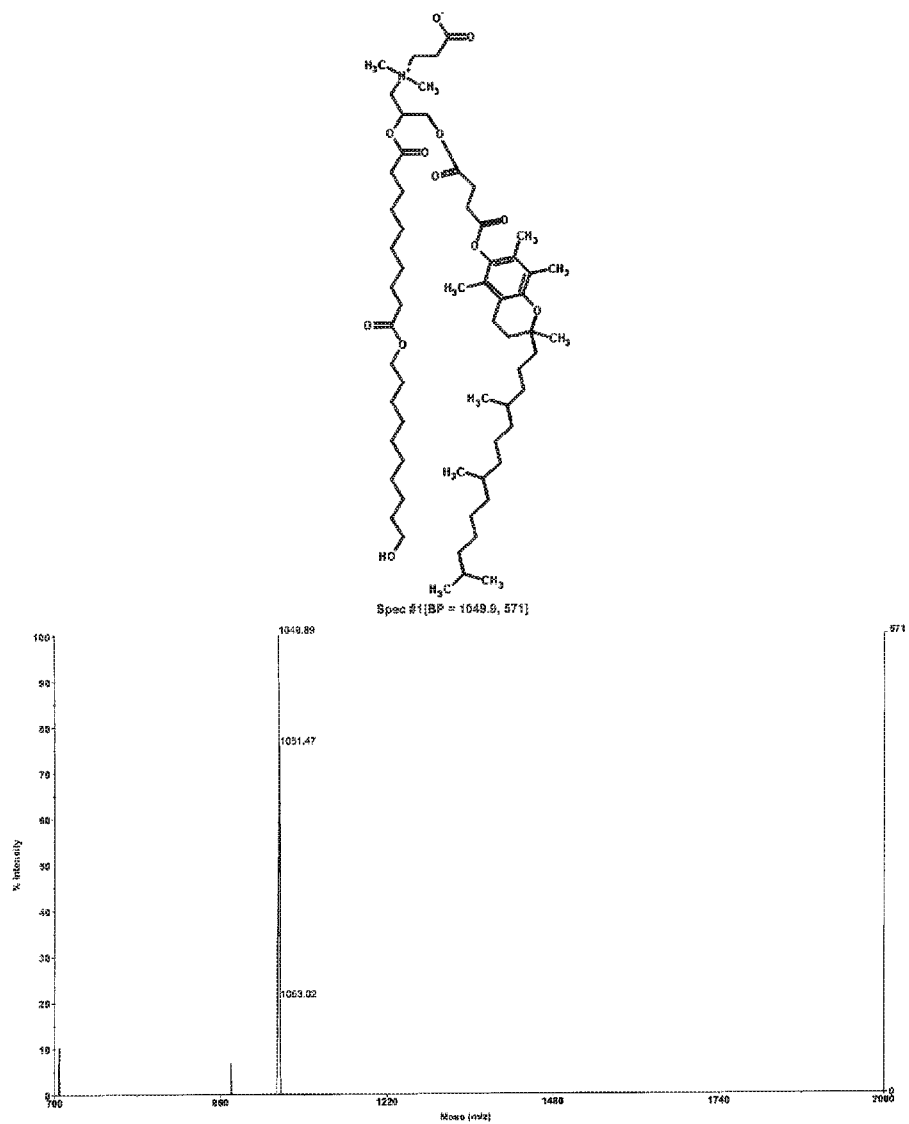
FIG. 5 is a MALDI spectrum of a compound of the invention.
Figure 6:
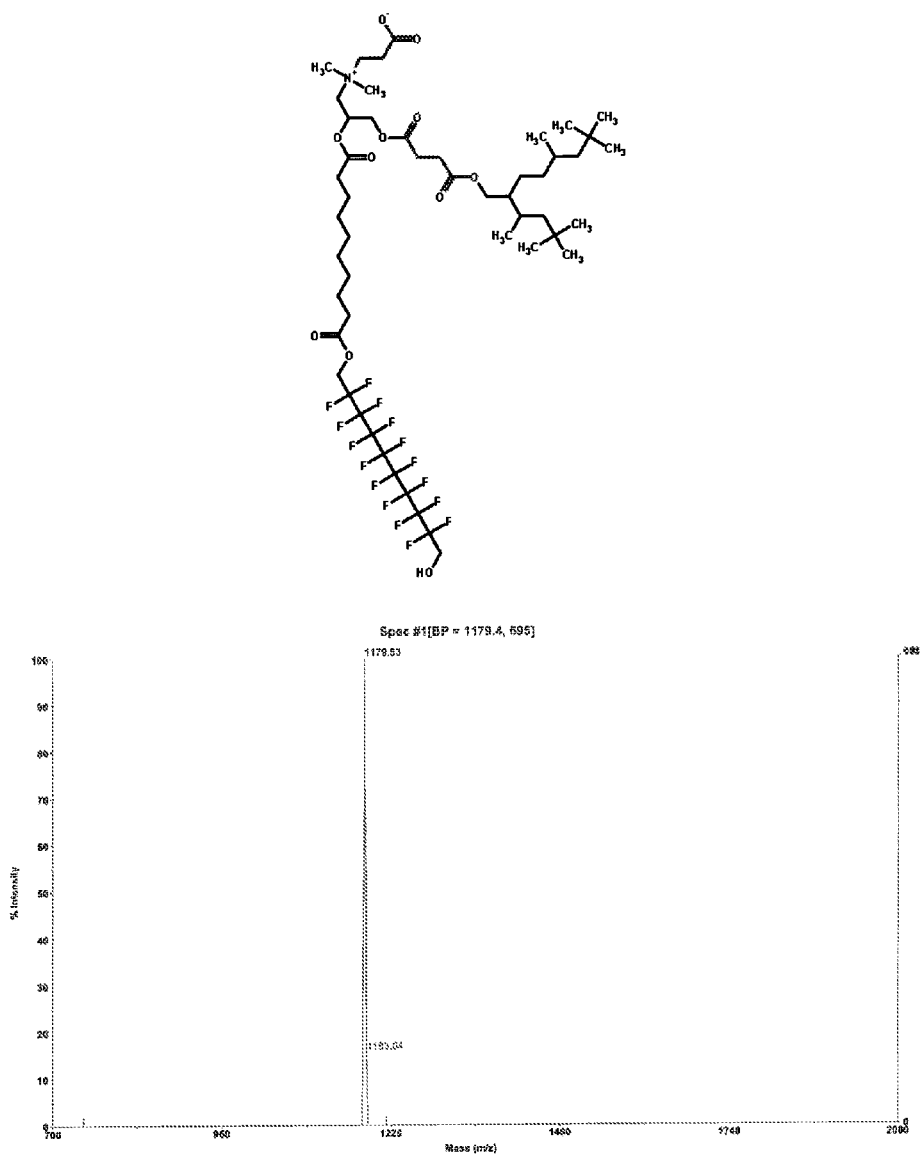
FIG. 6 is a MALDI spectrum of a compound of the invention.
Figure 7:
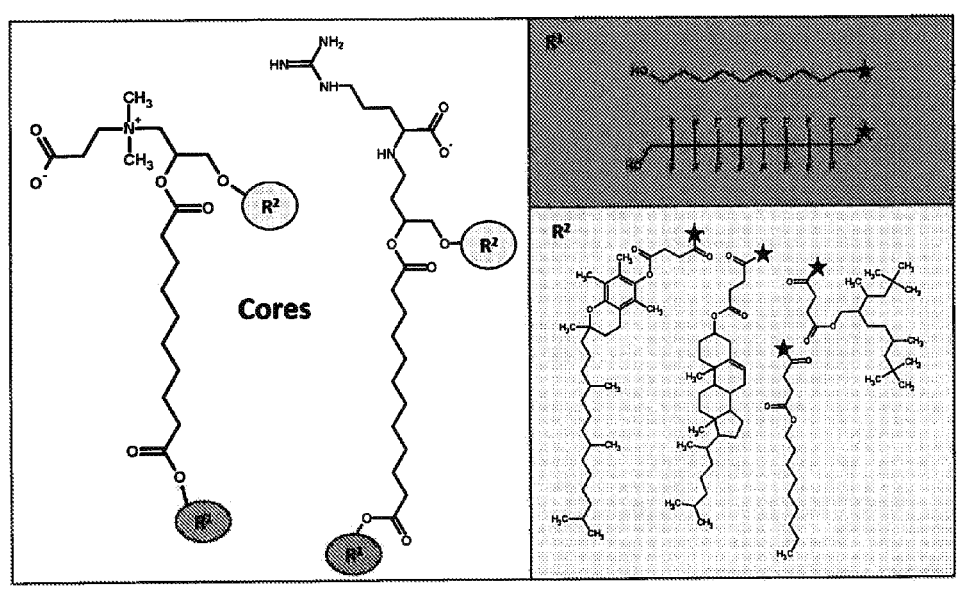
FIG. 7 shows an exemplary library of zwitterionic asymmetric bolaamphiphiles.
Figure 8:
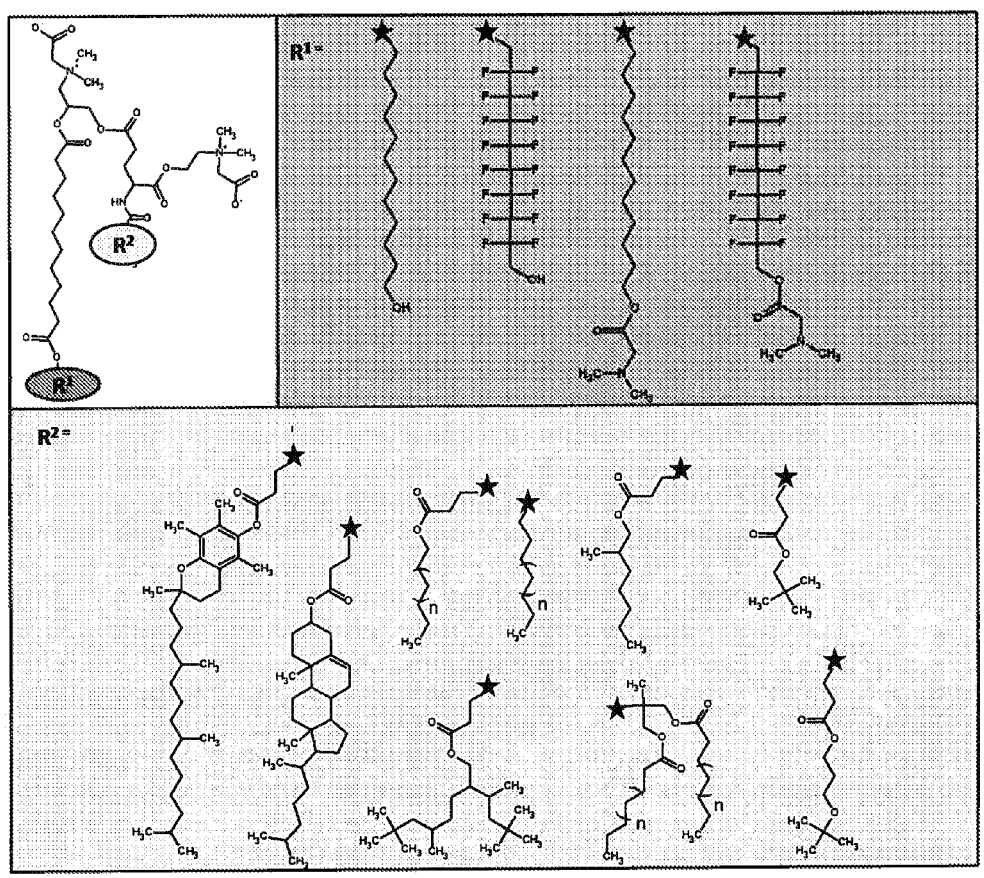
FIG. 8 shows an exemplary library of zwitterionic asymmetric bolaamphiphiles.
Figure 9:
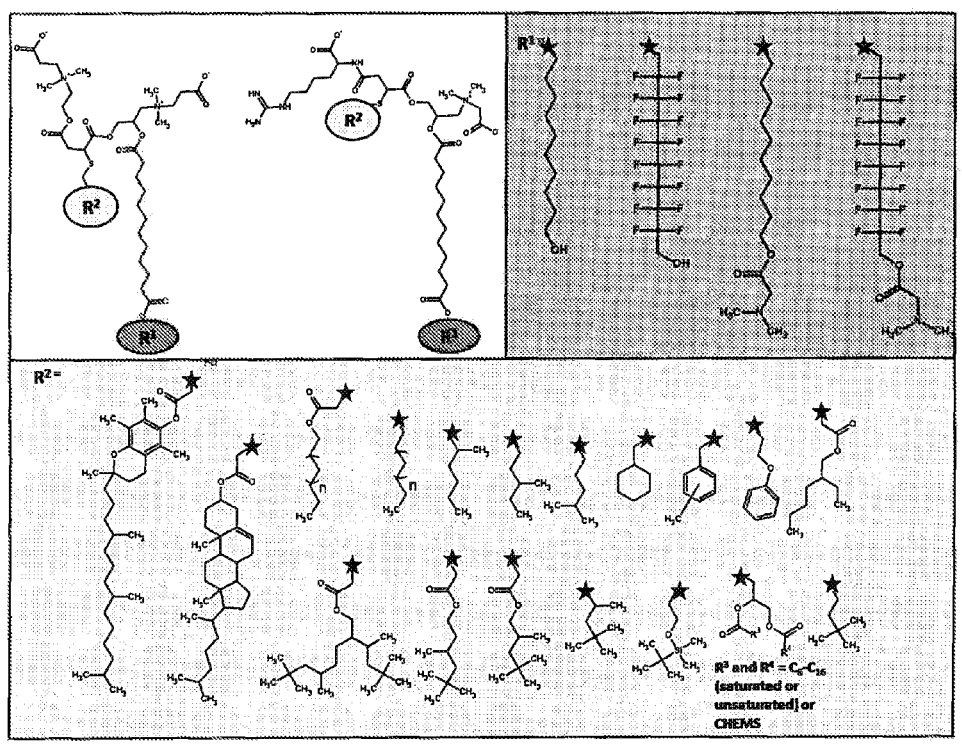
FIG. 9 shows an exemplary library of thiol zwitterionic asymmetric bolaamphiphiles.
Figure 10:
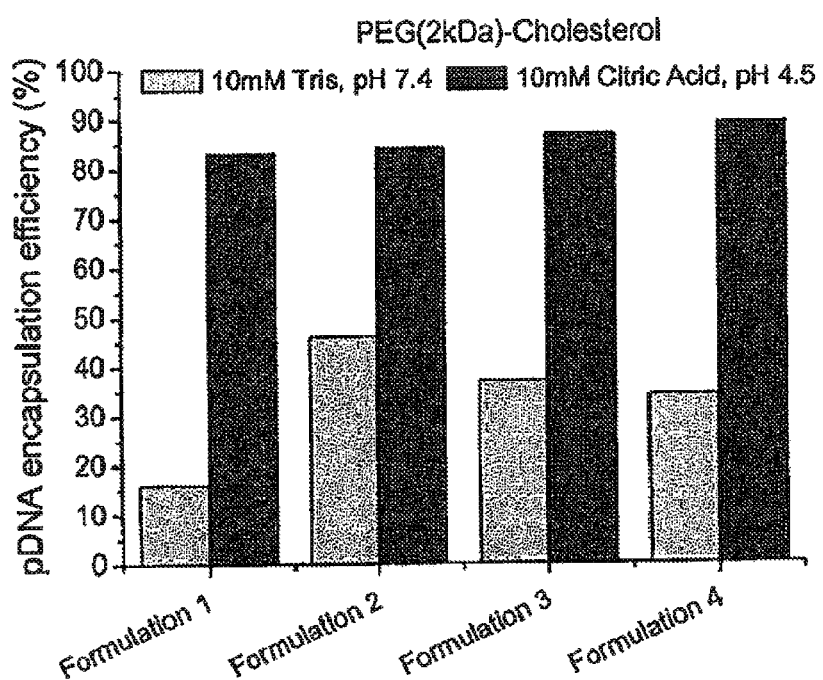
FIG. 10 is a graphic representation of the effect of pH on encapsulation efficiency of DNA.
Figure 11:
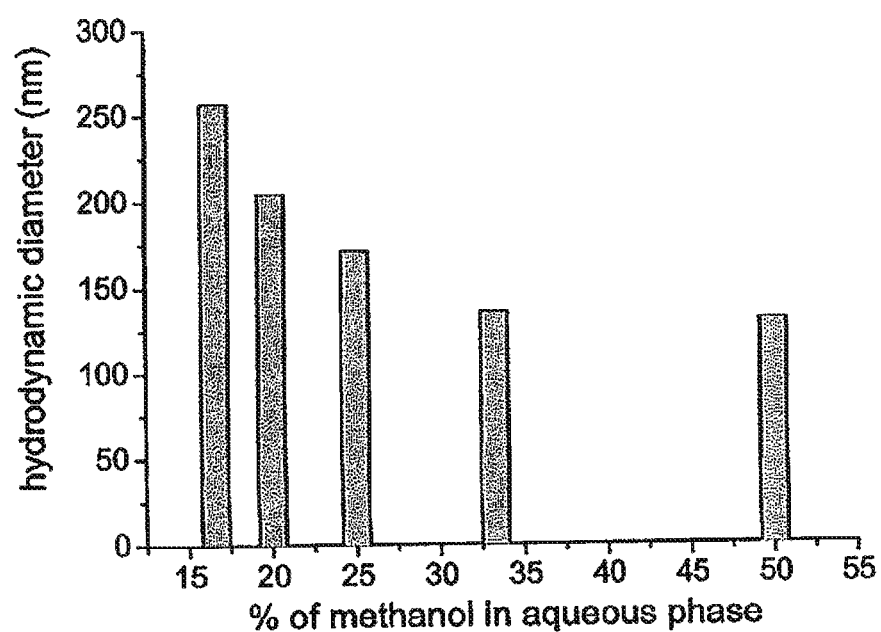
FIG. 11 is a graphic representation of effect of the final percentage of methanol in the aqueous phase on liposome diameter.
Figure 12:
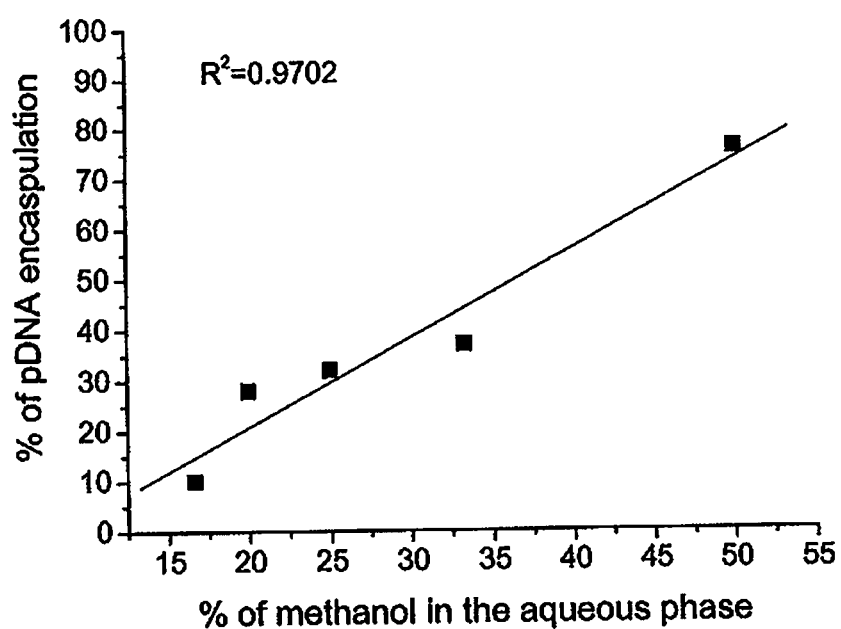
FIG. 12 is a graphic representation of the effect of the final percentage of methanol in the aqueous phase on DNA encapsulation efficiency.
Figure 13:
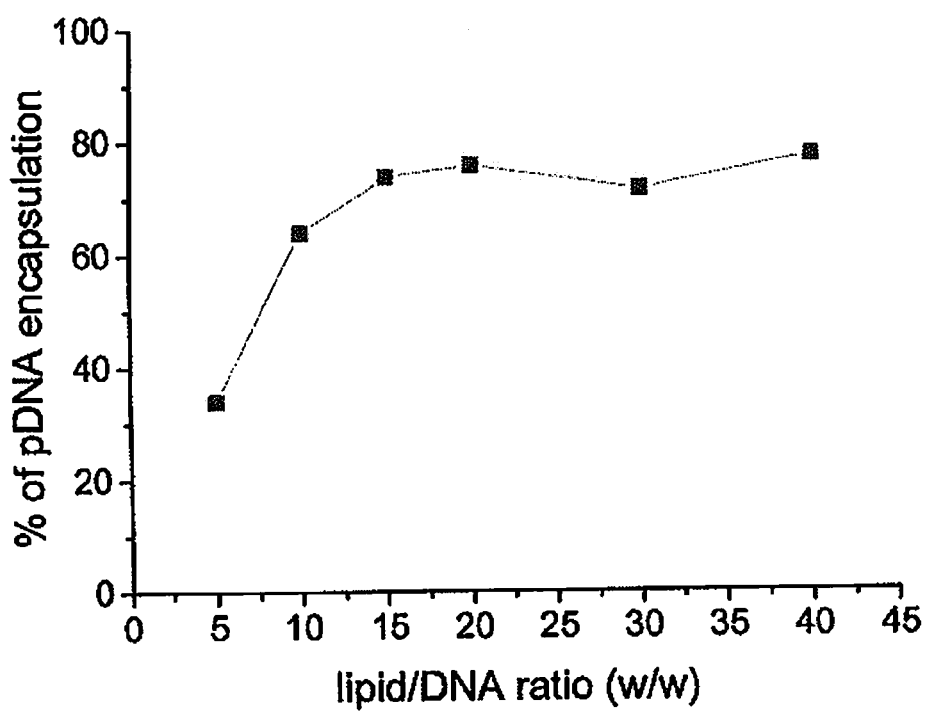
FIG. 13 is a graphic representation of the effect of lipid concentration on encapsulation efficiency of DNA.
Figure 14:
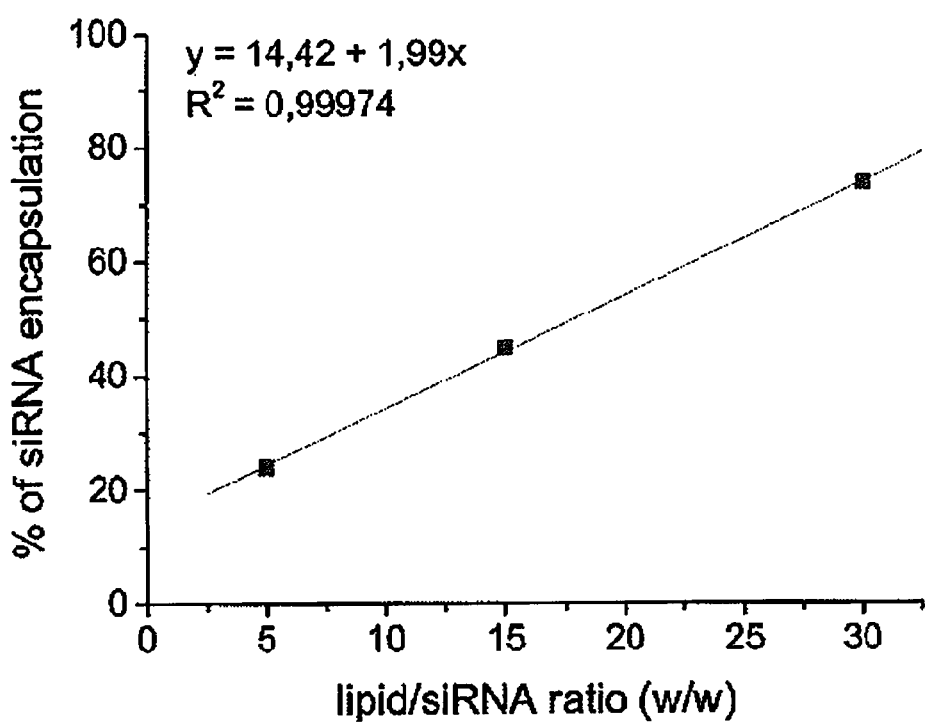
FIG. 14 is a graphic representation of the effect of lipid concentration on encapsulation efficiency of siRNA.
Figure 15:
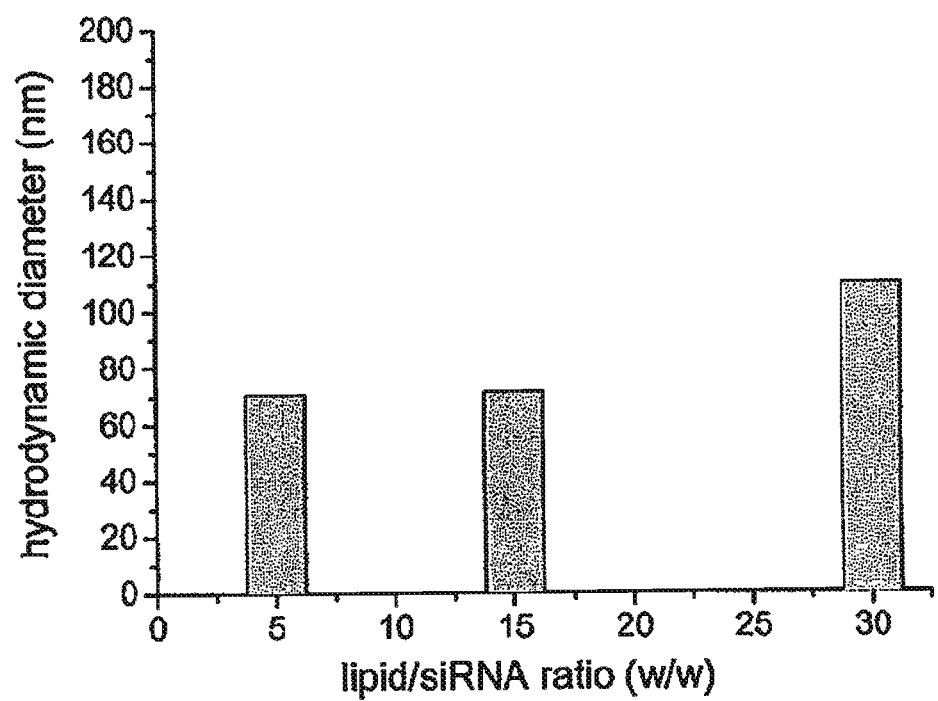
FIG. 15 is a graphic representation of the effect of lipid concentration on hydrodynamic diameter of liposomes.
Figure 16:
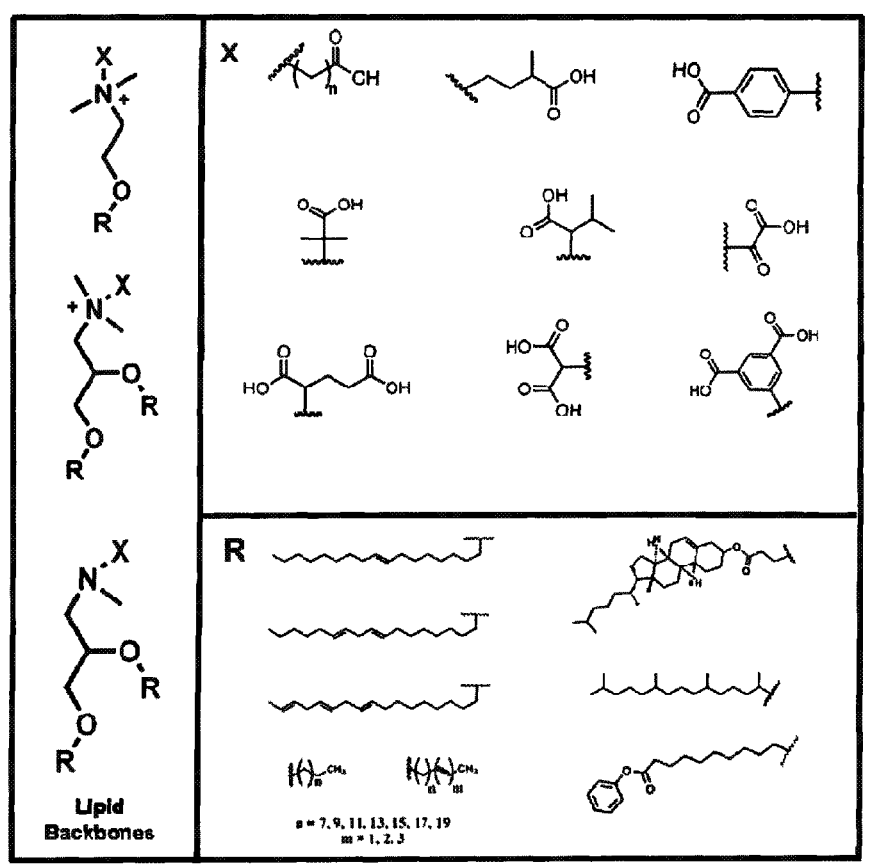
FIG. 16 is a general schematic of representative betaine-like lipid backbones, carboxylate head groups (X), and hydrophobic lipid tail structures (R).
Figure 17:
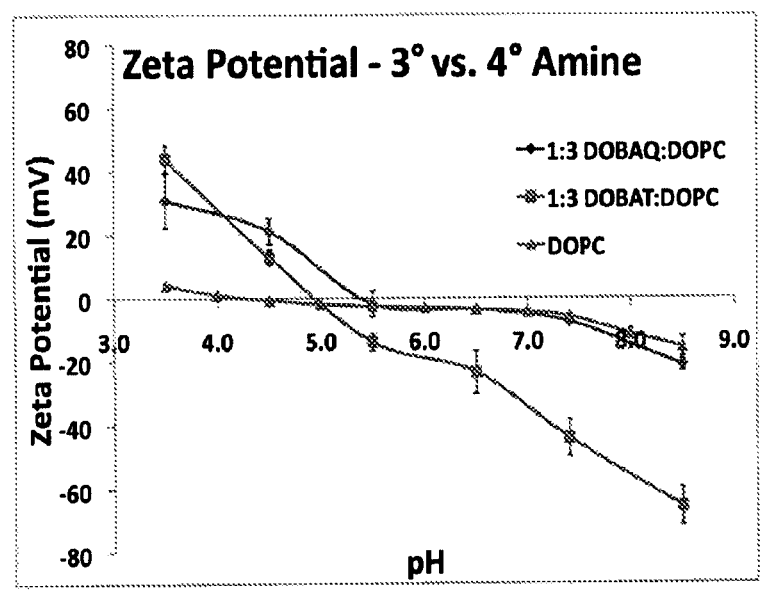
FIG. 17 shows the effect of 3° vs. 4° amine on Zeta Potential: The zeta potential of vesicles with tertiary and quaternary BLL was studied using 1:3 DOBAQ:DOPC liposomes. Liposomes containing quaternary BLL remain neutral at pH>pI, while liposomes containing tertiary BLL move from neutral to anionic as pH increases above the pI due to deprotonation of the amine.
Figure 18:
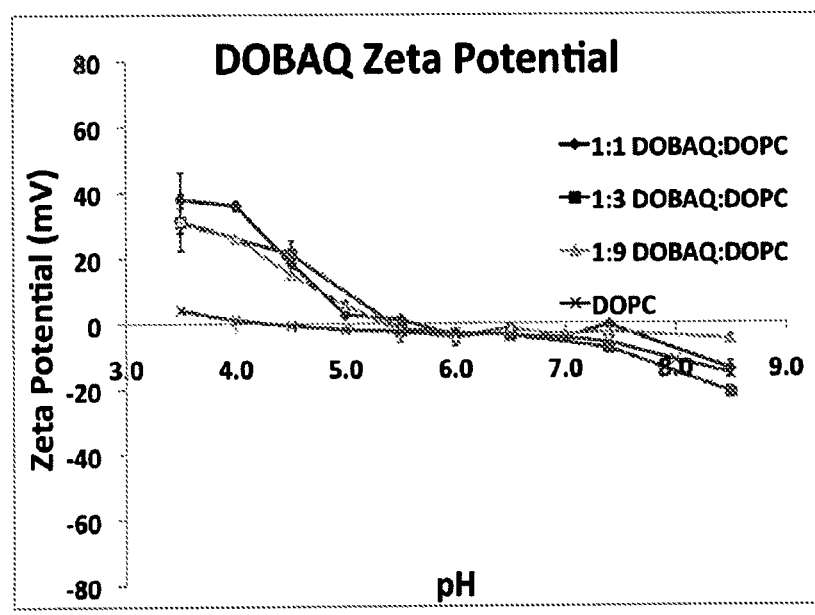
FIG. 18 shows the effect of formulation on Zeta Potential: The impact of changing the ratio of BLL:DOPC was investigated using DOBAQ as a model BLL. The general relationship between pH and zeta potential is maintained at all ratios tested, though the pI and max values can change slightly.
Figure 19:
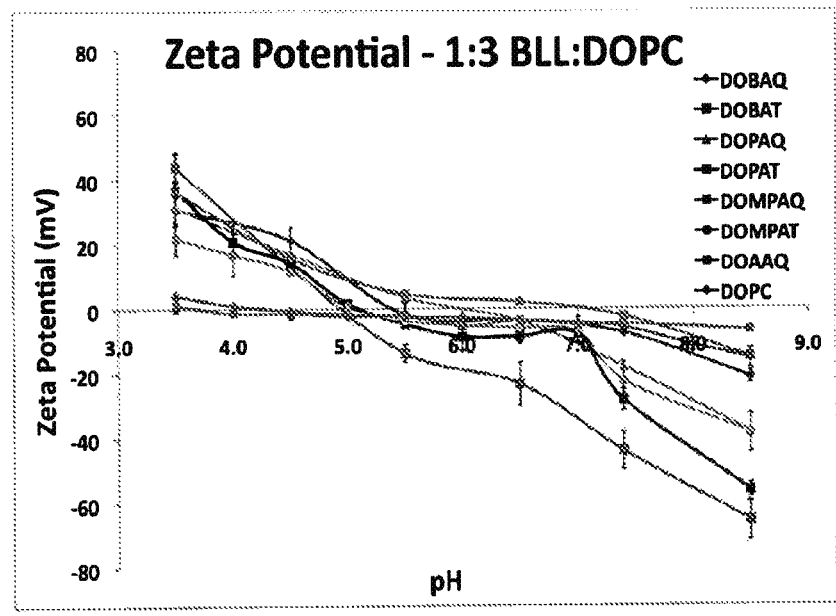
FIG. 19 shows Zeta Potential of 1:3 BLL:DOPC Vesicles: The pH-responsive behavior of all seven BLL was compared in a 1:3 BLL:DOPC formulation to determine if significant differences existed between lipids with varying head group structures. DOAAQ remains neutral at all pH values. All other lipids show pH responsive behavior, with 4° BLL generally transitioning from cationic to neutral, and 3° from cationic to neutral to anionic.
Figure 20:
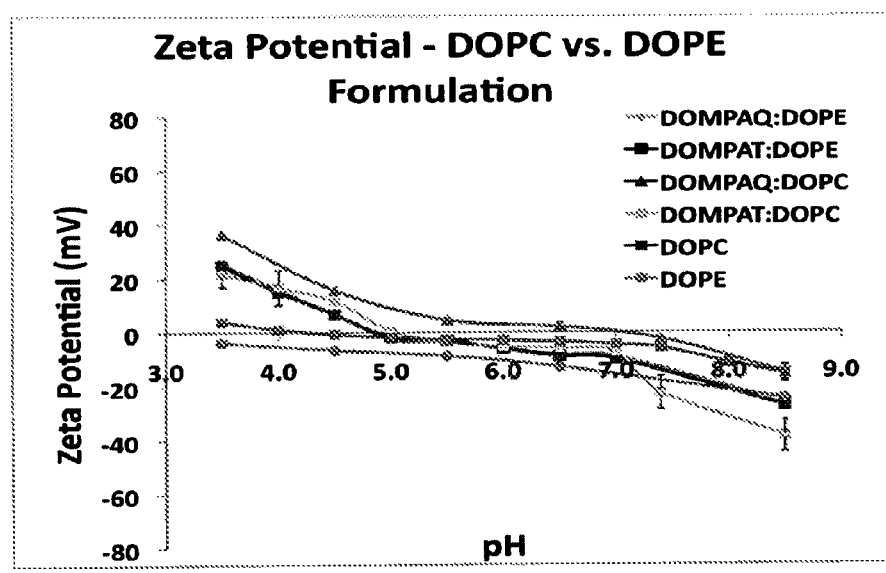
FIG. 20 shows the effect of Helper Lipid on Zeta Potential: Tertiary and Quaternary BLL were formulated at a 1:3 ratio with both DOPC and DOPE to determine if changing the lipids in the formulation has an effect on the pH-responsive behavior of BLL.
Figure 21:
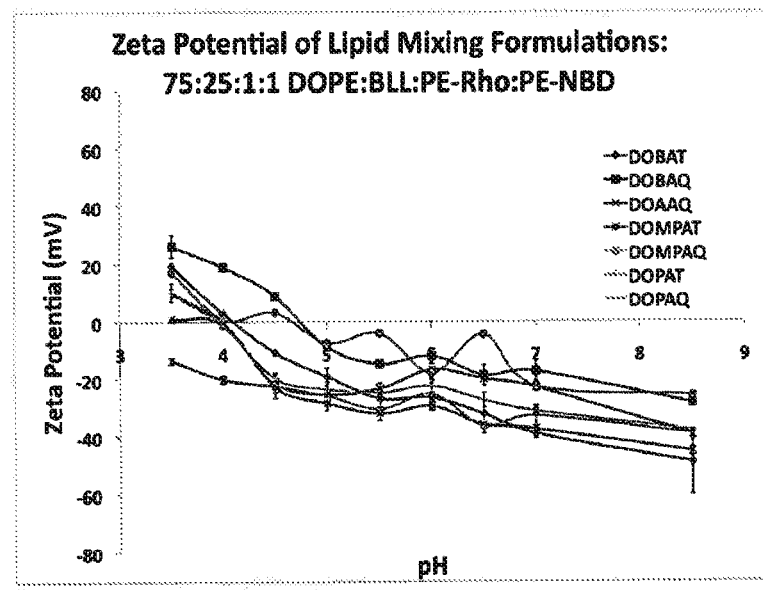
FIG. 21 shows Zeta Potential of Lipid Mixing Formulations: The zeta potential of formulations used for the lipid mixing FRET assay was measured. All formulations show a negative shift in zeta potential compared to BLL: DOPC and BLL:DOPE formulations that do not contain the FRET pair lipids. Further analysis is required to fully understand this behavior.
Figure 22:
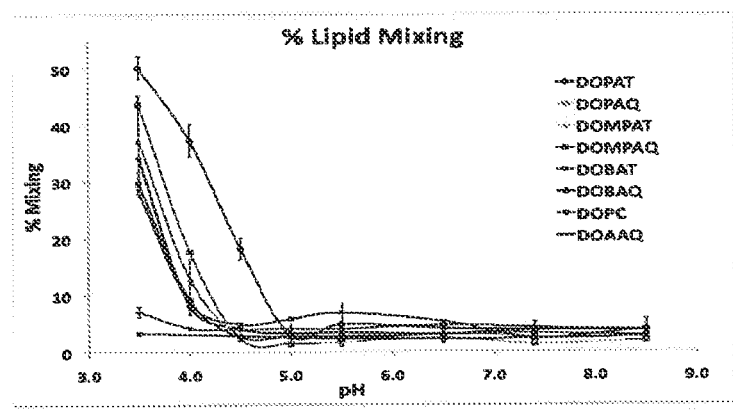
FIG. 22 shows Lipid Mixing of BLL Containing Vesicles: The pH-responsive lipid mixing behavior of all seven BLL was compared in a 75:25:1:1 BLL:DOPE:PE-Rho:PE-NBD formulation using a FRET assay.
Figure 23:
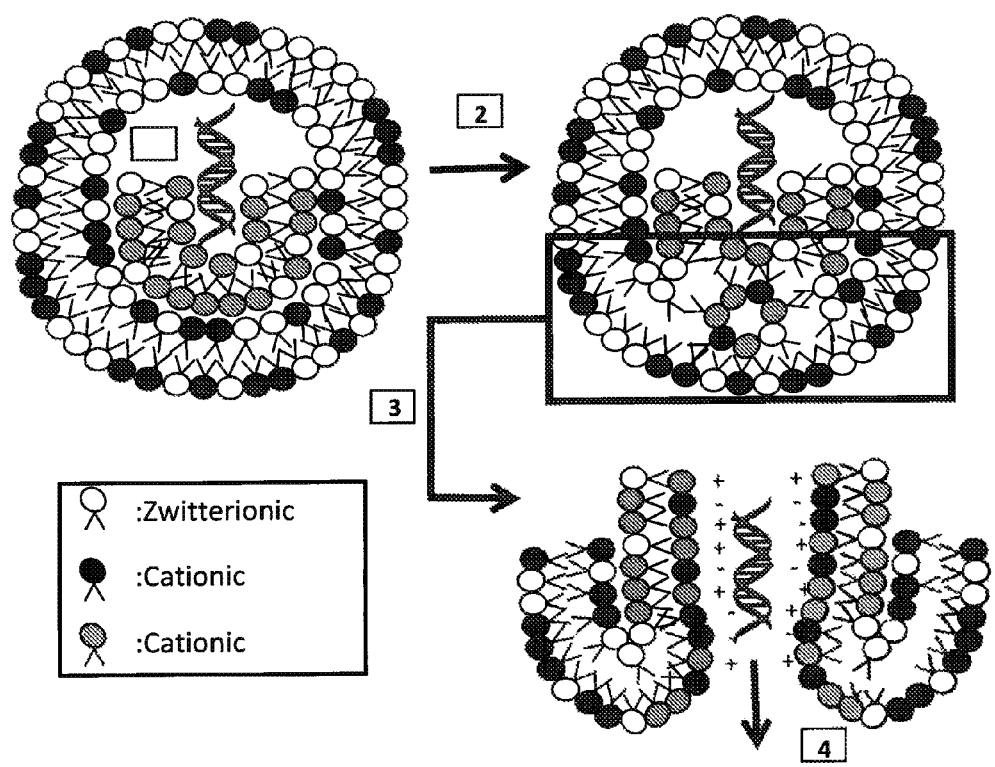
FIG. 23 shows an exemplary mechanism for the escape of an agent from a liposome of the invention: 1) 2) Acidification of endosomes to lysosomes; b) Protonation of zwitterionic lipids=>positively charged. Interaction of transiently cationic lipids with negatively charged endosomal membrane and formation of a hexagonal phase intermediate; 3) Membrane permeabilization and ion pairing; and 4) Release of nucleic acid into the cytosol.
Figure 24:
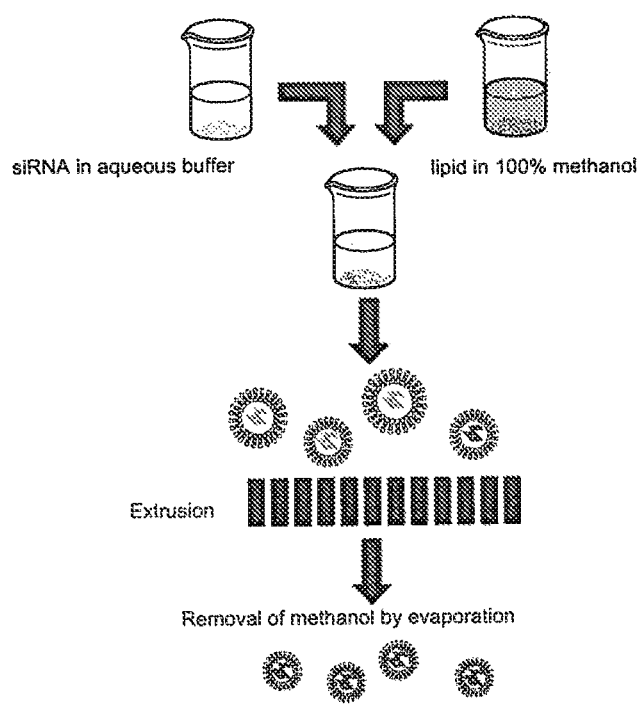
FIG. 24 shows an exemplary method of encapsulating an agent in a liposome of the invention: Zwitterionic nanolipid particles (ZNLP) are prepared by dissolving the lipid mixture in methanol and inject it into an aqueous siRNA solution under constant stirring. 5-10 min after particle formation liposomes are extruded through either 50 nm or 80 nm polycarbonate membranes 7 times. Methanol can be removed by either evaporation or dialysis.
Figure 25:
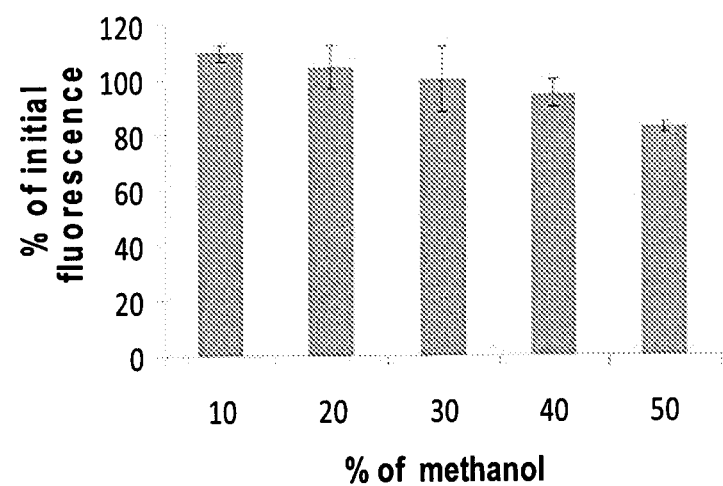
FIG. 25 shows fluorescence recovery of mKate after removal of methanol: Monomeric Katushka (mKate), a fluorescent protein, was used as a model protein for encapsulation, allowing for fast and accurate analysis. Upon denaturation mKate loses its fluorescence. As methanol can lead to denaturation and loss of protein activity, we incubated mKate with increasing amounts of methanol. Loss of activity occurs visibly at a methanol concentration of 40-50%. After removal of methanol by evaporation, protein activity is recovered. Liposomes were prepared with 30% of methanol.
Figure 26:
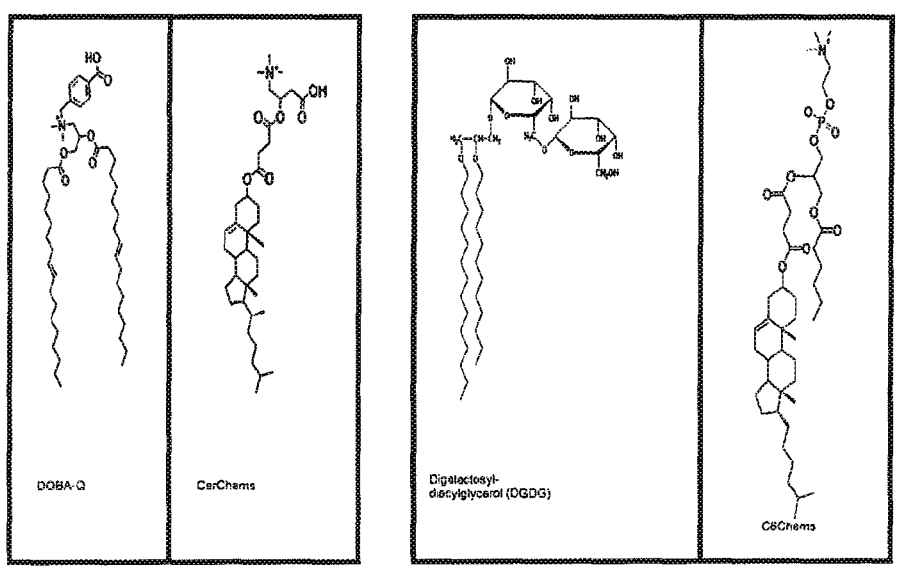
FIG. 26 shows the chemical structure of exemplary zwitterionic and helper lipids.
Figure 27:
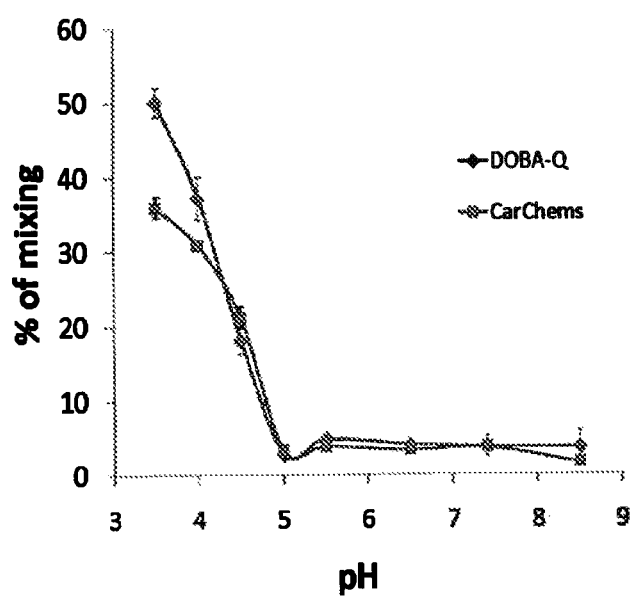
FIG. 27 shows Lipid mixing of DOBAQ and CarChems liposomes as a function of pH: To estimate the potential of CarChems and DOBA-Q to fuse with the endosomal membrane, a lipid mixing assay based on fluorescence resonance energy transfer was performed. Zwitterionic liposomes (DOPE/ZL/PE-Rho/PE-NBD 75/25/1/1) were incubated with acceptor liposomes DOPE/DOPG (70/30) for 5 min. An increase in NBD-PE fluorescence indicates lipid mixing by dilution of the membrane bound FRET-pair.
Figure 28:
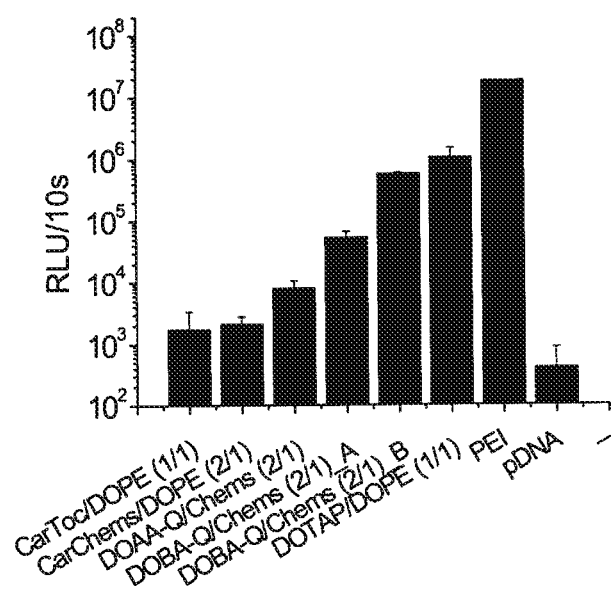
FIG. 28 shows transfection efficiency of ZLNP in B16F10 cells expressed as relative light units (RLU/10s): To measure the transfection activity of the ZNLP from various zwitterlipids, B16F10 cells were incubated with liposomes encapsulating pCMV-luc DNA. All formulations contained 5% PEG-DSPE and displayed a negative/neutral surface charge.

In exemplary embodiments, the lipids of the invention are asymmetric bolaamphiphiles. Asymmetric bolaamphiphiles (ABAs) with zwitterionic head-groups can pack asymmetrically into monolayer vesicular structures capable of encapsulating small molecules, nucleic acids, or proteins. A stable asymmetric monolayer is formed when both hydrophilic ends ends are in their preferred curvature state (termini with a positive radius of curvature on the exterior of the vesicle and termini with a negative radius of curvature on the interior of the vesicle). Each ABA exhibits an overall "wedge-like" structure, as shown in FIG. 1, with a tapered hydrophobic segment terminated by two hydrophilic moieties that differ significantly in size. Asymmetric packing is promoted by the incorporation of fluorocarbon segments in the hydrophobic region adjacent to the small hydrophilic group, which phase separate from hydrocarbon portions. The larger hydrophilic segment consists of either one or two zwitterionic groups as described herein. The small hydrophilic termini can consist of a variety of reactive functional groups, e.g., an alcohol, carboxylic acid, aldehyde, thiol, or amine (FIGS. 7-9).

In an exemplary embodiment, the invention provides first generation asymmetric bolaamphiphiles (FGZA) (FIG. 1). The FGZAs are designed to form vesicles when dispersed in an aqueous solution and to be sensitive to changes in pH which result in changes in the charge and therefore structure of the zwitterionic group. The FGZAs consist of two hydrophobic chains, one long (e.g., $C_{14}$-$C_{26}$) and one branched. The long chain can be attached to an aminodiol core (e.g., dimethylaminopropanediol). The long chain segment of the FGZAs can consist of either a fluorinated or hydrogenated carbon chain ($C_6$-$C_{12}$), with a terminal functional group such as a hydroxyl, amine, carboxylic acid, aldehyde, or thiol. This terminal group can be further functionalized to enhance the encapsulation of a specific molecule or macromolecule. Structures and characterization of representative FGZA's are shown in FIGS. 2-6.

In various embodiments, the invention provides second generation FGZA and second generation FGZA's incorporating a thioether moiety.

Synthesis

In general, the lipids of the invention are prepared by art-recognized reactions. A number of exemplary synthetic routes are set forth herein for the purposes of illustration, however, the scope of this illustration is not intended to be limiting.

The betaine-like lipids of the invention consist of two distinct regions, a head group and linker region, and a hydrophobic tail. Suitable hydrophobic tail moieties include those derived from steroids and their derivatives, fatty acids and fatty alcohols having from about 8 to about 24 carbon atoms in a backbone. Exemplary fatty acids, fatty amines and fatty alcohols have at least about 10 carbon atoms in a backbone, and more typically have at least about 18 carbon atoms in a backbone. In various embodiments, the fatty acids and alcohols from which lipid moieties are derived have fewer than about 20 carbon atoms in a backbone. Exemplary linkers are formed from substituted or unsubstituted alkyl, heteroalkyl, aryl and heteroaryl moieties. The headgroups and linkers are discussed further herein.

The two regions of the lipids can be conjugated through covalent bonds by reacting precursors for each region having reactive functional groups to form a linkage fragment, which is a covalent bond.

Currently favored classes of reactions for use in assembling the compounds of the invention are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:
(a) carboxyl groups and derivatives thereof including, but not limited to activated esters, e.g., N-hydroxysuccinimide esters, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;

(b) hydroxyl groups, which can be converted to esters, sulfonates, phosphoramidates, ethers, aldehydes, etc.

(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, allowing derivatization via formation of carbonyl derivatives, e.g., imines, hydrazones, semicarbazones or oximes, or via such mechanisms as Grignard addition or alkyllithium addition;

(f) sulfonyl halide groups for reaction with amines, for example, to form sulfonamides;

(g) thiol groups, which can be converted to disulfides or reacted with acyl halides, for example;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble or utilize the reactive cyanine analogue. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the disclosure encompasses both E and Z geometric isomers. Likewise, all tautomeric forms are also intended to be included.

Exemplary tertiary and quaternary zwitterionic lipids are synthesized by the route shown in Scheme A and Scheme B. Exemplary headgroups include propanoic acid linked to a 3° or 4° amine (DOPAT, DOPAQ), methylpropanoic acid linked to a 3° or 4° amine (DOMPAT, DOMPAQ), 4-methylbenzoic acid linked to a 3° or 4° amine (DOBAT, DOBAQ), and acetic acid linked to a 4° amine (DOAAQ). Exemplary lipids include ester linked dioleoyl tails.

Scheme A
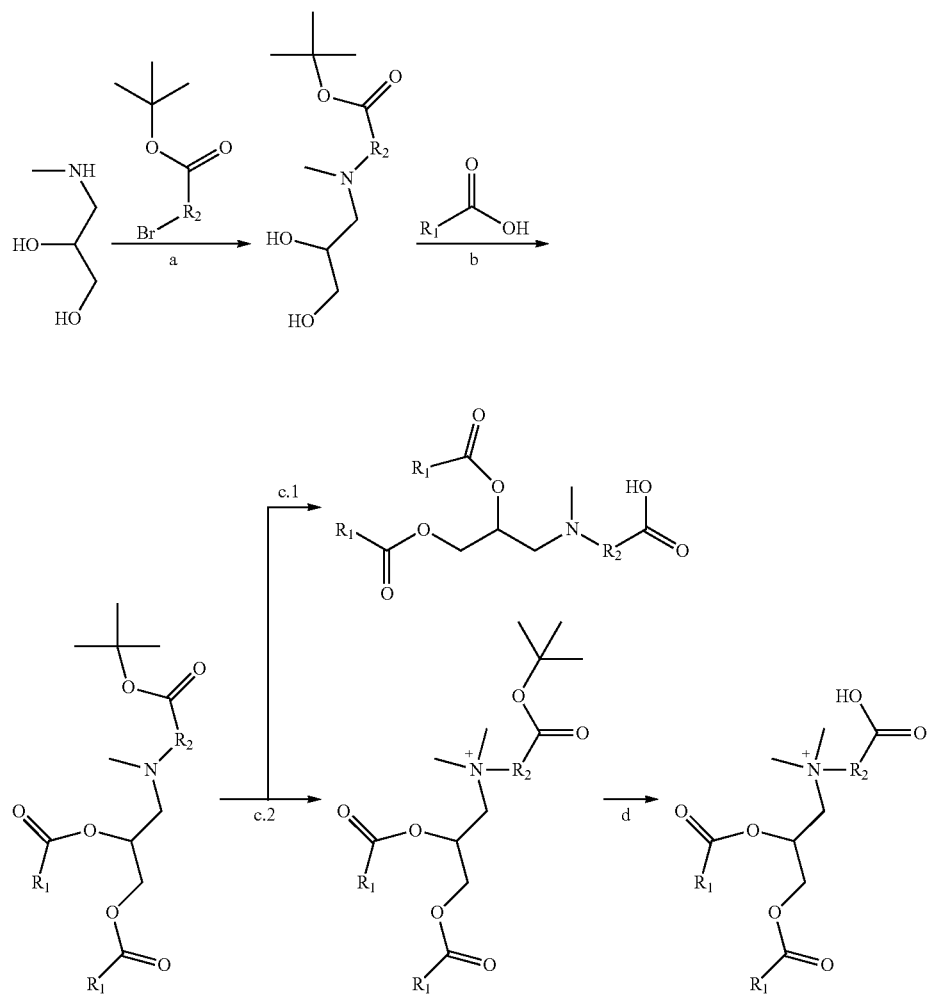
a) DIPEA (1.3 e), THF, 16 h, r.t. b) DCC (2.3 eq), DMAP (1 eq), CH$_2$Cl$_2$, 6 h, r.t.
c.1) TFA/TIPS/CH$_2$Cl$_2$ (4:1:5), 6 h, r.t. c.2) Dimethylsulfate (10 eq) Acetone, 48 h 4° C.
d) TFA/TIPS/CH$_2$Cl$_2$ (4:1:5), 6 h, r.t.
Scheme B
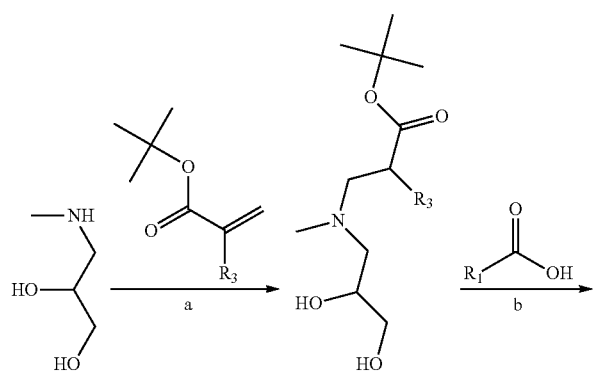

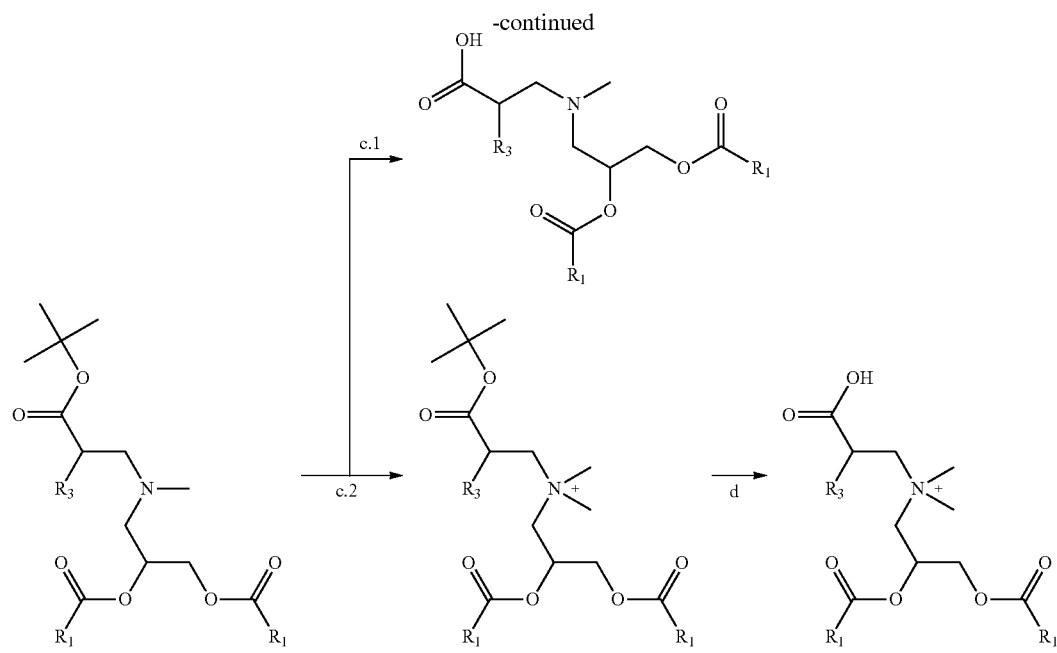
a) Neat, 24 h, 70° C. b) DCC (2.3 eq), DMAP (1 eq), CH$_2$Cl$_2$, 6 h, r.t.
c.1) TFA/TIPS/CH2Cl2 (4:1:5), 6 h, r.t. c.2) Dimethylsulfate (10 eq) Acetone, 48 h 4° C.
d) TFA/TIPS/CH$_2$Cl$_2$ (4:1:5), 6 h, r.t.
Exemplary lipids synthesized according to these schemes include: DOPAT, DOMPAT, DOBAT, DOPAQ, DOMPAQ, DOBAQ, DOAAQ, shown below. An exemplary R moiety is the acyl moiety derived from oleic acid.
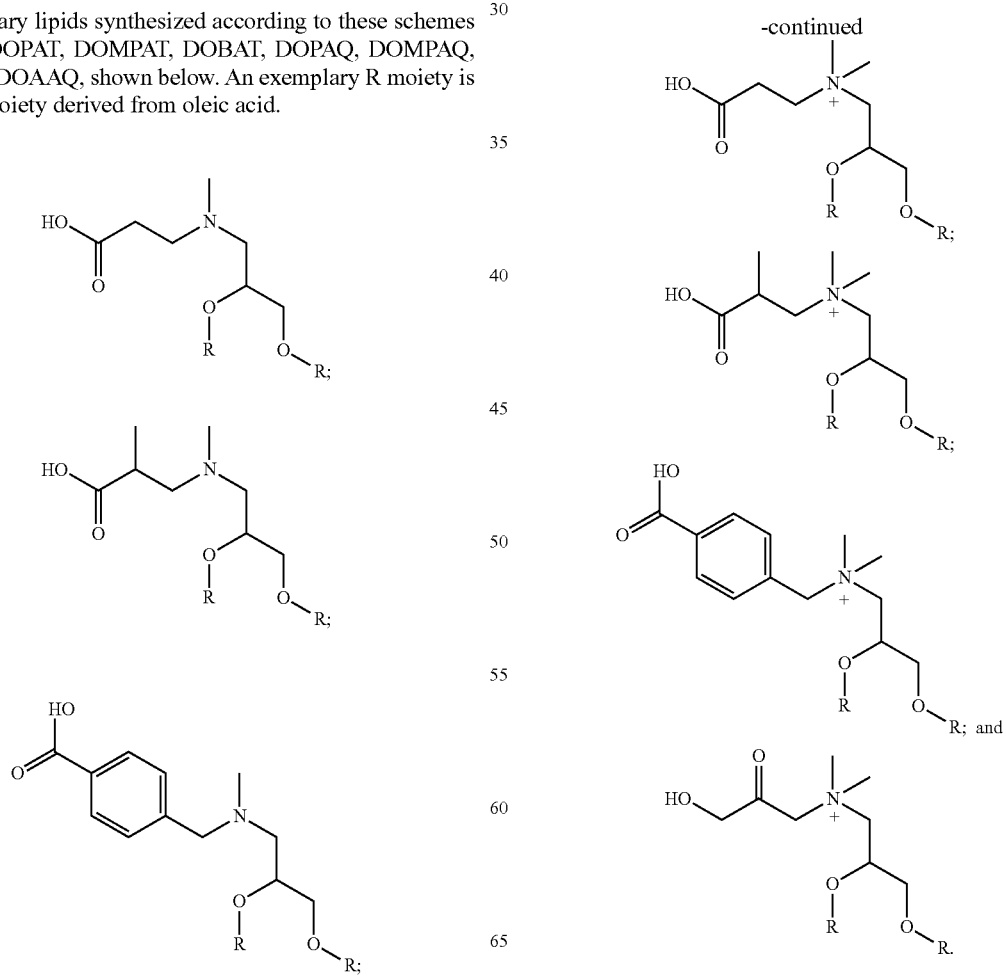

In the Schemes set forth below, the following symbols have the following meanings: $X^a$ and $X^b$ are independently any leaving group including but not limited to Br, Cl, I, OTs, OMs. $R^a$ is a linker moiety. $R^b$ and $R^c$ are independently selected from substituted or unsubstituted alkyl, or substituted or unsubstituted heteroalkyl. Exemplary groups include linear saturated or unsaturated chains, saturated or unsaturated branched chains and functionalized lipids. $R^d$ is any carbamate or amide. $R^e$ is any phosphate protecting group. [O] is any oxidizing agent. $R^f$ is any linear or cyclic substituted or unsubstituted alkyl group. $R^g$ is any useful moiety. $R^h$ and $R^i$ are independently any amine protecting group. $R^j$ is any functional group with an alkyl or heteroalkyl linker. $R^k$ is any carboxylate protecting group. $R^l$, $R^m$, $R^n$, $R^o$ is H or alkyl (e.g., Me).

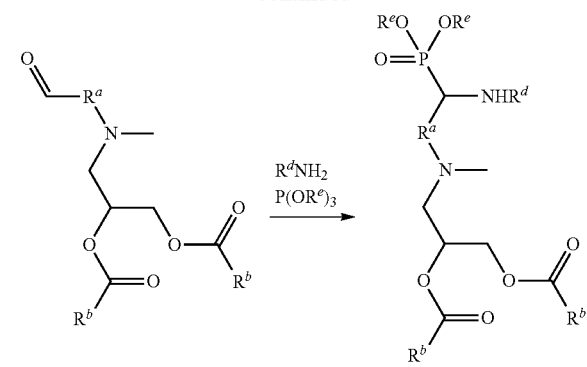

Scheme C: Synthesis of alpha-amino phosphonate dialkylamine

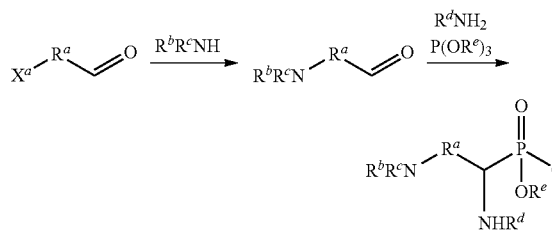

Scheme D: Synthesis of alpha-amino phosphonate

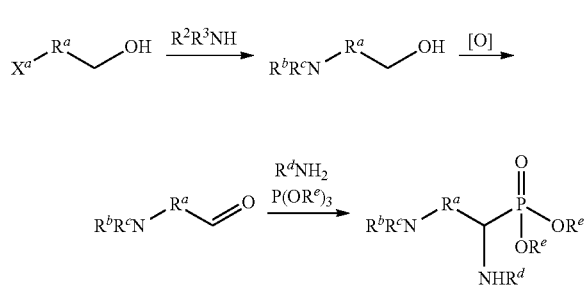

Scheme E: Synthesis of glyceryl-ester alpha-amino phosphonate

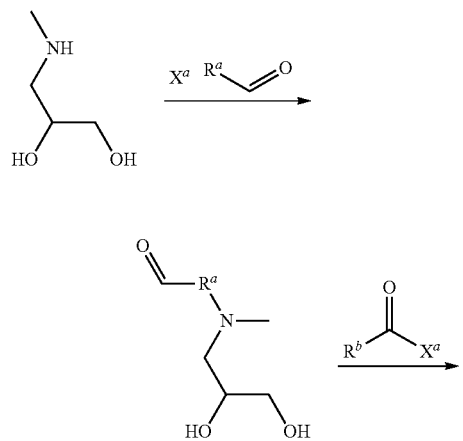

Scheme F: Synthesis of glyceryl-ether alpha-amino phosphonate

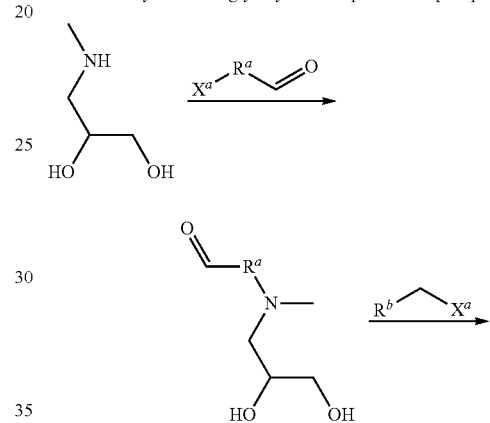

Scheme G: Synthesis of alpha-keto phosphonate dialkylamine

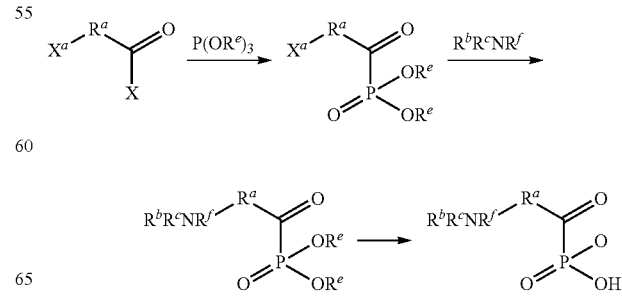

35
Scheme H: Synthesis of DETAPA dialkylamine
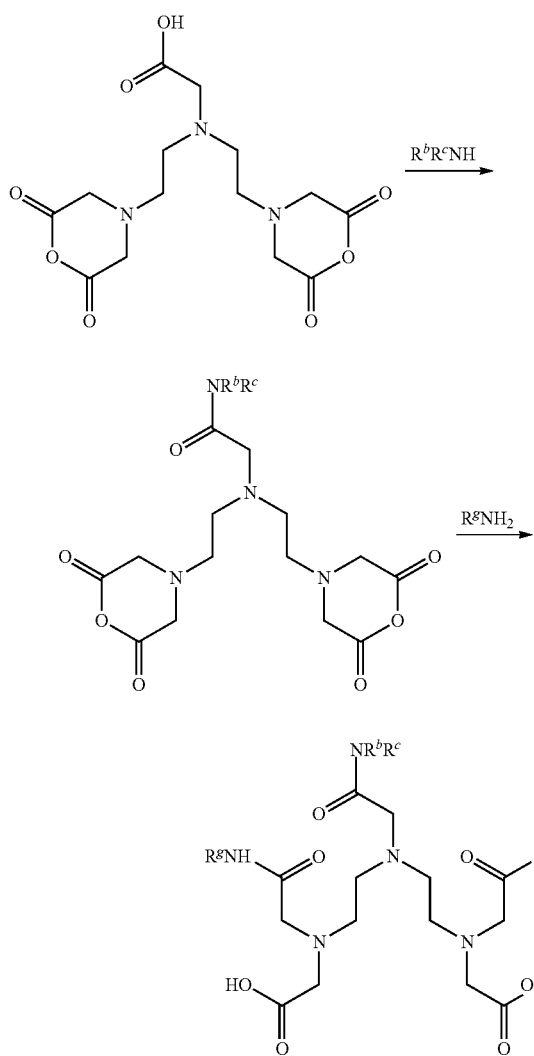
Scheme I: Synthesis of glyceryl-ester aminoethyl phosphonate
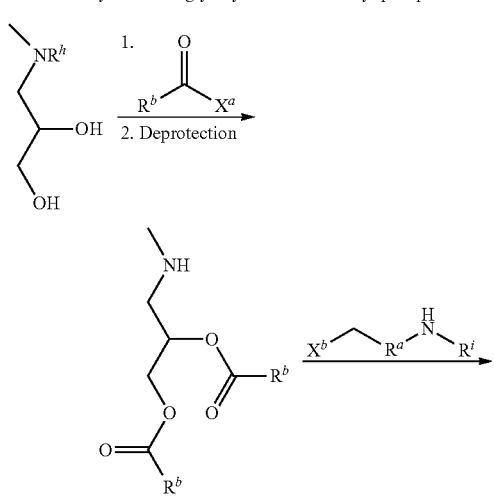
36
-continued
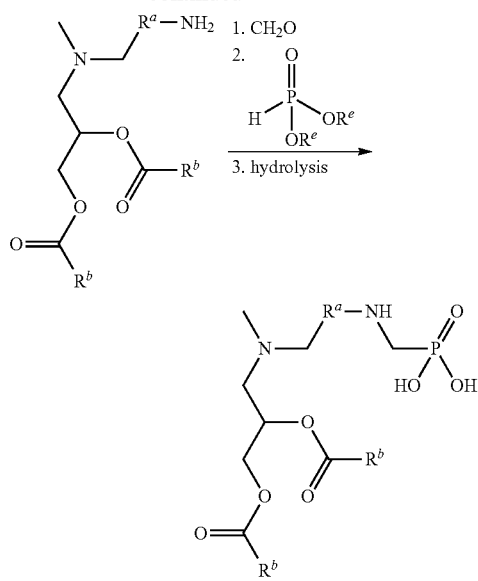
Scheme J: Synthesis of Glyceryl-ester aminomethyl phosphonate
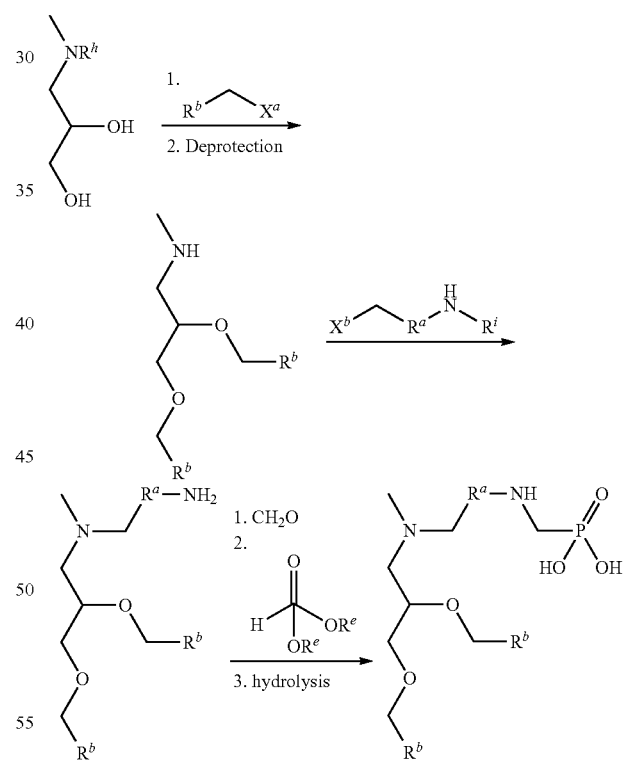
Scheme K: Synthesis of amino-acid lipids
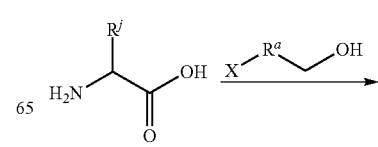

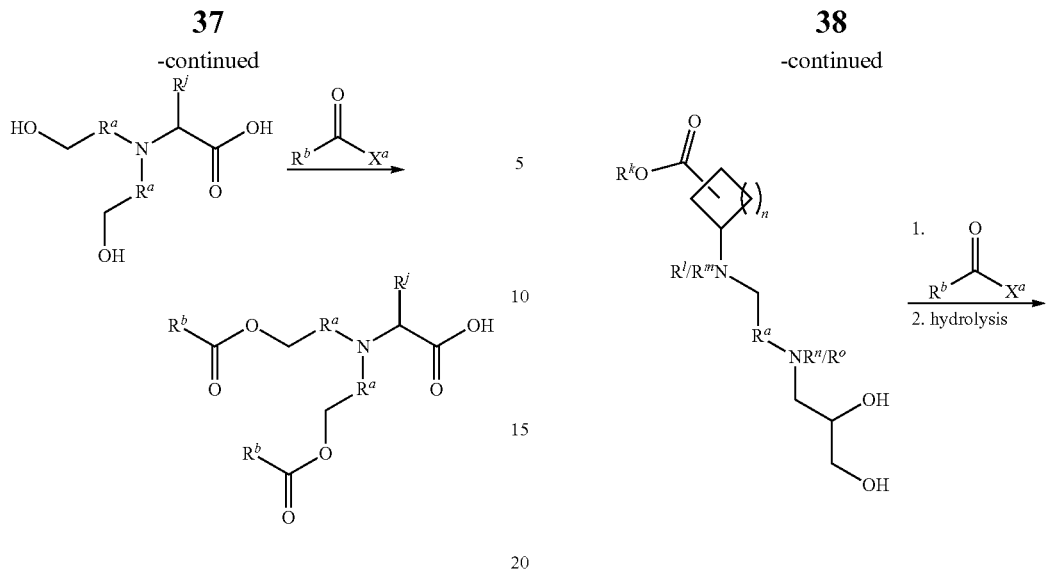
Scheme L: Synthesis of amino-acid ether lipids
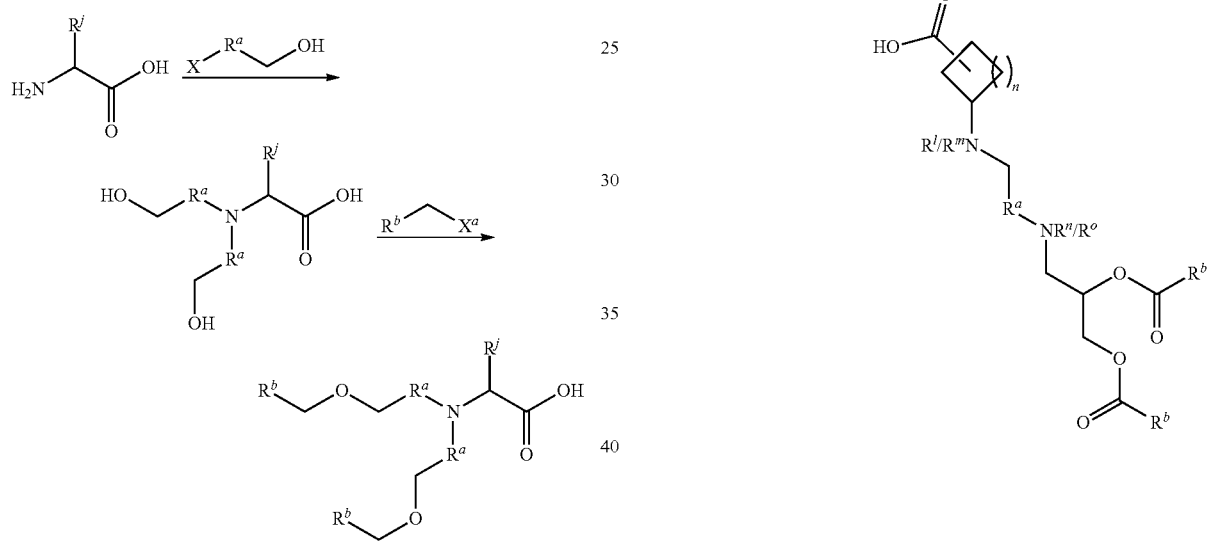
Scheme M: Synthesis of aminocyclocarboxylate double zwitter ester
Scheme N: Synthesis of aminocyclocarboxylate double zwitter ether
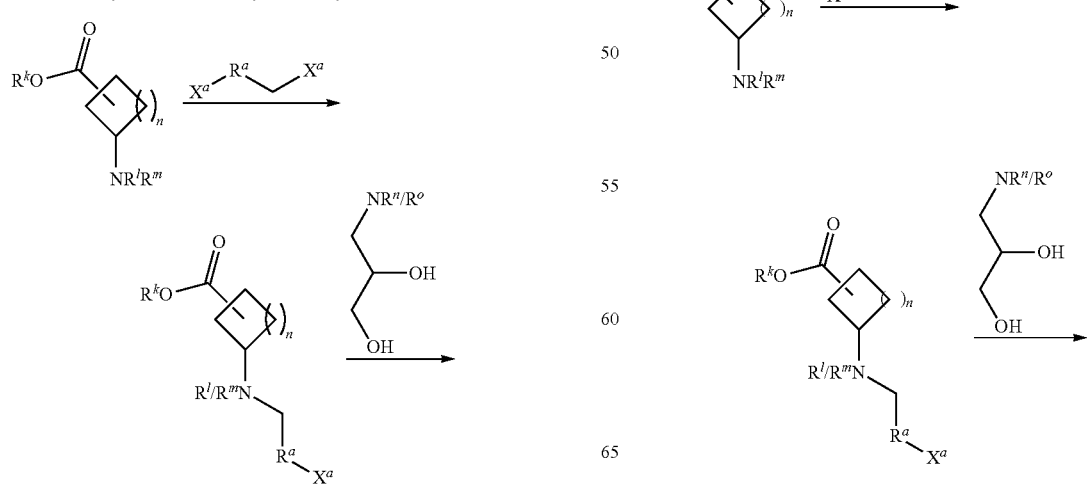

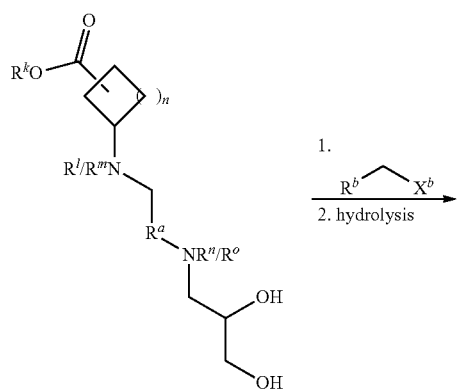
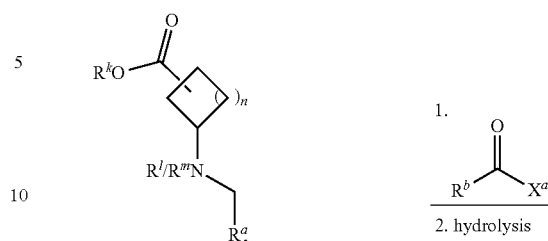
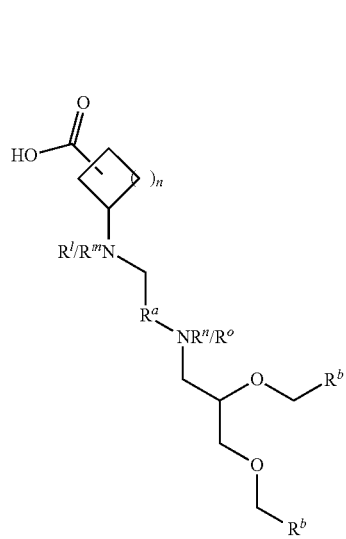
Scheme O: Synthesis of aminocyclocarboxylate double zwitter ketal
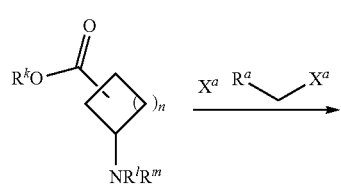
Scheme P: Synthesis of linear aminocarboxylate double zwitter ester
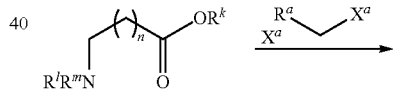
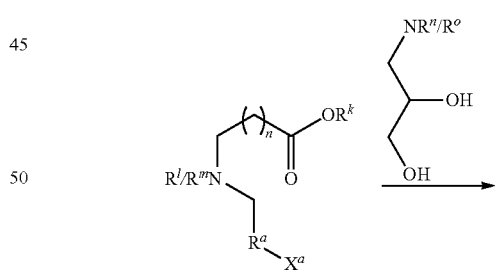
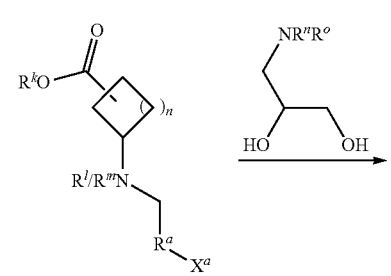
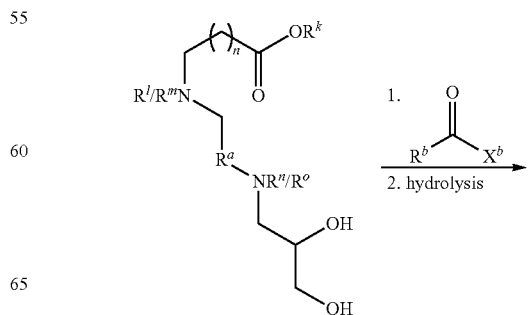

-continued
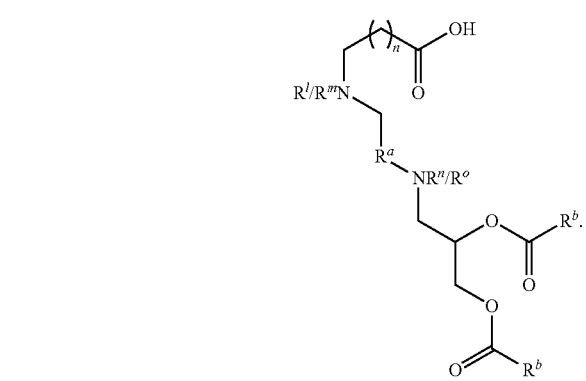
Scheme Q: Synthesis of linear carboxylate double zwitter ether
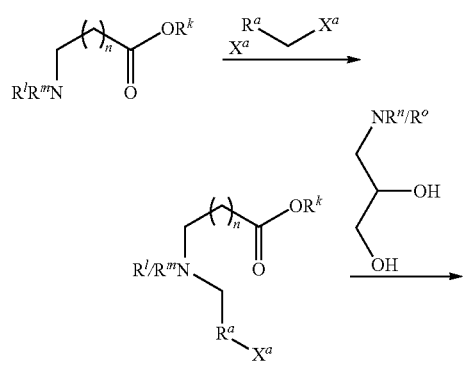
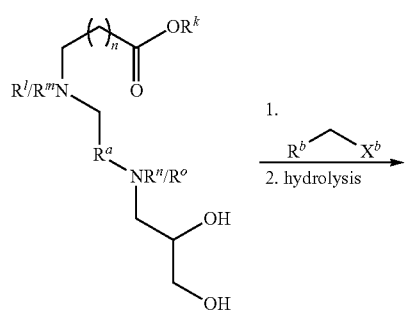
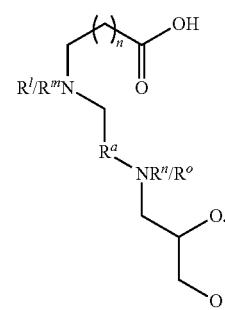
Scheme R: Synthesis of linear aminocarboxylate double zwitter ketal
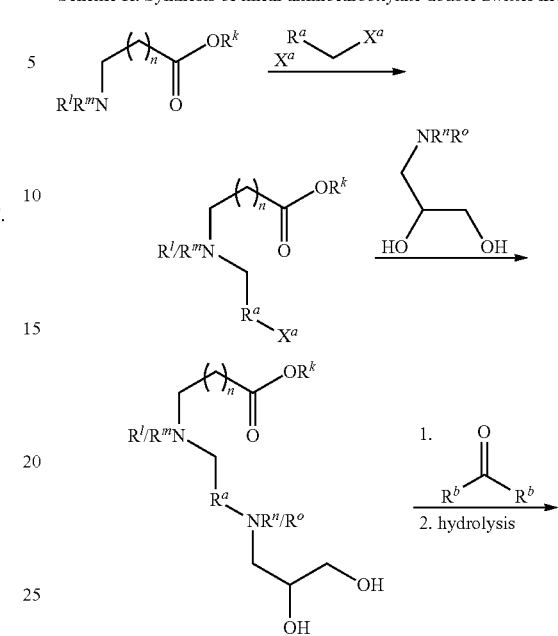
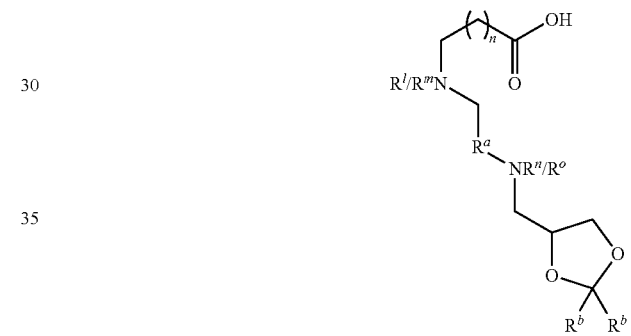
Scheme S: Synthesis of aminocyclocarboxylate double zwitter dialkylamine
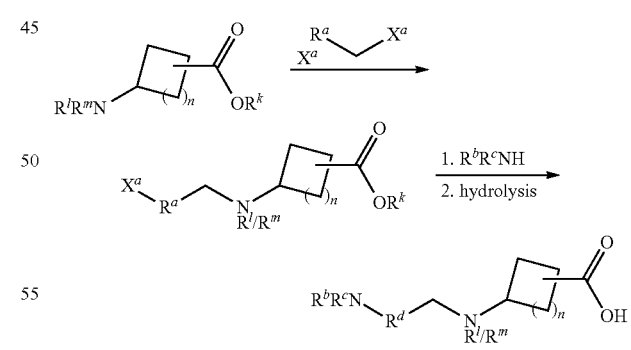
Scheme T: Synthesis of linear aminocyclocarboxylate double zwitter dialkylamine
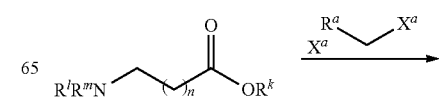

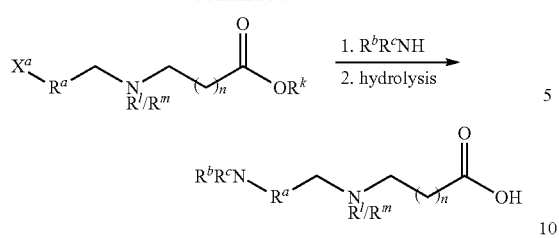
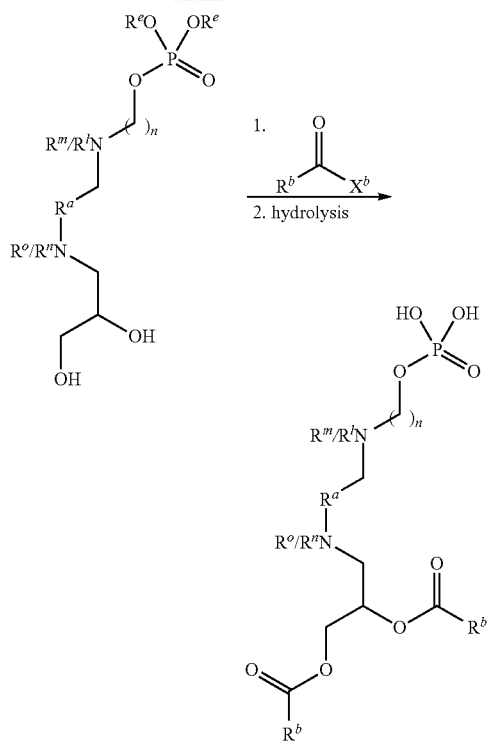
Scheme U: Synthesis of linear aminophosphate double zwitter dialkylamine
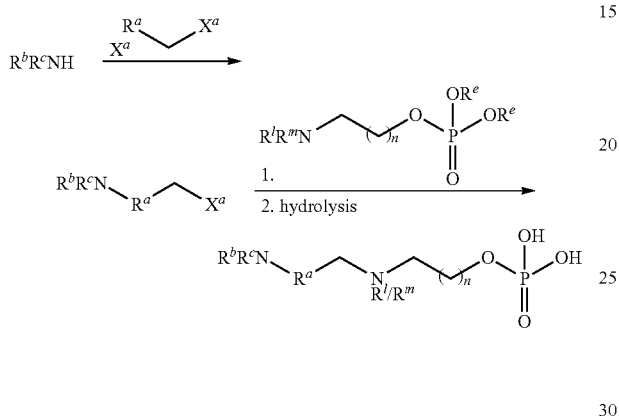
Scheme V: Synthesis of linear aminophosphonate double zwitter dialkylamine
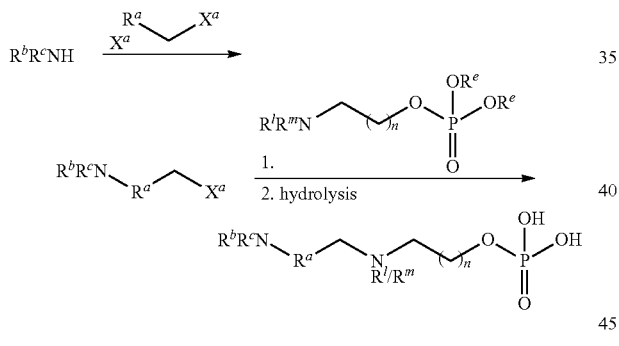
Scheme X: Synthesis of linear aminophosphate double zwitter ether
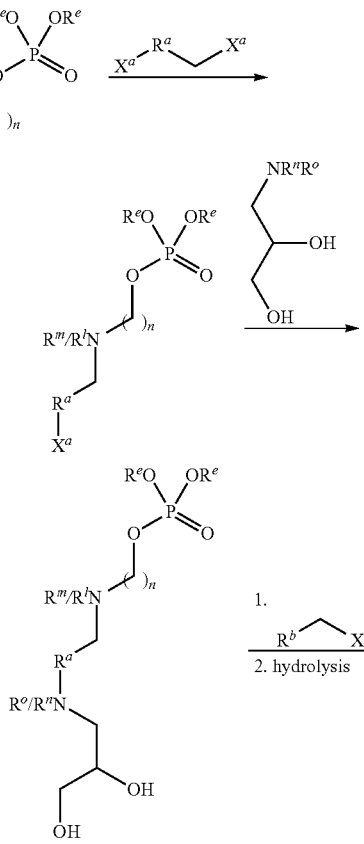
Scheme W: Synthesis of linear aminophosphate double zwitter ester
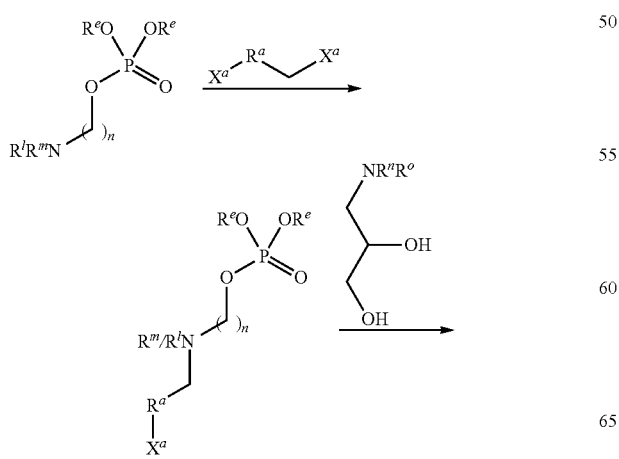

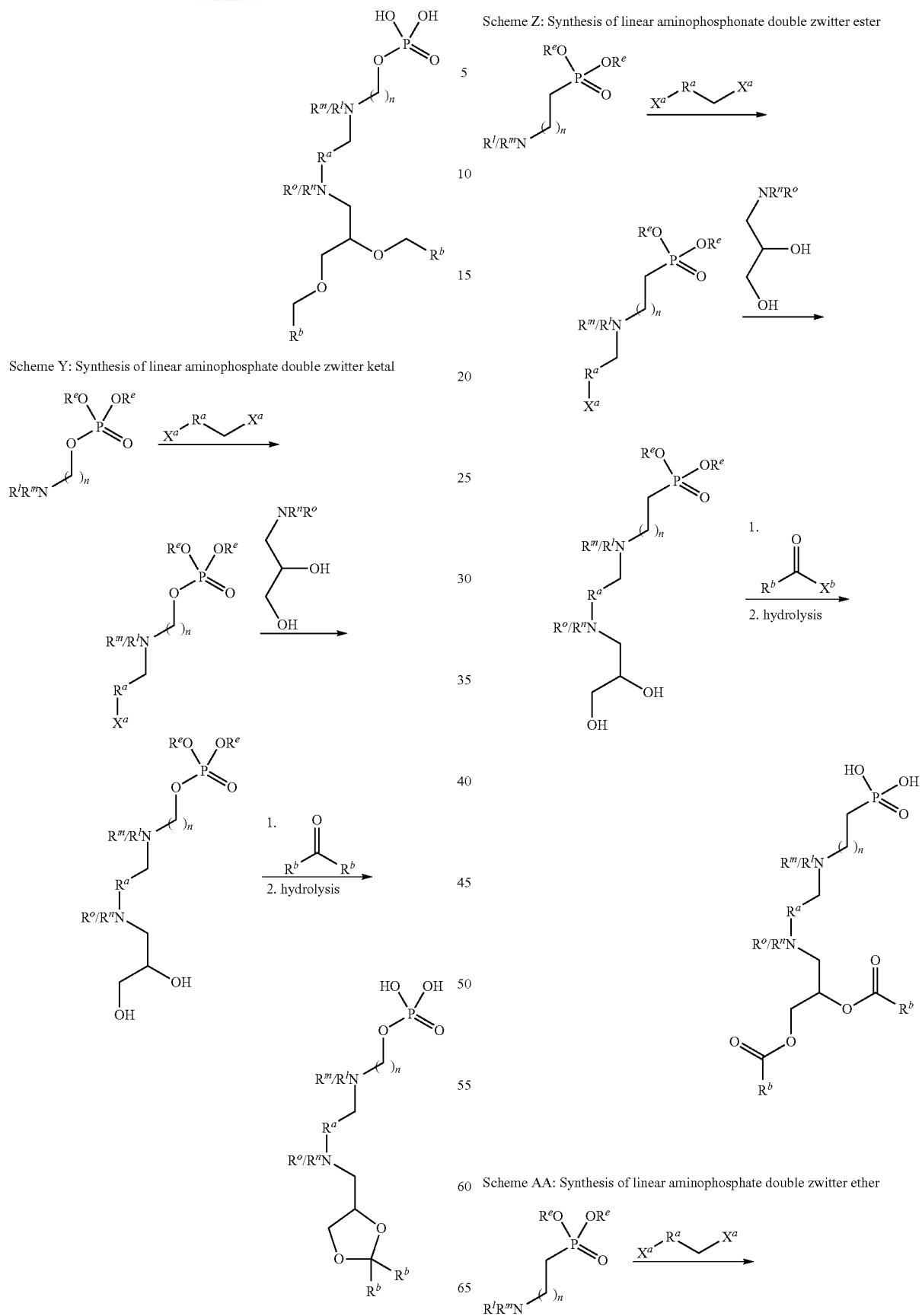

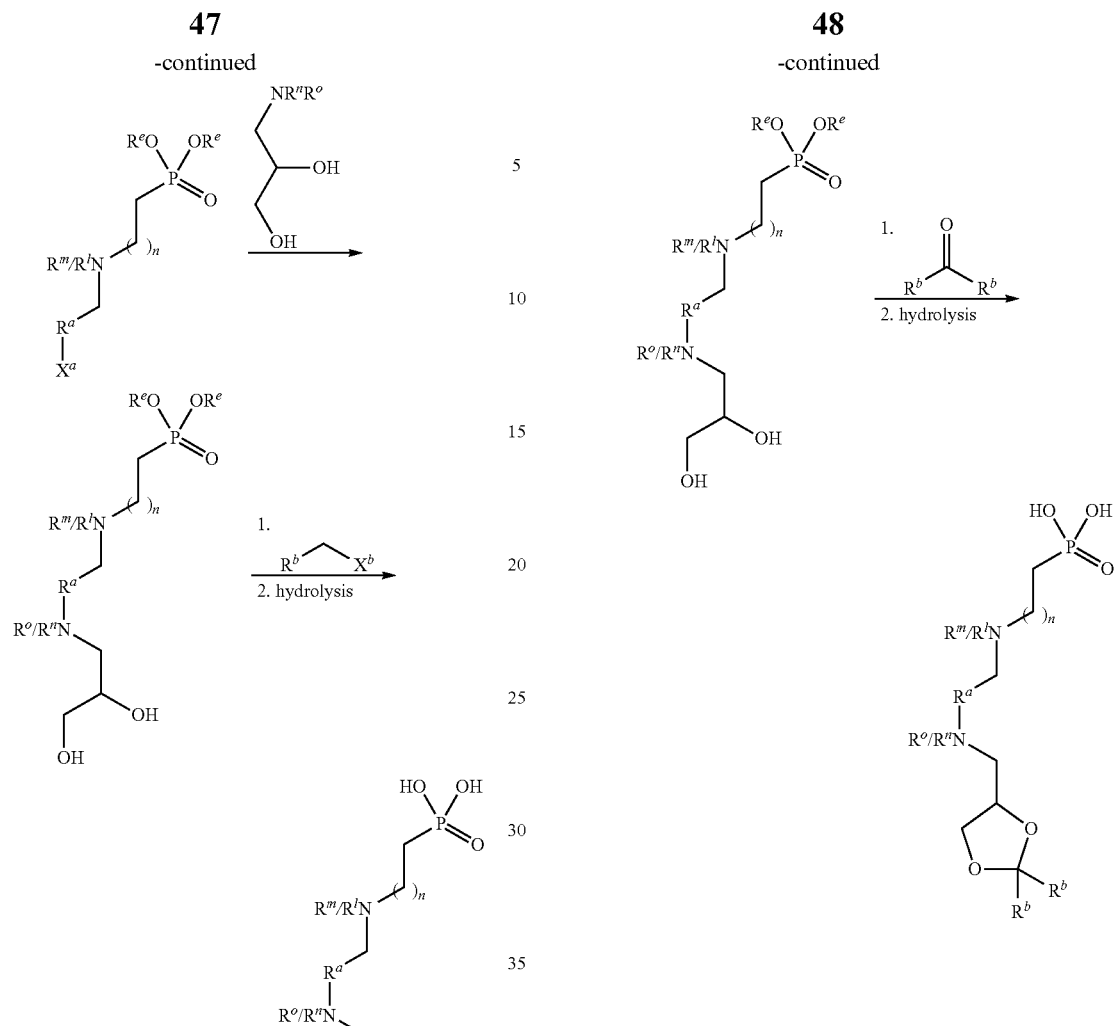
Scheme AB: Synthesis of linear aminophosphonate double zwitter ketal
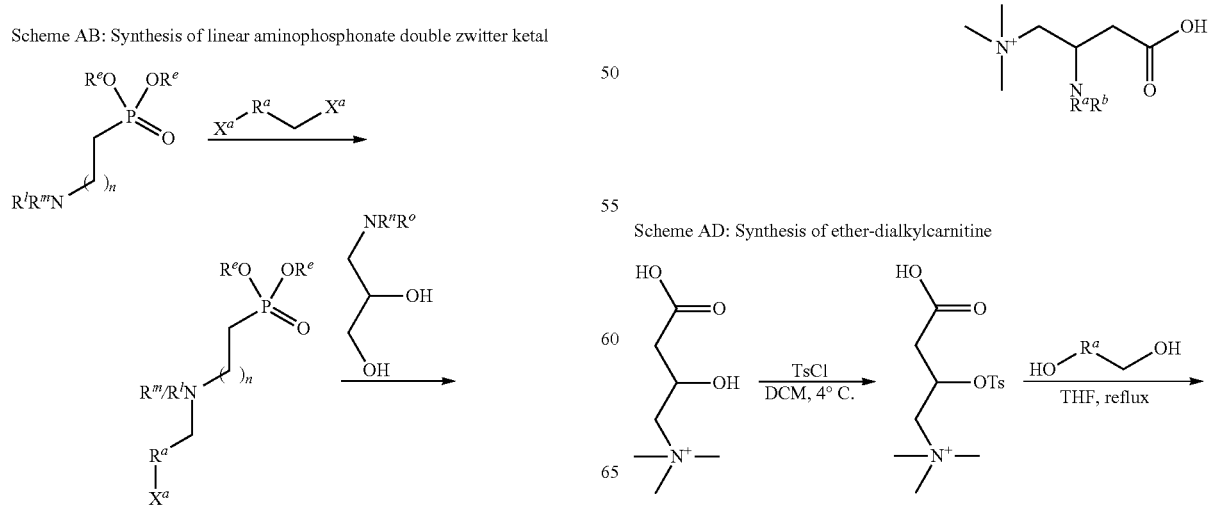
Scheme AC: Synthesis of dialkylcarnitine
Scheme AD: Synthesis of ether-dialkylcarnitine -continued

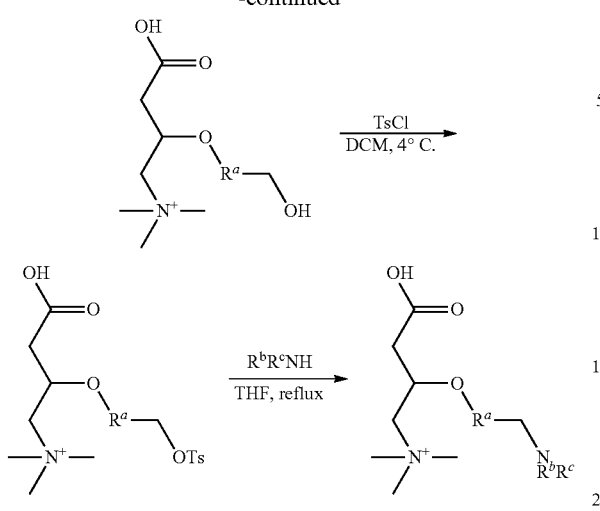

In each of the Schemes above, the carnitine-like structures below can be incorporated or used as precursors. When more than one cation is present, more than one of the carnitine-like structures can be incorporated in any combination.

Exemplary carnitine structures of the invention and of use in preparing compositions of the invention include:

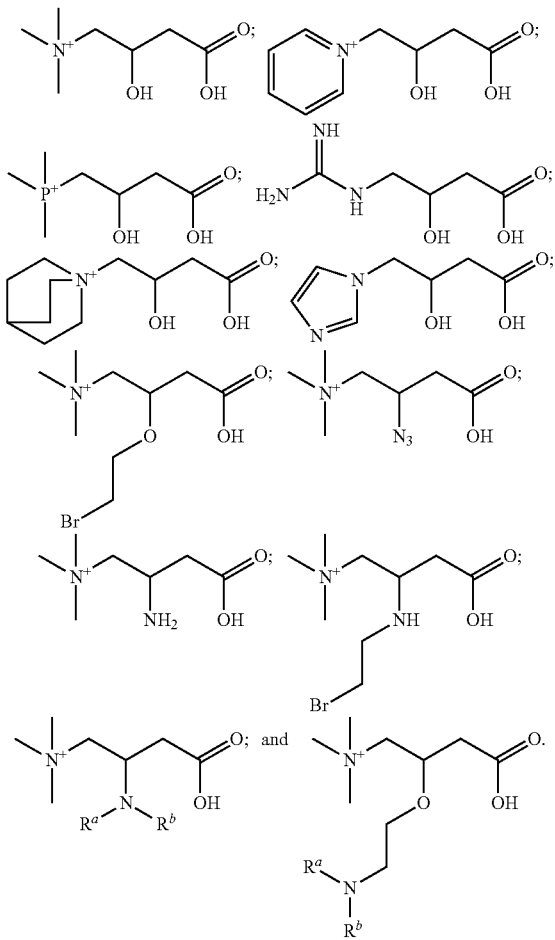

Exemplary components of the compounds shown in the Schemes above, include the structures shown below and homologues thereof, in any combination.

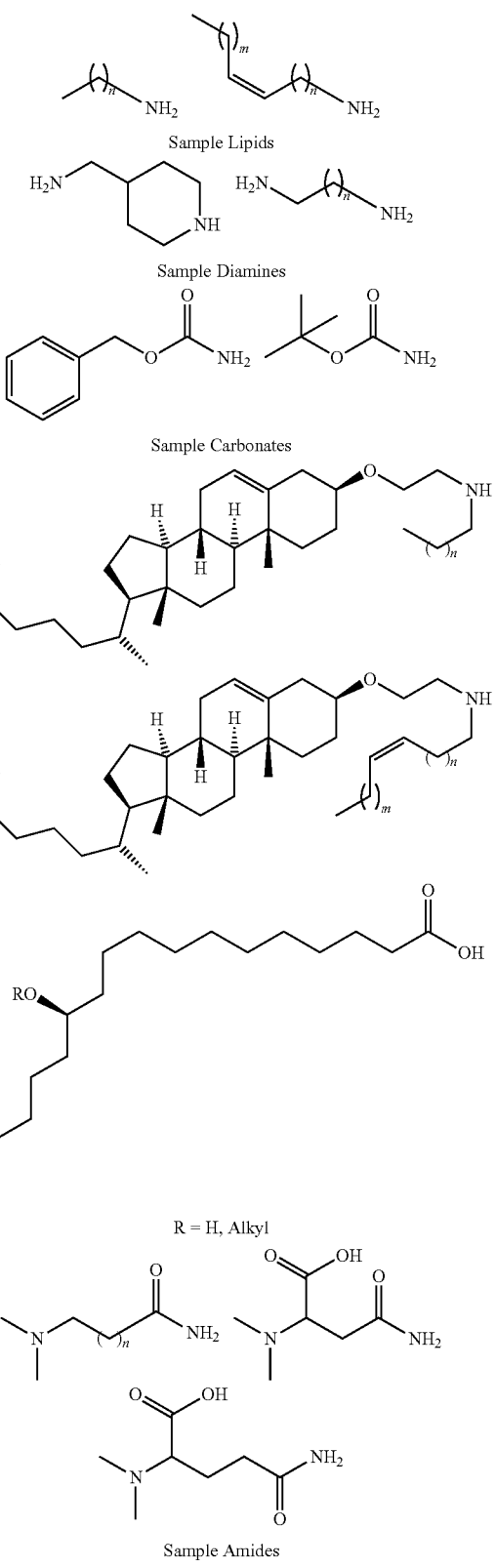

Encapsulants

In various embodiments, the present invention relates to the delivery of bioactive agents to cells. In exemplary embodiments, the invention relates to compounds, compositions and methods for delivering nucleic acids, polynucleotides, and oligonucleotides such RNA, DNA and analogs thereof, peptides, polypeptides, proteins, antibodies, hormones and small molecules, to cells by facilitating transport across cellular membranes in, for example, epithelial tissues and endothelial tissues. The compounds, compositions and methods of the invention are useful in therapeutic, research, and diagnostic applications that rely upon the efficient transfer of biologically active molecules into cells, tissues, and organs. The discussion is provided only for understanding of the invention that follows. This summary is not an admission that any of the work described below is prior art to the claimed invention.

Thus, in exemplary embodiments there is provided a composition comprising an encapsulator particle selected from the group consisting of liposomes, emulsions, micelles and lipidic bodies, wherein the encapsulator comprises the zwitterionic lipid.

In various embodiments, the zwitterionic lipids of the invention form disperse aqueous solutions of small bilayer structures. In exemplary embodiments, these structures are from about 30 to about 300 nm in diameter. These lipids encapsulate small molecules, proteins as well as nucleic acids either by themselves or as a component in a liposomal formulation.

In exemplary embodiments, the invention provides compounds, compositions, and methods to facilitate delivery of various molecules into a biological system, such as cells. The compounds, compositions, and methods provided by the instant invention can impart therapeutic activity by transferring bioactive (e.g., therapeutic, diagnostic) compounds across cellular membranes or across one or more layers of epithelial or endothelial tissue. The present invention encompasses the design and synthesis of novel zwitterionic lipids for the delivery of bioactive agents, including but not limited to small molecules, lipids, nucleosides, nucleotides, nucleic acids, polynucleotides, oligonucleotides, antibodies, toxins, negatively charged polymers and other polymers, for example proteins, peptides, hormones, carbohydrates, or polyamines, across cellular membranes.

Thus, according to various embodiments, there is provided an encapsulant (also referred to as an "encapsulator particle") of the invention comprising a bioactive agent encapsulated therein. The compounds, compositions, and methods of the invention can increase delivery or availability of biologically active molecules (e.g., siNAs, siRNAs, miRNAs, siRNA and miRNA inhibitors, nucleic acids, polynucleotides, oligonucleotides, peptides, polypeptides, proteins, hormones, antibodies, and small molecules) to cells or tissues compared to delivery of the molecules in the absence of the compounds, compositions, and methods of the invention. As such, the level of a biologically active molecule inside a cell, tissue, or organism is increased in the presence of the compounds and compositions of the invention compared to when the compounds and compositions of the invention are absent.

In an exemplary embodiment, the bioactive agent encapsulated in the encapsulant is a nucleic acid. Non-limiting examples of nucleic acids that can be delivered across cellular membranes using the compounds and methods of the invention include short interfering nucleic acids (siNA) (which includes siRNAs), antisense oligonucleotides, enzymatic nucleic acid molecules, 2',5'-oligoadenylates, triplex forming oligonucleotides, aptamers, and decoys. In general, the transporters described are designed to be used either individually or as part of a multi-component system, with or without degradable linkers. The compounds of the invention (generally shown in the Formulae below), when formulated into compositions, are expected to improve delivery of molecules into a number of cell types originating from different tissues, in the presence or absence of serum.

The compounds, compositions, and methods of the invention are useful for delivering biologically active molecules (e.g., siNAs, siRNAs, miRNAs, siRNA and miRNA inhibitors, nucleic acids, polynucleotides, oligonucleotides, peptides, polypeptides; proteins, hormones, antibodies, and small molecules) to cells or across epithelial and endothelial tissues, such as skin, mucous membranes, vasculature tissues, gastrointestinal tissues, blood brain barrier tissues, opthamological tissues, pulmonary tissues, liver tissues, cardiac tissues, kidney tissues etc. The compounds, compositions, and methods of the invention can be used both for delivery to a particular site of administration or for systemic delivery.

In an exemplary embodiment, the ratio of the negative charge on the nucleic acid to the positive charge on one or more cationic group on the zwitteronic lipid incorporated into the particle is at least 1 negative nucleic acid charge per 50 lipid positive charges.

The encapsulents of the invention can further comprise non-zwitterionic "helper lipids," which are positively charged, negatively charged or neutral. The helper lipids can be either natural structures or synthetic lipids. See, for example, FIGS. 17-31. Suitable natural lipids include phospholipids, including, for example, phosphoglycerides (including both acyl phosphoglycerides (such as, for example, phosphatidic acid, phosphatidyl ethanolamine, phosphatidyl serine, phosphatidyl inositol, phosphatidyl inositol phosphate, phosphatidyl inositol bisphosphate, phosphatidyl glycerol, diphosphatidylglycerol, and the like) and ether phosphoglycerides); glycosylglycerides (such as, for example, monogalactosyl diacylglycerol, digalactosyldiacylglycerol, sulphoquinovosyldiacylglycerol, dimannosyldiacylglycerol, galactofuranosyldiacylglycerol, galactosylglucosyldiacylglycerol, galactosylglucosyldiacylglycerol, glucosylgalactosylglucosyldiacylglycerol, and the like); sphingolipids (such as, for example, sphingosines, glycosyl ceramides, gangliosides, and the like); and saturated and unsaturated sterols (such as, for example, cholesterol, ergosterol, stigmasterol, sitosterol, and the like); and other like natural lipids.

Suitable synthetic lipid moieties can be derived from, for example, dipalmitoyl phosphotidylethanolamine (DMPE) (Genzyme Corp., Cambridge), DMRIE-C™ (GibcoBRL, Gaithersburg, Md.), 2,3-dioleyloxy-N-[2(spermine-carboxamido)ethyl]-N,N-dimethyl-1-propanamin-iumtrifluoroacetate (DOSPA) (Lipofectamine™, GibcoBRL, Gaithersburg, Md.), 3.beta.-[N—(N',N$^1$-dimethylaminoethyl)carbamoyl] cholesterol, Tfx-50 (Promega Corp., Madison, Wis.), N,N1, N2,N3-tetramethyl-N,N1,N2,N3-tetrapalmitylsperimine (TM-TPS) (Cellfectin, GibcoBRL, Gaithersburg, Md.), dipalmitoyl phosphatidylethanolaminospermine, and the like.

Exemplary encapsulants of the invention can further comprise one or more members selected from cholesterol or a cholesterol derivative, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-dioleoyl-3-dimethylammonium-propane (DODAP), 1,2-dioleoylcarbamyl-3-dimethylammonium-propane (DOCDAP), 1,2-dilineoyl-3-dimethylammonium-propane (DLINDAP), 3-dimethylamino-2-(cholest-5-en-3-beta-oxybutan-4-oxy)-1-(cis,cis-9,12-oc-tadecadienoxy) propane (CLinDMA), 2-[5'-(cholest-5-en-3-beta-oxy)-3'-oxapentoxy)-3-dimethyl-1-(cis,cis-9',1-2'-octadecadienoxy) propane (CpLin DMA), N,N-dimethyl-3,4-dioleyloxybenzylamine (DMOBA) and/or a mixture thereof. The non-zwitterionic lipid component can comprise dioleoylphosphatidylethanolamine (DOPE), palmitoyloleoylphosphatidylcholine (POPC), egg phosphatidylcholine (EPC), distearoylphosphatidylcholine (DSPC), cholesterol, and/or a mixture thereof. The PEG conjugate can comprise a PEG-dilaurylglycerol ($C_{12}$), a PEG-dimyristylglycerol ($C_{14}$), a PEG-dipalmitoylglycerol ($C_{16}$), a PEG-disterylglycerol ($C_{18}$), PEG-dilaurylglycamide ($C_{12}$), PEG-dimyristylglycamide ($C_{14}$), PEG-dipalmitoylglycamide ($C_{16}$), PEG-disterylglycamide ($C_{18}$), PEG-cholesterol, or PEG-DMB.

In various embodiments, the zwitterionic lipid component comprises from about 2% to about 100%, from about 5% to about 70%, from about 5% to about 45%, from about 5% to about 15%, or from about 40% to about 50% of the total lipid present in the formulation. In various embodiments, the zwitterionic lipid is 20%, 30%, 40%, 50% or more of the total lipid composition present in said particle. In exemplary embodiments, the lipid percent is computed on a mole percent basis that includes all of the lipid speies included in the formulation.

A variety of methods are available for preparing liposomes as described in, e.g., Szoka et al., *Ann. Rev. Biophys. Bioeng.* 9: 467 (1980); U.S. Pat. Nos. 4,186,183, 4,217,344, 4,235,871, 4,261,975, 4,485,054, 4,501,728, 4,774,085, 4,837,028, 4,946,787; PCT Publication No. WO 91/17424; Szoka & Papahadjopoulos, *Proc. Natl. Acad. Sci. USA* 75: 4194-4198 (1978); Deamer & Bangham, *Biochim. Biophys. Acta* 443: 629-634 (1976); Fraley et al., *Proc. Natl. Acad. Sci. USA* 76: 3348-3352 (1979); Hope et al., *Biochim. Biophys. Acta* 812: 55-65 (1985); Mayer et al., *Biochim. Biophys. Acta* 858: 161-168 (1986); Williams et al., *Proc. Natl. Acad. Sci. USA* 85: 242-246 (1988), Liposomes, ch. 1 (Ostro, ed., 1983); and Hope et al., *Chem. Phys. Lip.* 40: 89 (1986). Suitable methods include, e.g., sonication, extrusion, high pressure/homogenization, microfluidization, detergent dialysis, calcium-induced fusion of small liposome vesicles, and ether-infusion methods, all well known in the art.

In various embodiments, there is provided a serum-stable formulated molecular compositions that undergo a rapid pH-dependent phase transition. In an exemplary embodiment, the phase transition occurs when the encapsulant of the invention shifts from a neutral or basic milieu to a more acidic environment. In an exemplary embodiment, the phase transition results in at least a portion of an encapsulated bioactive agent being deposited in the cytosol of a cell. The lipids can also be used in formulations designed to release drugs and therapeutic agents in a low pH environment such as can occur in the interstial space of a tumor or site of inflammation in an animal such as a human.

The pH-dependent phase transition results in a structural change that increases the efficiency of delivery of a biologically active molecule, such as a polynucleotide, into a biological system, such as a cell. The structural change can increase the efficiency of delivery by, for example, increasing cell membrane fusion and release of a biologically active molecule into a biological system. Thus, in one embodiment, the serum-stable formulated molecular composition is stable in plasma or serum (i.e., in circulation) and stable at physiologic pH (i.e., about pH 7.4) and undergoes a rapid pH-dependent phase transition resulting in a structural change that increases the efficiency of delivery of a biologically active molecule into a biological system. In one embodiment, the pH dependent phase transition occurs at about pH 5 to about pH 8, e.g., from about pH 5.5 to about pH 7. In one embodiment, the serum-stable formulated molecular composition undergoes a structural change to adopt an inverted hexagonal structure at about pH 5.5 to about pH 8. For example, the serum-stable formulated molecular composition can transition from a stable lamellar structure adopted in circulation (i.e., in plasma or serum) at physiologic pH (about pH 7.4) to a less stable and more efficient delivery composition having an inverted hexagonal structure at the pH found in the early endosome. The serum-stable formulated molecular compositions that undergo a rapid pH-dependent phase transition demonstrate increased efficiency in the delivery of biologically active molecules due to their stability in circulation at physiologic pH and their ability to undergo a pH dependent structural change that increases cell membrane fusion and release of a biologically active molecule into a biological system, such as a cell.

The invention also provides methods for forming the encapsulants. In an exemplary embodiment, the method includes contacting a solution of a zwitterionic lipid of the invention in a low boiling organic solvent with an aqueous phase. The bioactive agent is dissolved in either the aqueous phase, the organic solvent or a combination thereof. In various embodiments, the zwitterionic lipid is dissolved in methanol. In an exemplary embodiment, the bioactive agent is dissolved in the aqueous phase. Control of the pH, the amount of organic solvent and zwitterionic lipid in the synthesis allows the preparation of encapsulants of a desired size and loaded with a desired amount of bioactive agent. See, for example, FIGS. 10-15.

Pharmaceutical Formulations

In an exemplary embodiment, the invention provides a pharmaceutical formulation including an encapsulant of the invention and a pharmaceutically acceptable carrier. In various embodiments, the encapsulant encapsulates a bioactive agent. The pharmaceutical formulation is preferably sterile. The pharmaceutical compositions of the present invention can be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension can include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

Once formed, the pharmaceutical formulations of the present invention are useful for the introduction of biologically active molecules into cells. Accordingly, the present invention also provides a pharmaceutical formulation appropriate for introducing a therapeutically or diagnostically effective amount of a bioactive molecule into a cell, subject or a cell of such subject. The methods are carried out in vitro or in vivo by first forming the pharmaceutical formulation as described above and then contacting the cell, subject or cell of the subject with a pharmaceutical formulation for period of time for transfer of the bioactive agent to occur. In an exemplary embodiment, the encapsulant encapsulates a nucleic acid and the contacting is for a period sufficient for transfection to occur.

The pharmaceutical formulations of the present invention can deliver an encapsulated bioactive agent to any cell type with which they are mixed or contacted. In exemplary embodiments, the formulations are endocytosed by a portion of the cells, exchange lipids with cell membranes, or fuse with the cells. Transfer or incorporation of the biologically active agent portion of the formulation can take place via any one of these, or other, pathways. In particular, when fusion takes place, the particle membrane is integrated into the cell membrane and the contents of the particle, i.e., bioactive agents, combine with the intracellular fluid, for example, the cytoplasm. The serum stable formulated molecular compositions that undergo pH-dependent phase transition demonstrate an increase in cell fusion at early endosomal pH, resulting in efficient delivery of the contents of the particle, i.e., bioactive agents, to the cell.

Assays known in the art can be used to assess the efficiency of delivery of the bioactive agent to the cell cytosol. For example, labeled derivatives of the bioactive agent can be detected by a number of means. Moreover, when the bioactive agent is a nucleic acid, and transfection occurs, transfection efficiency can be measured. Such assays allow one to determine quantitatively how each component of the encapsulant affects transfection efficacy, thereby optimizing the formulated molecular compositions or other lipid-based carrier systems.

It will be readily apparent to those of skill in the art that any reporter gene (e.g., luciferase, beta-galactosidase, green fluorescent protein, etc.) can be used in the assay. In addition, the lipid component (or, alternatively, the bioactive agent) can be labeled with any detectable label provided the does inhibit or interfere with uptake into the cell. Using such an assay, one of skill in the art can assess the impact of the various lipid components on cell uptake and transfection efficiencies, thereby optimizing the formulated composition.

Suitable labels for carrying out an assay include, but are not limited to, spectral labels, such as fluorescent dyes (e.g., fluorescein and derivatives, such as fluorescein isothiocyanate (FITC) and Oregon Green9; rhodamine and derivatives, such Texas red, tetrarhodimine isothiocynate (TRITC), etc., digoxigenin, biotin, phycoerythrin, AMCA, CyDyes, and the like; radiolabels, such as $^3$H, $^{125}$I, $^{35}$S, $^{14}$C, $^{32}$P, $^{33}$P, etc.; enzymes, such as horse radish peroxidase, alkaline phosphatase, etc.; spectral colorimetric labels, such as colloidal gold or colored glass or plastic beads, such as polystyrene, polypropylene, latex, etc. The label can be coupled directly or indirectly to a component of the formulated molecular composition using methods well known in the art. As indicated above, a wide variety of labels can be used, with the choice of label depending on sensitivity required, ease of conjugation with the formulated composition, stability requirements, and available instrumentation and disposal provisions.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

In exemplary embodiments, the pharmaceutical formulation includes a pharmaceutically effective dose, e.g., a therapeutically or diagnostically useful dose, of the bioactive agent. An exemplary pharmaceutically effective dose is that dose required to prevent, inhibit the occurrence, or treat (alleviate a symptom to some extent, preferably all of the symptoms) of a disease state, or to diagnose a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.0001 mg to about 7000 mg is a pharmaceutically effective dose. In exemplary embodiments, the pharmaceutical formulation includes a dose of 0.001 mg/kg and 100 mg/kg body weight/day of bioactive agent.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

The pharmaceutical formulations of the invention can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising an encapsulant of the invention and a pharmaceutically acceptable carrier. One or more encapsulants of the invention can be present in association with one or more non-toxic pharmaceutically acceptable carriers and/or diluents and/or adjuvants, and if desired other active ingredients.

The formulated molecular compositions of the present invention can also be administered to a subject in combination with other therapeutic compounds to increase the overall therapeutic effect. The use of multiple compounds to treat an indication can increase the beneficial effects while reducing the presence of side effects.

The following examples are offered to illustrate exemplary embodiments of the invention and are not limiting.

EXAMPLES

Example 1

DAPD Headgroup—General Synthesis—Benzyl Protected Headgroup

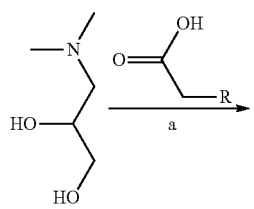

-continued

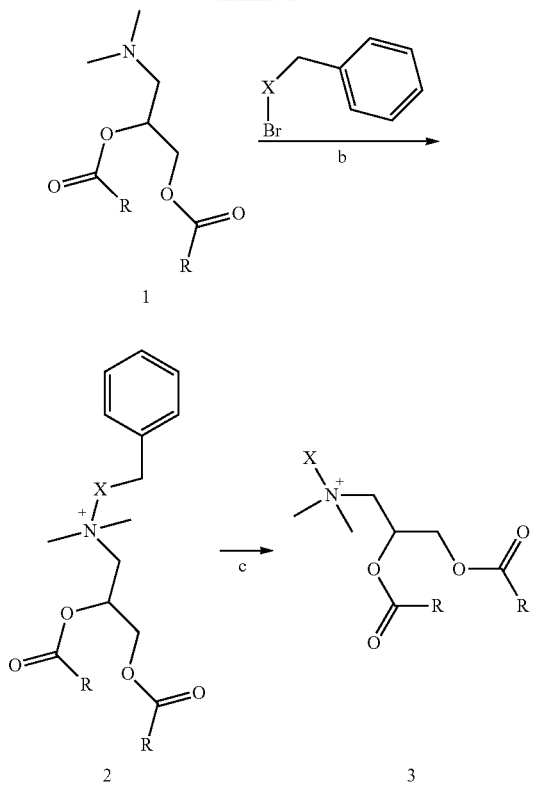

Synthesis of DAPD betaine-like lipid: a) DCC (2.3 equiv), DMAP (1 equiv), CH$_2$Cl$_2$, 6 h, r.t. b) THF, 3 days, 45° C. c) Pd (IV) on activated carbon (0.3 equiv), ammonium formate (6 equiv), methanol/water (9:1), 16 h, 35° C.

Synthesis of 1—Ester Linked Lipid Backbone. N,N-dimethylaminopropane-1,2-diol was combined with the desired R-acid (2.2 eq.), N,N-dicyclohexylcarbodiimide (2.3 eq.) and 4-mimethylaminopyridine (1 eq.) in anhydrous dichloromethane. The reaction was stirred at room temperature for 4 h. Solvents were evaporated under reduced pressure at 60° C., and the concentrated oil was redissolved in 2:1 CHCl$_3$:MeOH and washed 2× with 1M HCl. The product was then purified by HPFC. Yield is generally 70-85% with respect to N,N-dimethylaminopropane-1,2-diol.

Synthesis of 2—Protected Betaine-like Lipid. To a solution of 1 in tetrahyrofuran was added the desired benzyl ester protected acid head group (1.3 eq.). The reaction was stirred at 45° C. for 72 h. The solvent was removed by evaporation under reduced pressure at 60° C., and the concentrated reaction was purified by HPFC. Yield is generally 45-60% with respect to 1.

Synthesis of 3—Deprotected Betaine-like Lipid. To a solution of 2 in MeOH under nitrogen were added 10% Pd/C and ammonium formate (6 eq.) solution in water sequentially. The reaction was stirred vigorously overnight under nitrogen at 35° C. Pd/C was filtered off over Celite, and solvent was evaporated under reduced pressure at 60° C. The product was purified by HPFC. Yield is generally 75-90% with respect to 2.

Example 2

DAPD Headgroup—General Synthesis—t-butyl Protected Headgroup

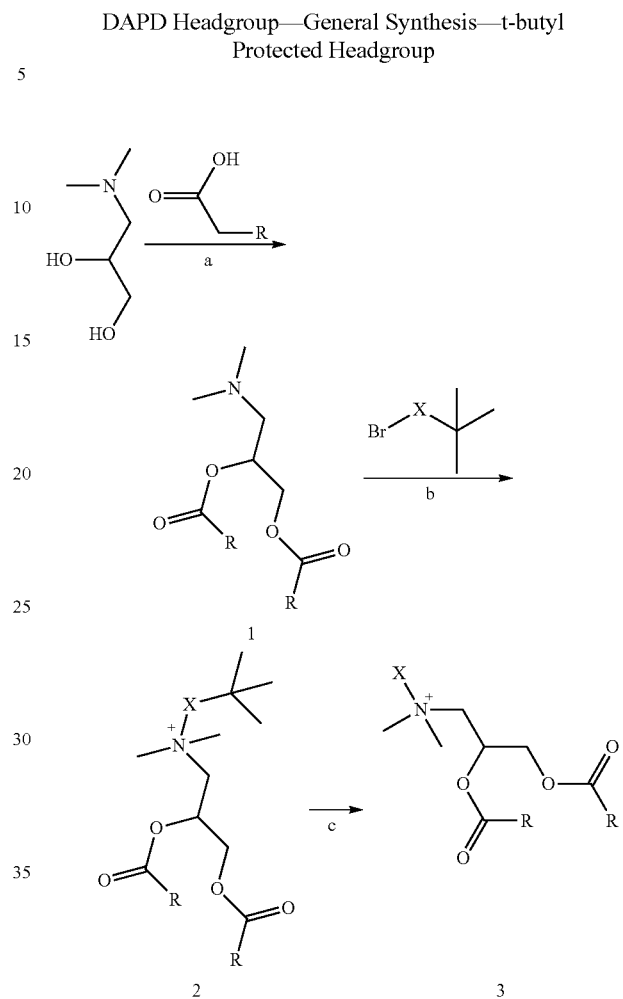

Synthesis of DAPD betaine-like lipid: a) DCC (2.3 equiv), DMAP (1 equiv), CH$_2$Cl$_2$, 6 h, r.t. b) THF, 3 days, 45° C. c) TFA/triisopropylsilane/CH$_2$Cl$_2$ (4:1:5), 6 h, r.t.

Synthesis of 1—Ester Linked Lipid Backbone. N,N-dimethylaminopropane-1,2-diol was combined with the desired R-acid (2.2 eq.), N,N-dicyclohexylcarbodiimide (2.3 eq.) and 4-dimethylaminopyridine (1 eq.) in anhydrous dichloromethane. The reaction was stirred at room temperature for 4 hrs. Solvents were evaporated under reduced pressure at 60° C., and the concentrated oil was redissolved in 2:1 CHCl$_3$:MeOH and washed 2× with 1M HCl. The product was then purified by HPFC. Yield is generally 70-85% with respect to N,N-dimethylaminopropane-1,2-diol.

Synthesis of 2—Protected Betaine-like Lipid. To a solution of 1 in tetrahyrofuran was added the desired t-butyl protected acid head group (1.3 eq.). The reaction was stirred at 45° C. for 72 h. The solvent was removed by evaporation under reduced pressure at 60° C., and the concentrated reaction was purified by HPFC. Yield is generally 45-60% with respect to 1.

Synthesis of 3—Deprotected Betaine-like Lipid. To a solution of 2 in dichloromethane were added 40% (v:v) trifluoroacetic acid and 10% (v:v) triisopropylsilane. The reaction was stirred at room temperature for 6 h. Solvent was evaporated under reduced pressure at 60° C. The product was purified by HPFC. Yield is generally 85-90% with respect to 2.

Example 3

DMAE Headgroup—General Synthesis—Benzyl Protected Headgroup

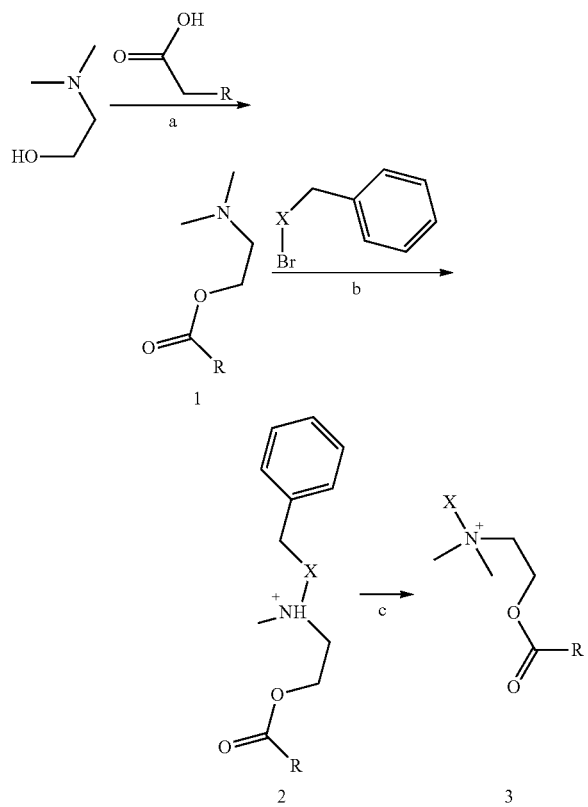

Synthesis of DMAE betaine-like lipid: a) DCC (1.2 equiv), DMAP (0.5 equiv), CH$_2$Cl$_2$, 6 h, r.t. b) THF, 3 days, 45° C. c) Pd (IV) on activated carbon (0.3 equiv), ammonium formate (6 equiv), methanol/water (9:1), 16 h, 35° C.

Synthesis of 1—Ester Linked Lipid Backbone. N,N-dimethylaminoethanol was combined with the desired R-acid (1.1 eq.), N,N-dDicyclohexylcarbodiimide (1.2 eq.) and 4-dimethylaminopyridine (0.5 eq.) in anhydrous dichloromethane. The reaction was stirred at room temperature for 4 h. Solvents were evaporated under reduced pressure at 60° C., and the concentrated oil was redissolved in 2:1 CHCl$_3$:MeOH and washed 2× with 1M HCl. The product was then purified by HPFC. Yield is generally 70-85% with respect to N,N-dimethylaminoethanol.

Synthesis of 2—Protected Betaine-like Lipid. To a solution of 1 in tetrahyrofufan was added the desired benzyl ester protected acid head group (1.3 eq.). The reaction was stirred at 45° C. for 72 h. The solvent was removed by evaporation under reduced pressure at 60° C., and the concentrated reaction was purified by HPFC. Yield is generally 45-60% with respect to 1.

Synthesis of 3—Deprotected Betaine-like Lipid. To a solution of 2 in MeOH under nitrogen were added 10% Pd/C and ammonium formate (6 eq.) solution in water sequentially. The reaction was stirred vigorously overnight under nitrogen at 35° C. Pd/C was filtered off over Celite, and solvent was evaporated under reduced pressure at 60° C. The product was purified by HPFC. Yield is generally 75-90% with respect to 2.

Example 4

DMAE Headgroup—General Synthesis—t-butyl Protected Headgroup

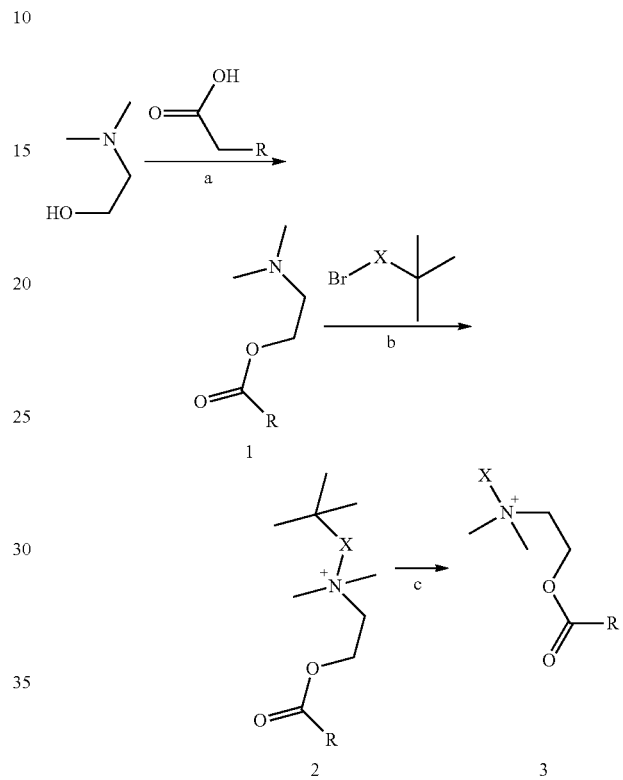

Synthesis of DMAE betaine-like lipid: a) DCC (1.2 equiv), DMAP (0.5 equiv), CH$_2$Cl$_2$, 6 h, r.t. b) THF, 3 days, 45° C. c) TFA/triisopropylsilane/CH$_2$Cl$_2$ (4:1:5), 6 h, r.t.

Synthesis of 1—Ester Linked Lipid Backbone. N,N-dimethylaminoethanol was combined with the desired R-acid (1.1 eq.), N,N-dicyclohexylcarbodiimide (1.2 equivalents) and 4-dimethylaminopyridine (0.5 equivalents) in anhydrous dichloromethane. The reaction was stirred at room temperature for 4 h. Solvents were evaporated under reduced pressure at 60° C., and the concentrated oil was redissolved in 2:1 CHCl$_3$:MeOH and washed 2× with 1M HCl. The product was then purified by HPFC. Yield is generally 70-85% with respect to N,N-dimethylaminoethanol.

Synthesis of 2—Protected Betaine-like Lipid. To a solution of 1 in tetrahyrofuran was added the desired t-butyl protected acid head group (1.3 eq.). The reaction was stirred at 45° C. for 72 h. The solvent was removed by evaporation under reduced pressure at 60° C., and the concentrated reaction was purified by HPFC. Yield is generally 45-60% with respect to 1.

Synthesis of 3—Deprotected Betaine-like Lipid. To a solution of 2 in dichloromethane were added 40% (v:v) trifluoroacetic acid and 10% (v:v) triisopropylsilane. The reaction was stirred at room temperature for 6 hrs. Solvent was evaporated under reduced pressure at 60° C. The product was purified by HPFC. Yield is generally 85-90% with respect to 2.

Example 5

MAPD Headgroup—General Synthesis—Benzyl Protected Headgroup

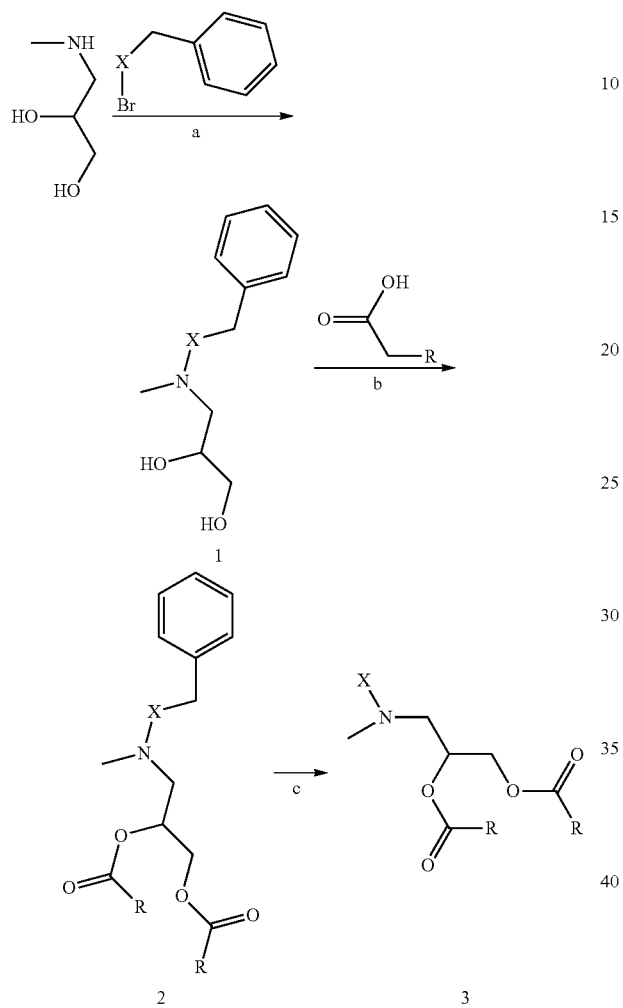

Synthesis of MAPD betaine-like lipid: a) DIPEA (1.3 equivalents), THF, 16 h, r.t. b) DCC (2.3 equiv), DMAP (1 equiv), CH₂Cl₂, 6 h, r.t. c) Pd (IV) on activated carbon (0.3 equiv), ammonium formate (6 equiv), methanol/water (9:1), 16 h, 35° C.

Synthesis of 1—Protected Betaine-like Lipid Head Group. N-methylaminopropane-1,2-diol was combined with the desired benzyl ester protected acid head group (1.3 eq) and N,N-diisopropylethylamine (1.3 eq.) in tetrahydrofuran. The reaction was stirred at room temperature for 16 h, forming a white DIPEA salt. The salt was removed by filtration and discarded. The solvent and excess DIPEA were removed by evaporation under reduced pressure at 60° C., and the crude reaction mixture was used in the next step. Yield is generally 85-90% with respect to N-methylaminopropane-1,2-diol.

Synthesis of 2—Protected Betaine-like Lipid. To a solution of 1 in anhydrous dichloromethane was added the desired R-acid (2.2 eq.), N,N-dicyclohexylcarbodiimide (2.3 eq.) and 4-dimethylaminopyridine (1 eq.). The reaction was stirred at room temperature for 4 hrs. Solvents were evaporated under reduced pressure at 60° C., and the concentrated oil was redissolved in 2:1 CHCl₃:MeOH and washed 2× with 1M HCl. The product was then purified by HPFC. Yield is generally 75% with respect to 1.

Synthesis of 3—Deprotected Betaine-like Lipid. To a solution of 2 in MeOH under nitrogen were added 10% Pd/C and ammonium formate (6 eq.) solution in water sequentially. The reaction was stirred vigorously overnight under nitrogen at 35° C. Pd/C was filtered off over Celite, and solvent was evaporated under reduced pressure at 60° C. The product was purified by HPFC. Yield is generally 75-90% with respect to 2.

Example 6

MAPD Headgroup—General Synthesis—t-butyl Protected Headgroup

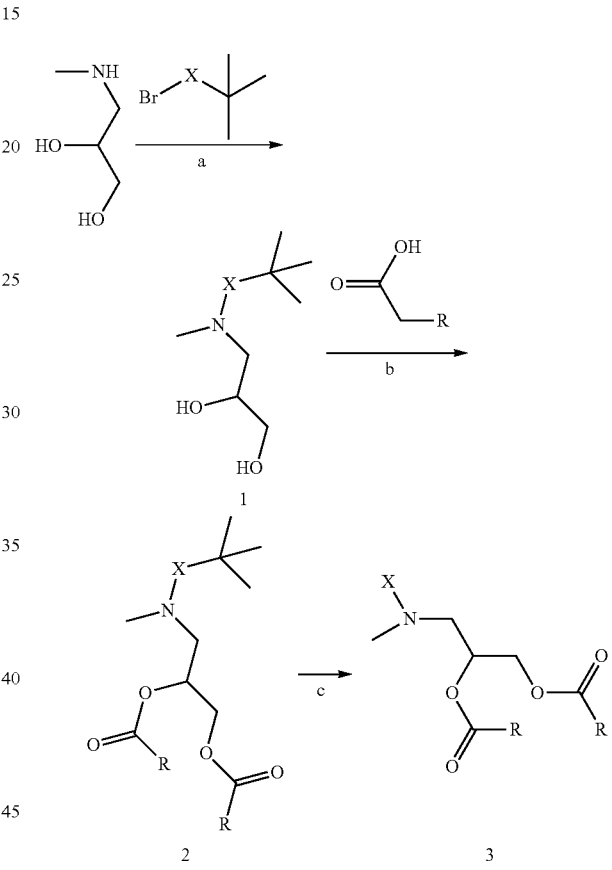

Synthesis of MAPD betaine-like lipid: a) DIPEA (1.3 equivalents), THF, 16 h, r.t. b) DCC (2.3 equiv), DMAP (1 equiv), CH₂Cl₂, 6 h, r.t. c) TFA/triisopropylsilane/CH₂Cl₂ (4:1:5), 6 h, r.t.

Synthesis of 1—Protected Betaine-like Lipid Head Group. N-methylaminopropane-1,2-diol was combined with the desired t-butyl protected acid head group (1.3 eq.) and N,N-diisopropylethylamine (1.3 eq.) in tetrahydrofuran. The reaction was stirred at room temperature for 16 h, forming a white DIPEA salt. The salt was removed by filtration and discarded. The solvent and excess DIPEA were removed by evaporation under reduced pressure at 60° C., and the crude reaction mixture was used in the next step. Yield is generally 85-90% with respect to N-methylaminopropane-1,2-diol.

Synthesis of 2—Protected Betaine-like Lipid. To a solution of 1 in anhydrous dichloromethane was added the desired R-acid (2.2 eq.), N,N-dicyclohexylcarbodiimide (2.3 eq.) and 4-dimethylaminopyridine (1 eq.). The reaction was stirred at room temperature for 4 h. Solvents were evaporated under reduced pressure at 60° C., and the concentrated oil was redissolved in 2:1 CHCl₃:MeOH and washed 2× with 1M HCl. The product was then purified by HPFC. Yield is generally 75% with respect to 1.

Synthesis of 3—Deprotected Betaine-like Lipid. To a solution of 2 in dichloromethane were added 40% (v:v) trifluoroacetic acid and 10% (v:v) triisopropylsilane. The reaction was stirred at room temperature for 6 hrs. Solvent was evaporated under reduced pressure at 60° C. The product was purified by HPFC. Yield is generally 85-90% with respect to 2.

Example 7

Guanidino Lipid Synthesis

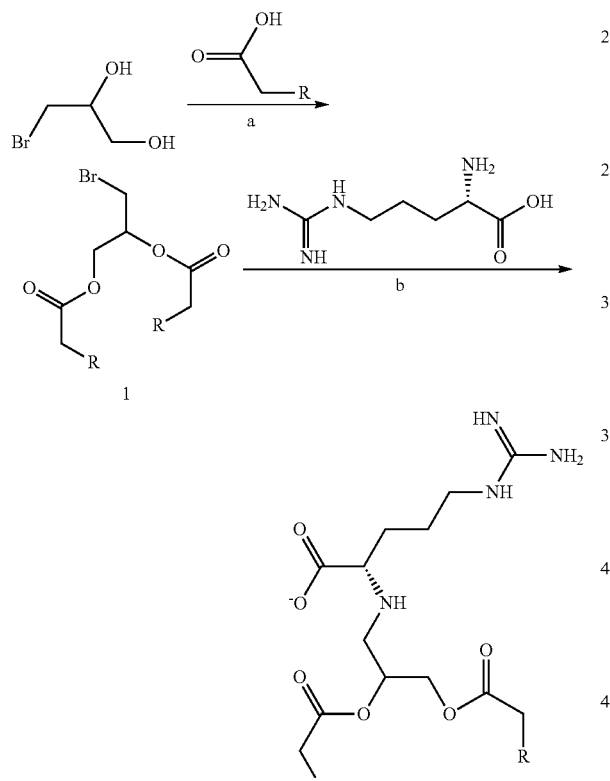

Synthesis of guanidino lipid: a) DCC (2.3 equiv), DMAP (1 equiv), CH₂Cl₂, 6 h, r.t.
b) THF, 3 days, 45° C.

Synthesis of 1—Ester Linked Lipid Backbone. 3-Bromopropane-1,2-diol was combined with the desired R-acid (2.2 eq.), N,N-dicyclohexylcarbodiimide (2.3 eq) and 4-dimethylaminopyridine (1 eq.) in anhydrous dichloromethane. The reaction was stirred at room temperature for 4 hrs. Solvents were evaporated under reduced pressure at 60° C., and the concentrated oil was redissolved in 2:1 CHCl₃:MeOH and washed 2× with H₂O. The product was then purified by HPFC.

Synthesis of 2. To a solution of 1 in tetrahyrofuran was added L-arginine (1.3 eq.) and N,N-diisopropylethylamine (1.3 eq.). The reaction was stirred at 45° C. for 72 h. The solvent was removed by evaporation under reduced pressure at 60° C., and the concentrated reaction was purified by HPFC.

Example 8

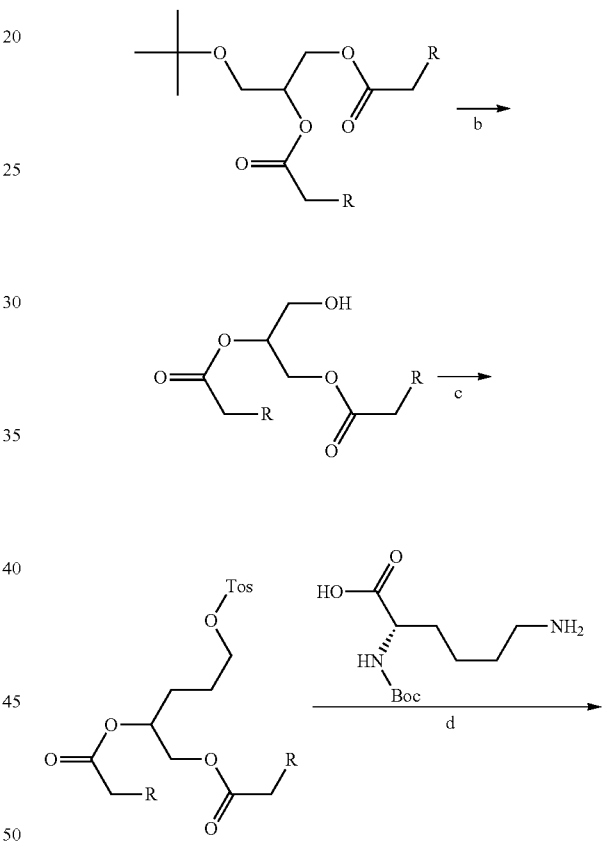

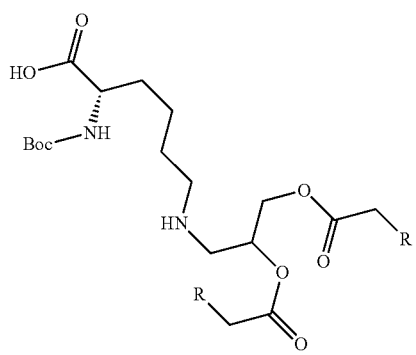

65
-continued
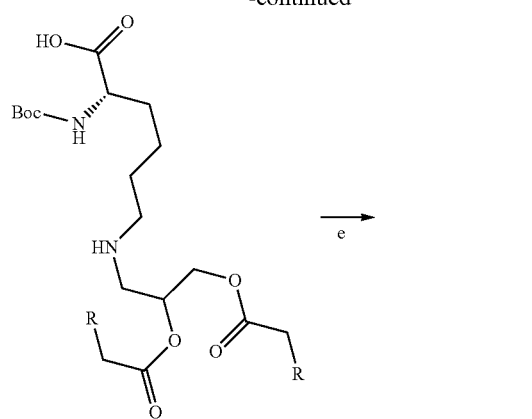
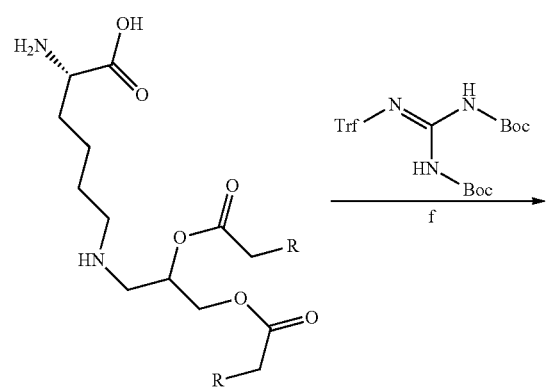
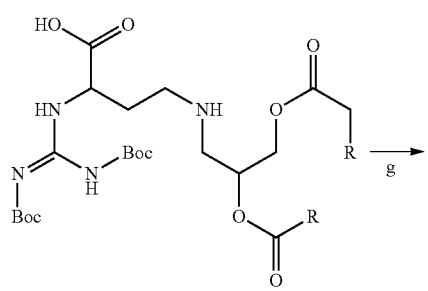
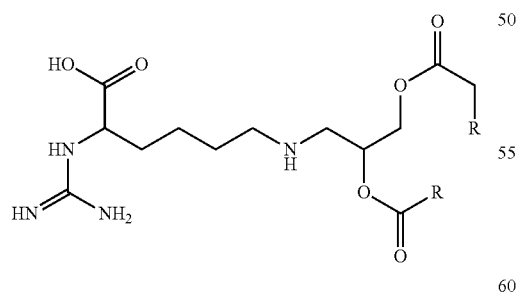
a) DCC (2.2 equiv), DMAP (0.3 equiv), 6 h, r.t. b) TFA/triisopropylsilane/CH$_2$Cl$_2$ (2:1:15), 6 h, r.t. c) 4-Toluenesulfonyl chloride, (1.1 equiv), triethylamine (2 equiv) 4° C., 5 h d) triethylamine (2 equiv), r.t. 12 h e) TFA/triisopropylsilane/CH$_2$Cl$_2$ (2:1:15), 6 h, r.t. f). triethylamine (2 equiv) g) TFA/triisopropylsilane/CH$_2$Cl$_2$ (2:1:15), 6 h, r.t.
66
Example 9
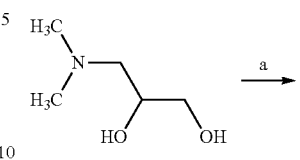
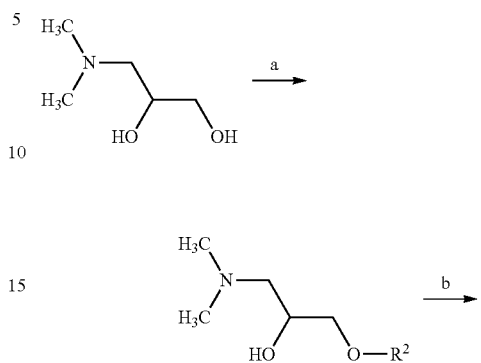
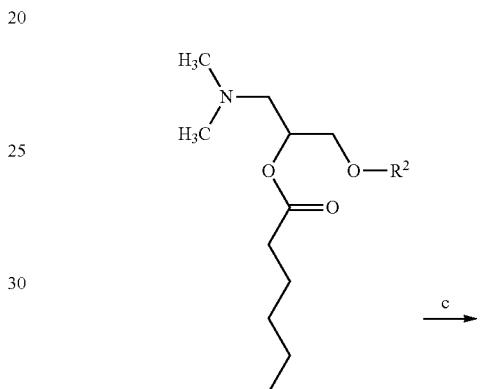
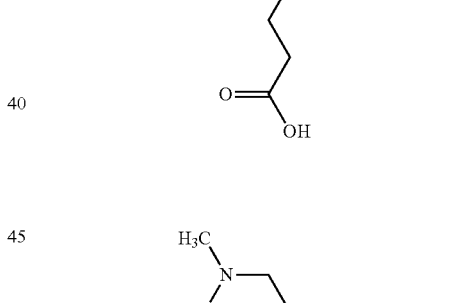
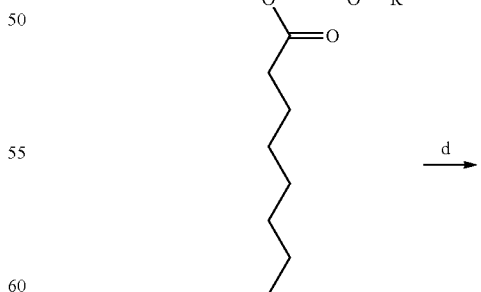
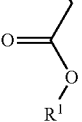

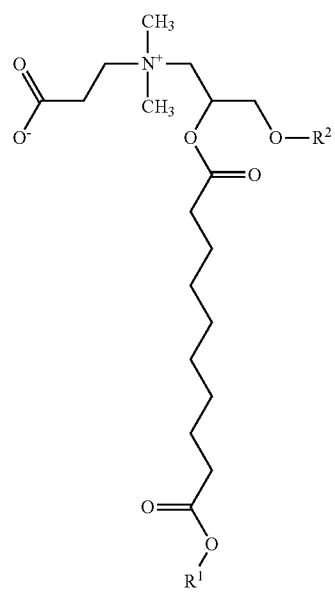

Synthesis of one FGZA (betaine-like hydrophilic group): a) $R^2$—OH (1 equiv), DCC (1.1 equiv) DMAP (0.5 equiv), $CH_2Cl_2$, 4 h, r.t. b) Sebacic Acid (3 equiv), DCC (3 equiv), DMAP (0.5 equiv), THF, 4 h, r.t. c) $R^1$ (3 equiv), $CH_2Cl_2$ (1.1 equiv), DMAP (0.5 equiv), $CH_2Cl_2$, 4 h, r.t. d) Acrylic acid, Sodium bicarbonate, $CH_2Cl_2$/THF, 7 d, 40° C.

Example 10

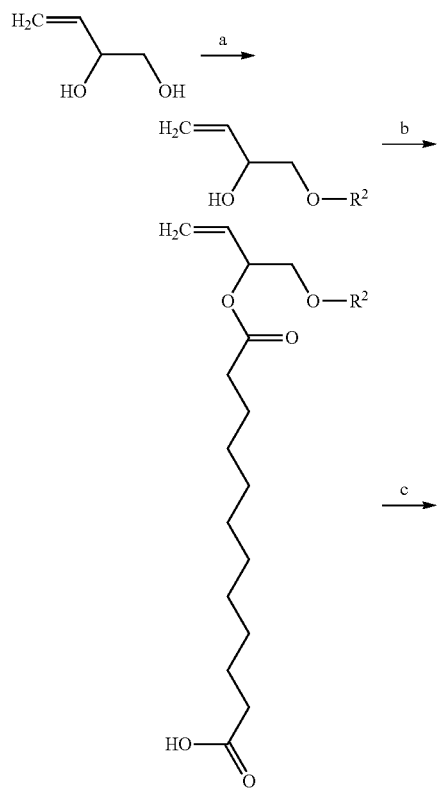

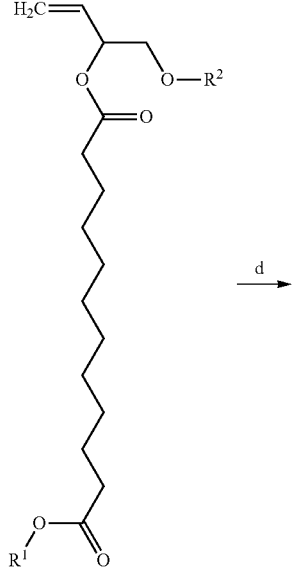

Synthesis of 1 (arginine hydrophilic group): a) $R^2$—OH (1 eq.), DCC (1.1 eq.), DMAP (0.5 eq.), $CH_2Cl_2$, 4 h, r.t.; b) sebacic Acid (3 eq.), DCC (3 eq.), DMAP (0.5 eq.), THF, 4 h, r.t.; c) $R^1$ (3 eq.), $CH_2Cl_2$ (1.1 eq.), DMAP (0.5 eq.), $CH_2Cl_2$, 4 h, r.t.; d) arginine, DMF, 80° C.

Example 11

Full Synthesis of Sample FGZA ($R^2$=CHEMS, $R^1$=1,10-Dodecanediol, all Linker=Esters)

Synthesis of 1. Cholesteryl hemisuccinate (3 g, MW 486.2) and N,N-dimethylaminopropanediol (0.73 g, MW 120) were combined in 50 mL $CH_2Cl_2$ and stirred until dissolved. Next, 0.5 g DMAP and 2.2 g of DCC were added sequentially to the reaction and it was stirred for 10 h. The reaction was then vacuum-filtered to remove the precipitated DCU. The filtrate was dried by rotary evaporation. The white solid was taken up into chloroform and purified on a Horizon Flash Chromatography system with a chloroform/methanol elution system (0-3% MeOH over 360 mL, 9 mL/fraction). The product was collected with minor impurities in fractions 45-60 and moved on to the next step.

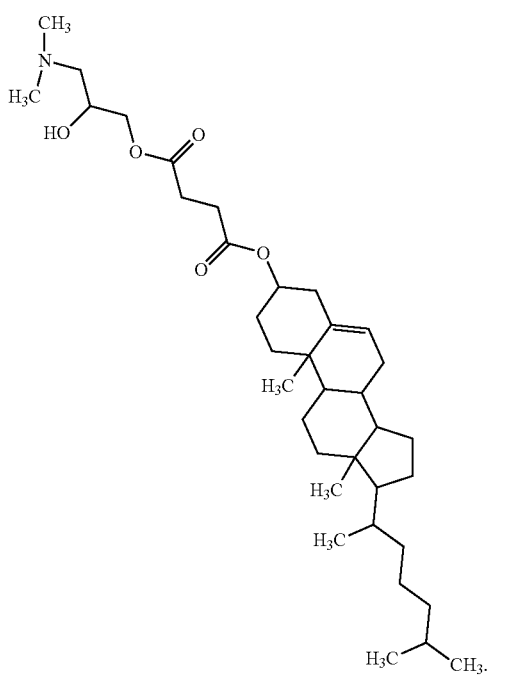

1

Synthesis of 2. 1 was dissolved in THF with 3 eq. of sebacic acid (3.74 g, MW 202.3) and stirred until completely dissolved. Then, 2.2 g of DCC and 0.5 g of DMAP were added sequentially and the reaction was stirred for 12 h at room temperature. The reaction was then vacuum-filtered to remove the precipitated DCU. The filtrate was dried by rotary evaporation. The product was purified as for 1 and was collected with minor impurities and moved on to the next step in the synthesis.

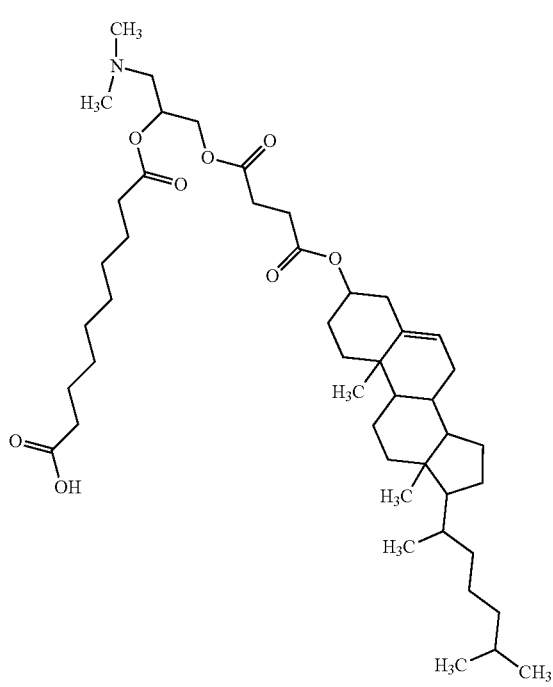

2

Synthesis of 3. 2 was dissolved in THF with 3 equivalents 1,10-decanediol (3.22 g MW 174.3) and stirred until all contents were dissolved. Then, 2.2 g of DCC and 0.5 g of DMAP were added sequentially and the reaction was stirred for 4 h at room temperature. The reaction was then vacuum-filtered to remove the precipitated DCU. The filtrate was dried by rotary evaporation. The product was purified as for 1 and was collected with minor impurities and moved on to the next step in the synthesis.

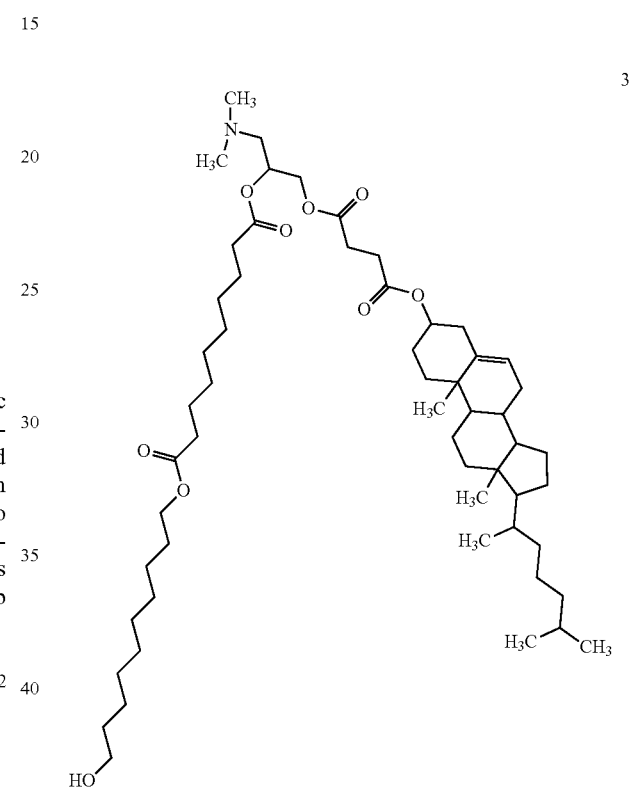

3

Synthesis of Compound 4. 3 was dissolved in minimal DCM/THF (1:1) and an excess of acrylic acid and sodium bicarbonate powder were added to the reaction. The reaction was heated at 40° C. for 7 days. The reactions were dried under vacuum and purified by silica gel chromatography with a Horizon Flash Collector. The following solvent system was used in the purification; Segment 1: 102 mL 3% MeOH/NH$_4$OH (25:5) in CHCl$_3$, Segment 2: 48 mL 3-12% MeOH/NH$_4$OH (25:5) in CHCl$_3$, Segment 3: 210 mL 12-15% MeOH/NH$_4$OH (25:5) in CHCl$_3$. The product was collected in fractions 36-30 with 6 mL/fraction. Total yield for the synthesis was 0.2%, with the majority of the loss coming in the final step. $^1$H NMR (CDCl$_3$), δ 0.68 (s), δ 0.86 (m), δ 1.0 (s), δ 1.1 (m), δ 1.3 (s), δ 1.4 (m), δ 1.6 (m), δ 2.3 (m), δ 2.6 (m), δ 2.9 (s), δ 3.1 (m), δ 3.6 (m), δ 4.0 (m), δ 4.4 (m), δ 5.4 (s).

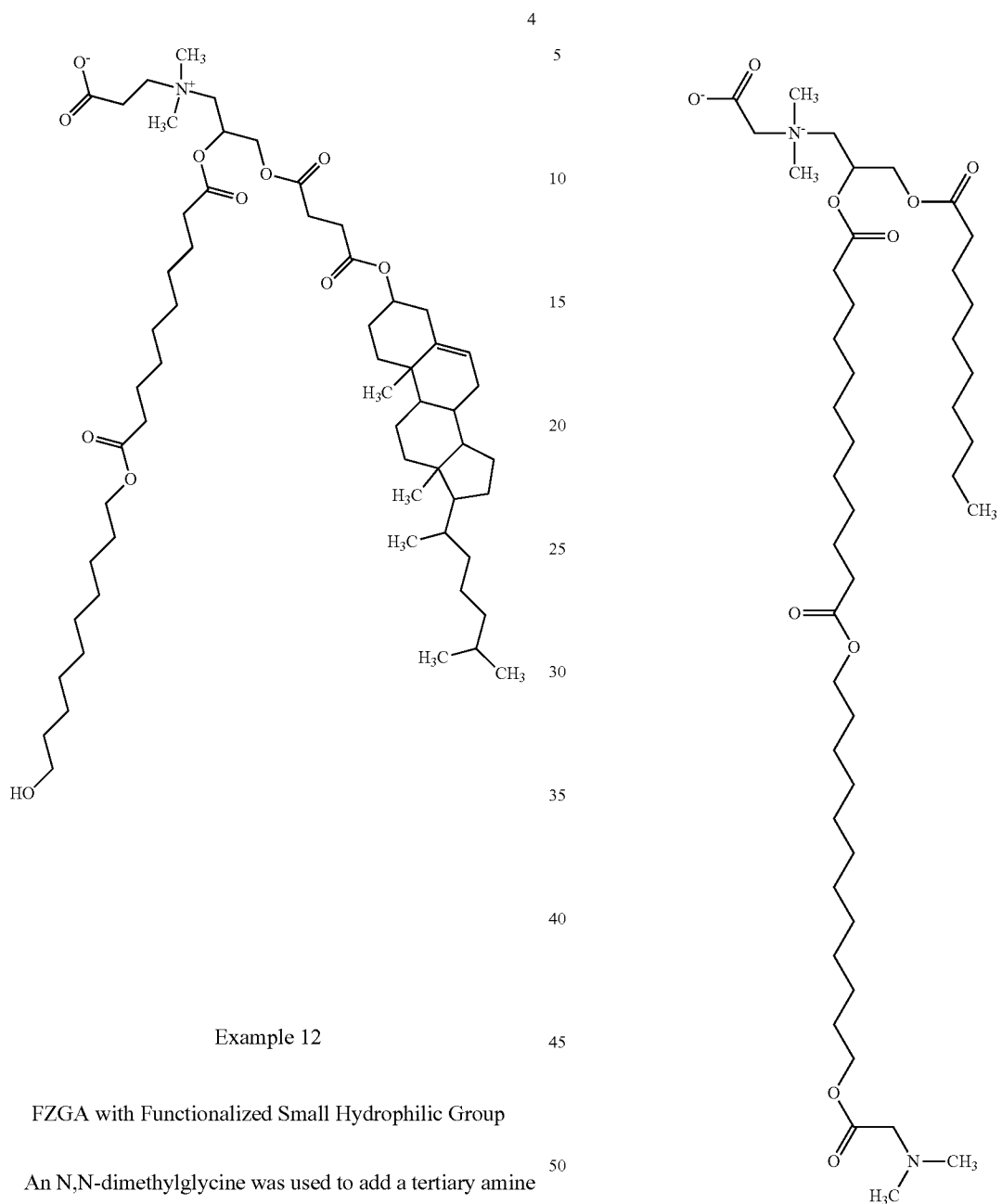

Example 12

FZGA with Functionalized Small Hydrophilic Group

An N,N-dimethylglycine was used to add a tertiary amine to the interior of two FZGA-ABAs. Tert-butyl bromoacetate was used to acylate the product. Following this step, 1.1 equiv. of N,N-dimethylaminoglycine was combined with the acylated product in pyridine and reacted with 1.1 equiv. DCC and 0.3 eq. DMAP at 40° C. for 2 days. The product was purified with silica gel chromatography with a CHCl$_3$/MeOH system. The tert-butyl group was then removed in 1:0.8:0.2 DCM:TFA:TIPS at room temperature for 4 hours. Compound 5: $^1$H NMR (CDCl$_3$), δ 0.87 (m), δ 1.28 (s), δ 1.62 (m), δ 1.9 (m), δ 2.3 (m), δ 2.7 (s), δ 3.0 (s), δ 3.4 (s), δ 4.0 (m), δ 4.2 (m). Compound 6: $^1$H NMR (CDCl$_3$), δ 0.87 (m), δ 1:26 (s), δ 1.62 (m), δ 1.67 (m), δ 1.9 (m), δ 2.3 (m), δ 2.9 (s), δ 3.6 (m), δ 3.4 (s), δ 4.0 (m), δ 4.0 (m), δ 4.6 (m).

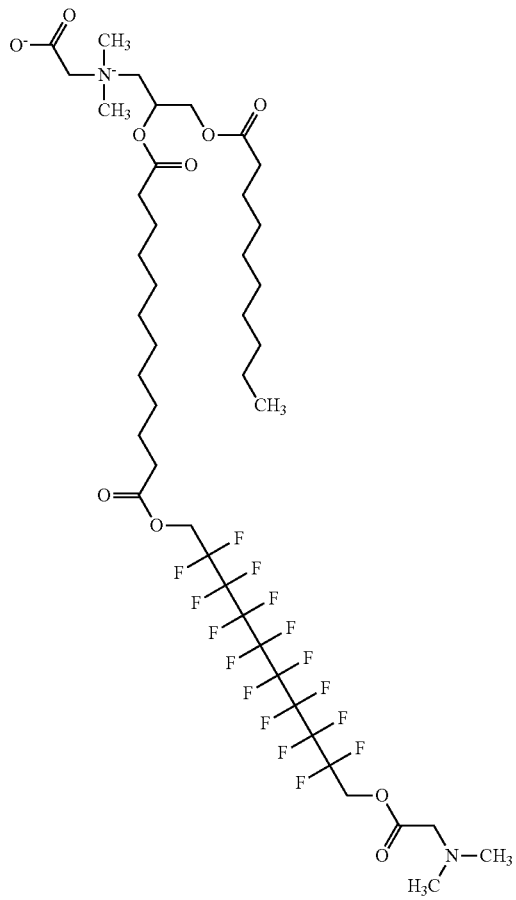

Example 13

FGZA Liposome Preparation

Pure Systems: 10 mM of a 40 mM solution of an FGZA was added to a test tube and the solvent was removed under vacuum and placed under high-vacuum overnight. Each preparation was then taken up into 200 μL of either a 0.1M glycine buffer, pH 3.1 or a 0.1M Tris buffer pH 9.1. Each preparation was then sonicated for 5 minutes at 57° C. The diameters were then measured by a Malvern Zetasizer immediately after preparation. In Table 1, X-Y, refers to the $R^2$ and $R^1$ chains respectively according to FIG. 18, where X: C=Cholesterol, T=Tocopherol, I=Isostrearyl and Y: FC=fluorocarbon and HC=hydrocarbon.

TABLE 1

| One-Component FGZA Vesicle Data | | | |
|---|---|---|---|
| Compound | Size (nm) | PDI | pH |
| C-FC | 235 | .681 | 3.1 |
| C-FC | 315 | .406 | 9.1 |
| C-HC | 102 | .143 | 3.1 |
| C-HC | 93 | .478 | 9.1 |
| T-HC | 145 | .519 | 3.1 |
| T-HC | 269 | 1 | 9.1 |
| T-FC | 263 | .315 | 3.1 |
| T-FC | 476 | .412 | 9.1 |
| I-FC | 235 | .574 | 3.1 |

TABLE 1-continued

| One-Component FGZA Vesicle Data | | | |
|---|---|---|---|
| Compound | Size (nm) | PDI | pH |
| I-FC | 2048 | 1 | 9.1 |
| N-FC | 254 | .325 | 9.1 |

Mixed Systems: The mixed FGZA-Phospholipid systems were prepared as above at the indicated molar ratio. All preparations were hydrated to 10 mM total lipid except the N—FC system, which was hydrated to 12.5 mM total lipid.

TABLE 2

| Two-Component FGZA Vesicle Data | | | |
|---|---|---|---|
| Compound | Size (nm) | PDI | pH |
| C-HC & DLPC (1:1) | 68 | .777 | 9.1 |
| C-HC & DOPC (1:1) | 97 | .237 | 9.1 |
| C-HC & DLPE (1:1) | 70 | .458 | 9.1 |
| C-HC & DOPE (1:1) | 597 | 1 | 9.1 |
| C-HC & DMPC (1:1) (in water) | 68 | .691 | 8.0 |
| C-HC & DMPC (1:1) | 65 | .621 | 9.1 |
| N-FC & DMPC (1.6:1) | 47 | .219 | 9.1 |
| T-HC & DMPC (1:1) | 61 | .579 | 9.1 |
| I-FC & DMPC (1:1) | 97 | .376 | 9.1 |
| C-HC & DLPC (1:1) | 68 | .777 | 9.1 |
| C-HC & DOPC (1:1) | 97 | .237 | 9.1 |
| C-HC & DLPE (1:1) | 70 | .458 | 9.1 |
| C-HC & DOPE | 597 | 1 | 9.1 |

Example 14

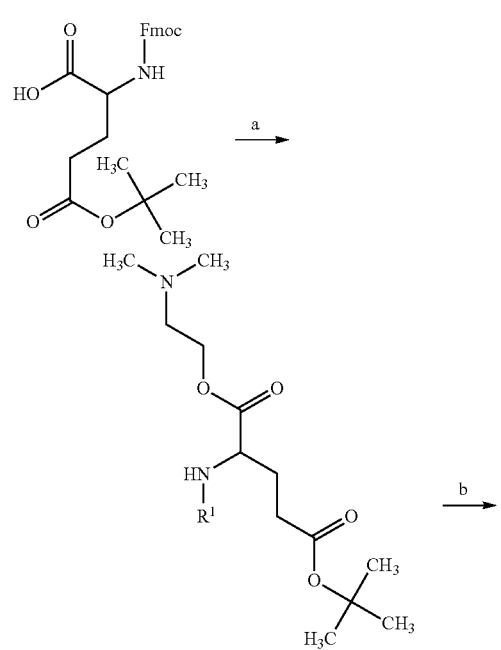

75
-continued
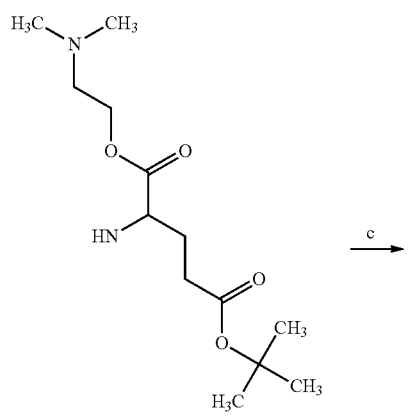
c →
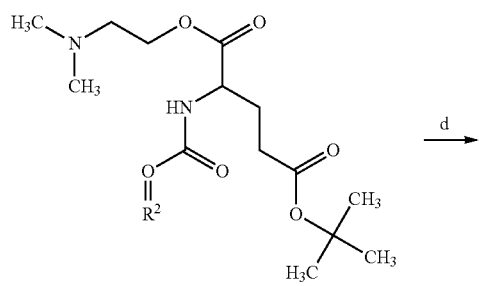
d →
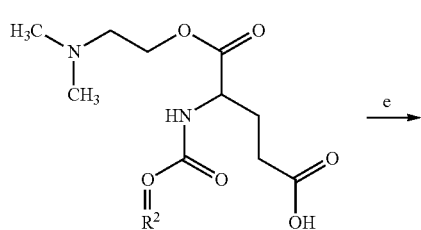
e →
76
-continued
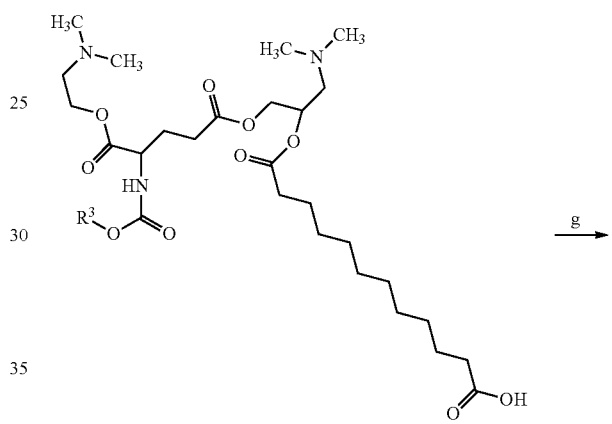
f →
g →
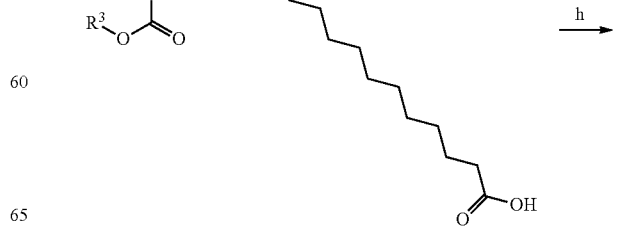
h →

77
-continued

78
-continued

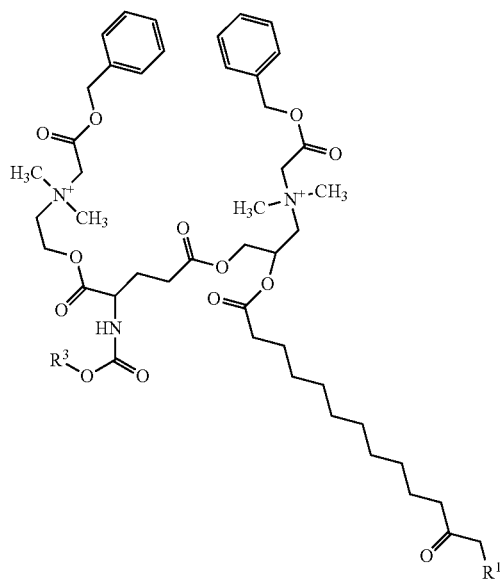

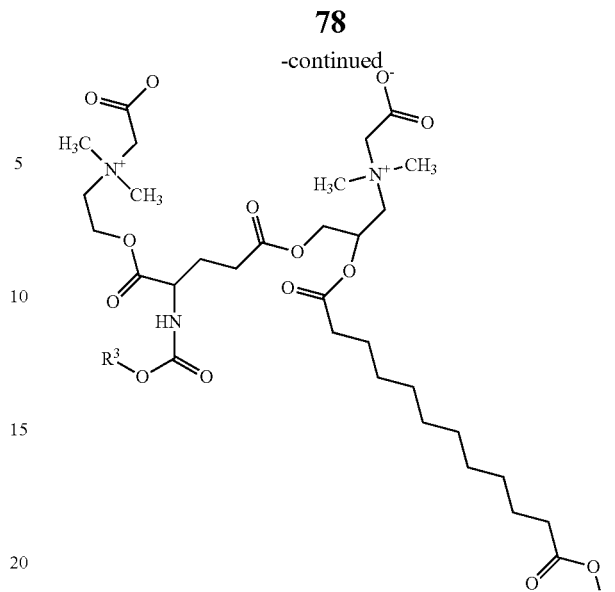

Synthesis of SGZAs. a) dimethylaminoethanol, DCC (1.1 equiv), DMAP (0.3 equiv), $CH_2Cl_2$, 6 h, r.t. b) 10% piperidine in $CH_2Cl_2$, 2 h, r.t. c) $R^2$—COOH, DCC (1.1 equiv), DMAP (0.3 equiv), $CH_2Cl_2$, 4 h, r.t. d) TFA/triisopropylsilane/$CH_2Cl_2$ (2:1:15), 6 h, r.t. e) N,N-dimethylpropanediol (2 equiv), DCC (2.2 equiv), DMAP (0.3 equiv), $CH_2Cl_2$, 6 h, r.t. f) 1.12-dodecanedioic acid (3 equiv), DCC (3 equiv), DMAP (0.3 equiv), DMF, 4 h, r.t. g) benzyl bromoacetate (3 equiv), THF, 2 days, 40° C., h) $R^1$—OH (3 equiv), DCC (1.1 equiv), DMAP (0.3 equiv), DMF or THF, 4 h, r.t. i) Pd (IV) on activated carbon (0.3 equiv), ammonium formate (4 equiv), methanol/water (20:1), 10 h, 40° C..

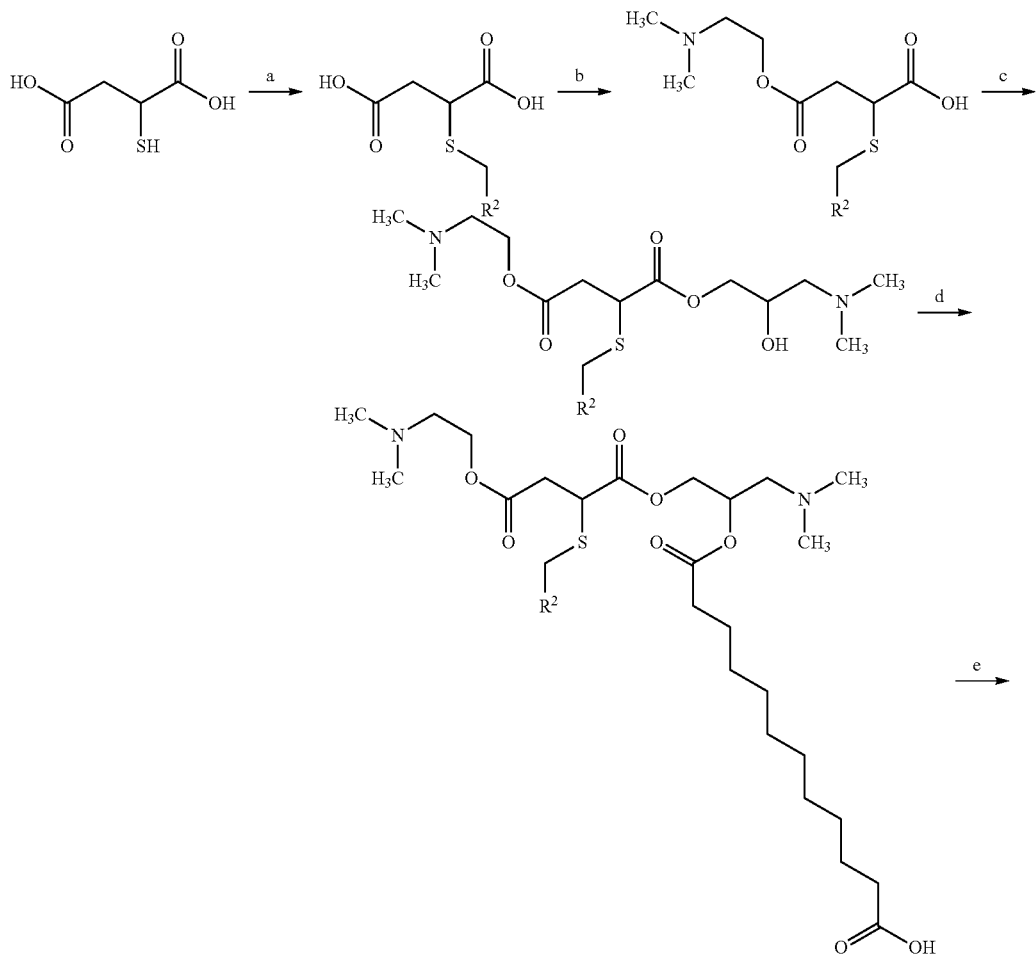

-continued
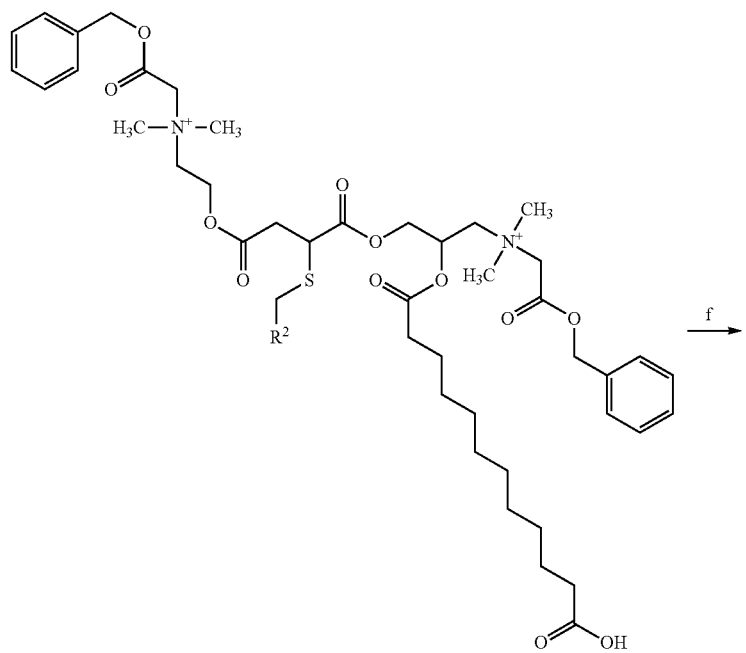
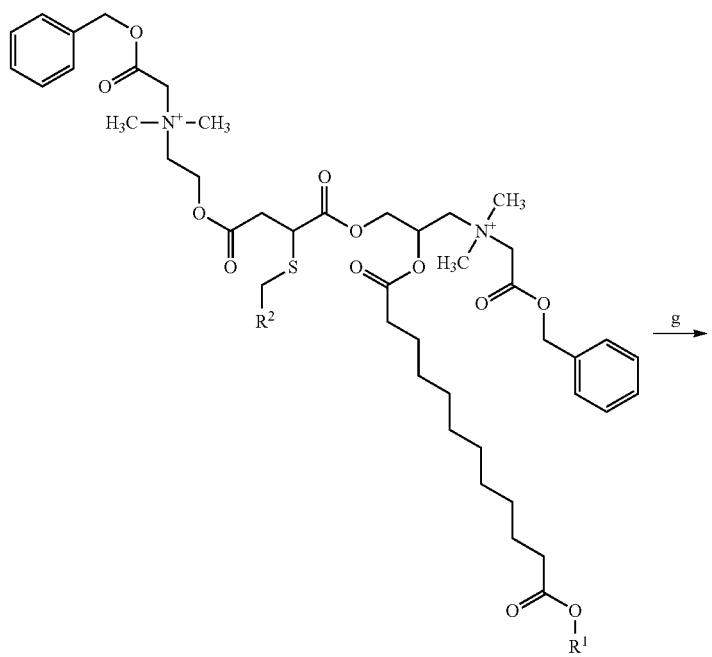

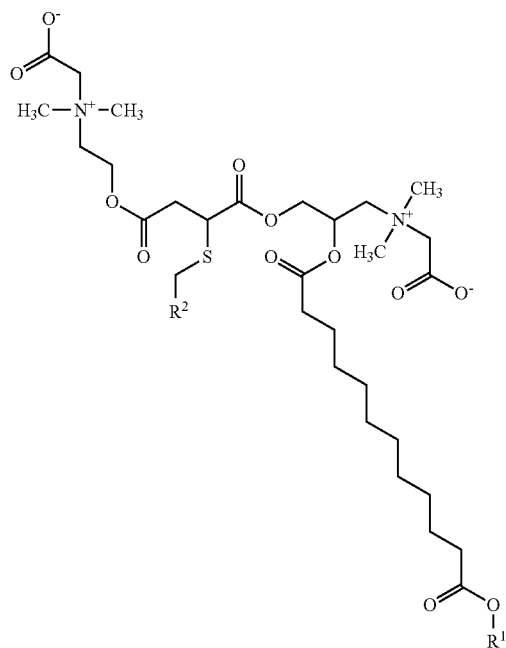

Synthesis of SGZTA (Betaine-like hydrophilic groups): a) $R^2$-ene (1 equiv), 2,2-dimethyl-2-phenylacetophenone (0.5 equiv), MeOH, UV light, 20 min, b) dimethylaminoethanol (1 equiv), DCC (1.1 equiv), DMAP (0.3 equiv), 6 h, r.t. c) N,N-dimethylaminopropanediol (2 equiv), DCC (2 equiv), DMAP (0.3 equiv), $CH_2Cl_2$, 6 h, r.t. d) 1,12-dodecanedioic acid (3 equiv), DCC (3.3 equiv), DMAP (0.3 equiv), DMF, 4 h, r.t. e) benzyl bromoacetate (3 equiv), THF, 2 days, 40° C., f). $R^1$—OH (2 equiv), DCC (1.1 equiv), DMAP, THF, 4 h, r.t. g). Pd (IV) on activated carbon (0.3 equiv), ammonium formate (4 equiv), methanol/water (20:1), 10 h, 40° C.

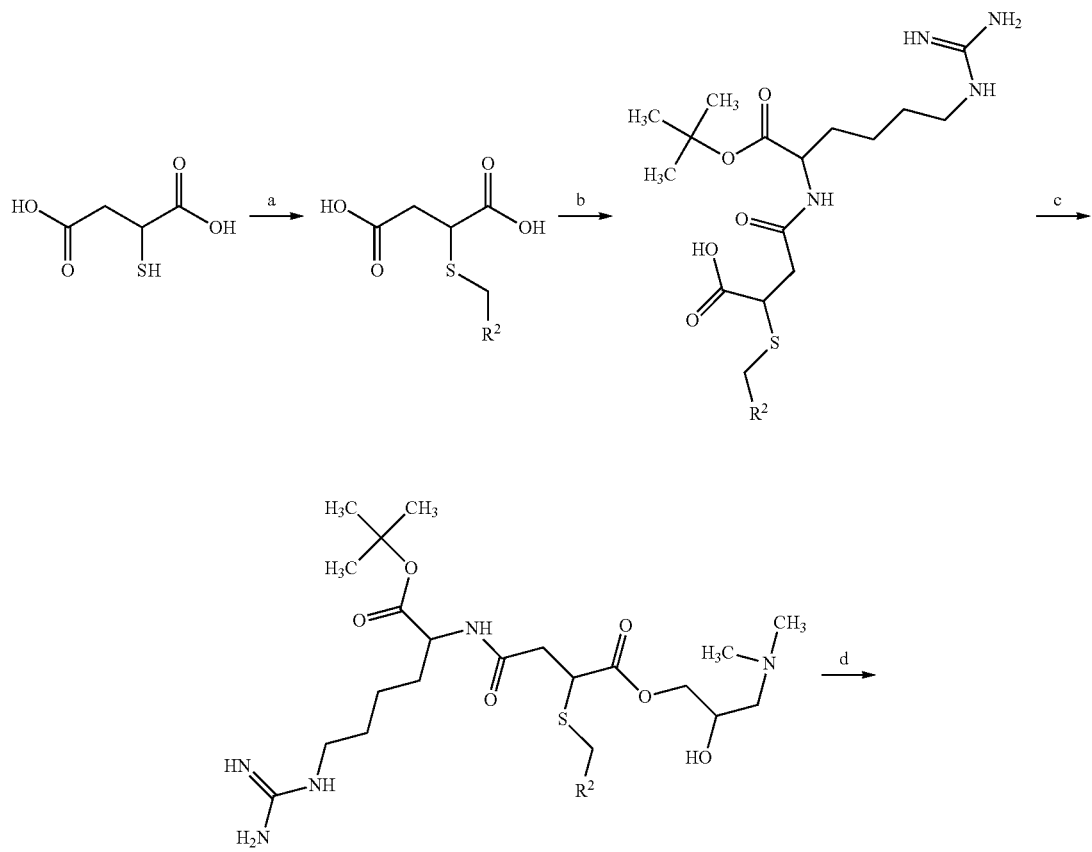

-continued
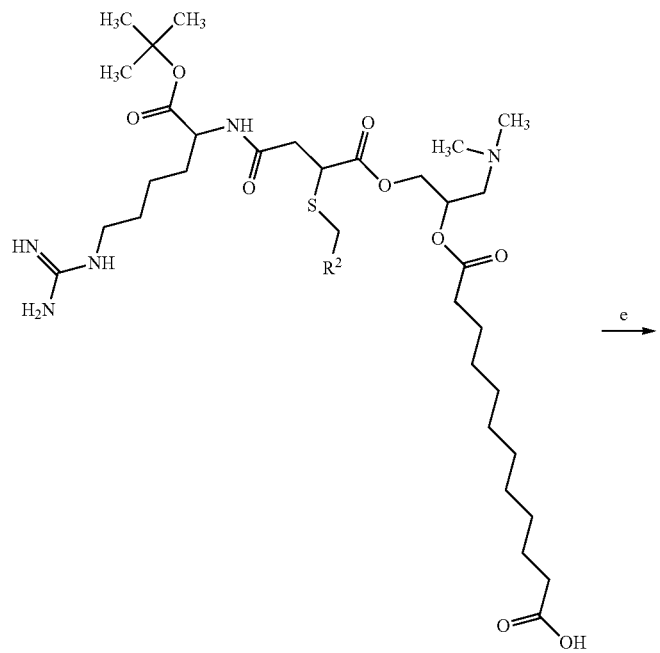
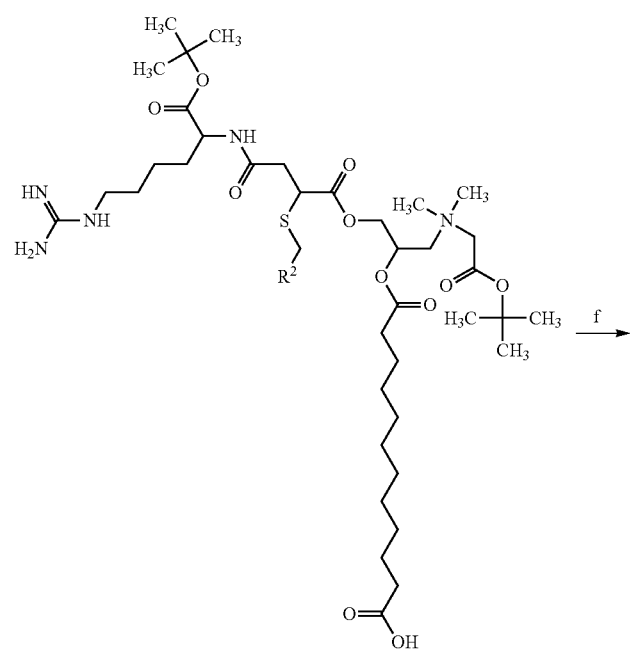

-continued

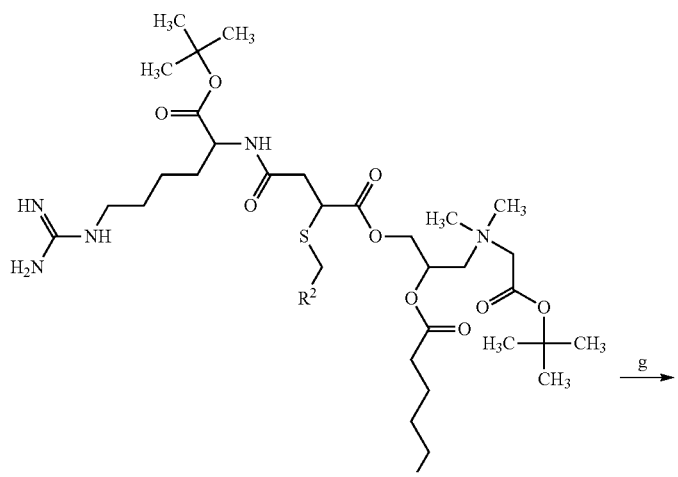

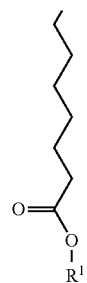

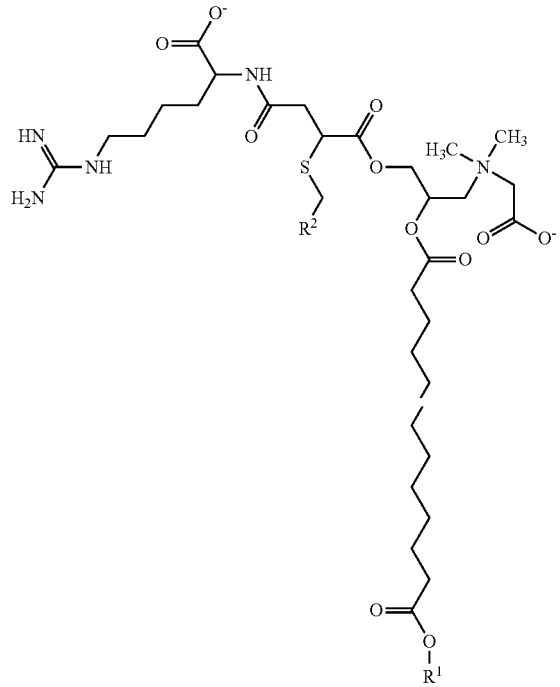

Synthesis of SGZTA (with arginine hydrophilic group): a) $R^2$-ene (1 equiv), 2,2-dimethyl-2-phenylacetophenone (0.5 equiv), MeOH, UV light, 20 min, b) Tert-butyl protected arginine (1 equiv), DCC (1.1 equiv), DMAP (0.3 equiv), 6 h, r.t. c) N,N-dimethylaminopropanediol (2 equiv), DCC (2 equiv), DMAP (0.3 equiv), $CH_2Cl_2$, 6 h, r.t. d) 1,12-dodecanedioic acid (3 equiv), DCC (3.3 equiv), DMAP (0.3 equiv), DMF, 4 h, r.t. e) tert-butyl bromoacetate (3 equiv), THF, 2 days, 40° C., f) $R^1$—OH (2 equiv), DCC (1.1 equiv), DMAP, THF, 4 h, r.t .g). TFA/triisopropylsilane/$CH_2Cl_2$ (2:1:15), 6 h, r.t.

Example 15

A Biophysical Comparison of Inverse Zwitterlipids to their Phosphatidylcholine Counter Parts We introduce a new class of zwitterionic phosphocholine lipids in which the positions of the choline and phosphate groups are switched placing the choline adjacent to the hydrocarbon chains and the phosphate at the headgroup terminus (referred here forth as CP lipids with standard phospholipid chain terminology). Two different headgroups, one with an overall negative charge (CP) and one with a neutral charge (CPe) at pH 7.4, were synthesized and their biophysical properties were compared to naturally occurring phosphatidylcholine (PC) and phosphatidic acid (PA) lipids. The presentation of a phosphate at the interface is a key aspect of mediating the interactions of phospholipid messenger molecules (phosphatidyl serine, phosphatidic acid, and phosphorylated ceramide and sphingosine) with their respective receptors, and also in the host recognition of the phosphorylated lipopolysaccharides in bacterial walls. All of these can contribute to the induction of an immunological response and the phospholipid messenger molecules mediate several biological processes. Here we report the differences in zeta-potential, small molecule leakage, calcium-induced aggregation, and calcium-induced changes in zeta-potential between naturally occurring phosphocholine or phosphatidic acid lipids and the CP lipids. Based on these results, CP lipids may be useful components for liposomal drug and vaccine delivery.

Synthesis

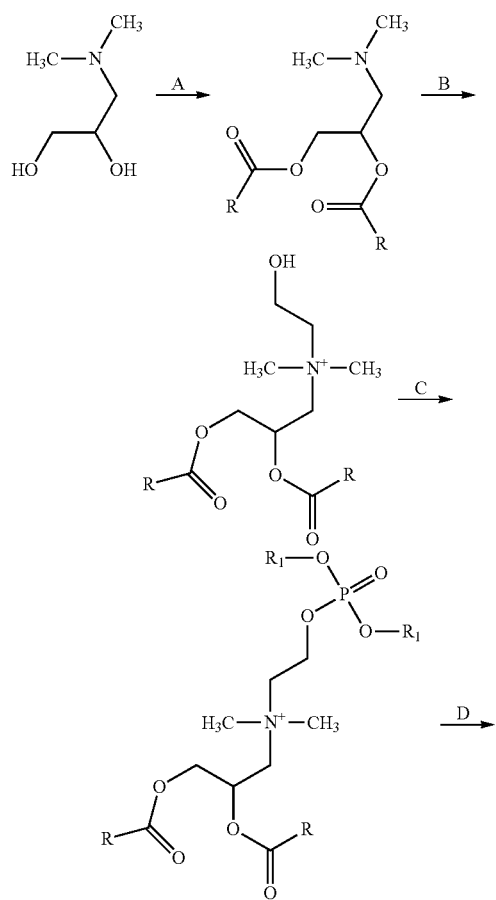

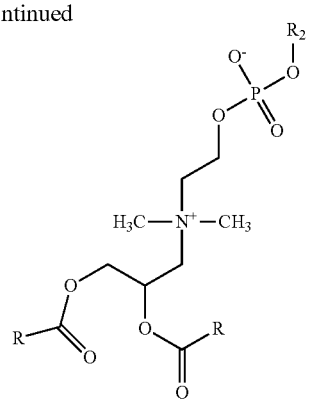

A) oleic acid, DCC, DMAP, $CH_2Cl_2$ B) 2-bromoethanol, DIPEA, 35° C. C) 1) In a separate flask; trimethylphosphite or triethylphosphite, $I_2$ 2) (1), pyridine, DCM, R1 = ethyl or methyl D) LiBr/acetone/acetonitrile for ethyl group TMS—Cl/NaI/Acetonitrile for methyl groups, both deprotections done while refluxing. $R_2$ = ethyl (DOCPe) or hydrogen (DOCP). C3—DOCP contains an extra carbon between the nitrogen and phosphate groups and is synthesized by replacing 2-bromoethanol with 3-bromopropane in step (B).

Liposomes were prepared from either DOPC or DOCPe and their zeta potentials were measured in a Malvern zetaNano instrument as a function of the calcium concentration. Liposomes prepared from either lipid become more positively charged as the $Ca^{2+}$ concentration increases. The zeta potentials of DOCPe liposomes remain negative across physiological $Ca^{2+}$ concentrations, while liposomes prepared form DOPC become positively charged as indicated in FIG. 32.

To determine if liposomes prepared from the inverse zwitterlipid retained encapsulated anionis differently than liposomes prepared form the natural DOPC we measured the leakage of the anionic fluorescent molecule carboxyfluorescein that was encapsulated in the liposome at a self-quenched concentration. Lipid films were rehydrated in 10 mM Tris-HCl, 100 mM CF solution and sonicated at 50° C. for 10 minutes. Free CF was removed with a PD-10 column with an iso-osomotic buffer, 10 mM HEPES, 105 mM NaCl and the fluorescence was monitored over time (Ex. 485 Em. 520). Each lipid was tested in triplicate. The anionic CF leaked faster from liposomes composed of the two inverse zwitterlipids than it did from liposomes prepared from the normal DOPC as plotted in FIG. 33.

Example 16

Sulfobetaine Zwitterlipids Form Liposomes that have Salt-Type Dependent Thermotropic Properties that can be Used to Prepare a Liposome that can be Heat Triggered to Rapidly Release its Contents We have synthesized a new class of zwitterionic diacylsulfobetaine lipids (SBLs) with salt-dependent properties that have not been reported for traditional zwitterionic phospholipids. SBLs differ from typical phosphocholine lipids (PCLs) in the headgroup region with the location of the two charged moieties switched and in the type of anionic group employed. In SBLs, the cationic quaternary amine is adjacent to the hydrophobic region and the sulfonate extents away from the bilayer. SBLs are synthesized from low cost precursors in a simple two-step synthesis that does not require chromatography. SBL liposomes do not interact strongly with $Ca^{2+}$ or aggregate in the presence of high $Ca^{2+}$ concentrations. Like PCLs, SBLs are zwitter-neutral across a wide pH range, but in the presence of salt, SBL liposomes gain an overall negative surface potential due to the preferential binding of anions to the SBL liposome surface.

Additionally, SBLs exhibit two salt-dependent transition temperatures. High salt concentrations and anions with high polarizabilities promote a low transition temperature, close to PC analogs, while low salt concentrations and anions with low polarizabilities result in a higher transition temperature, similar to phosphatidylethanolamine analogs. This differential effect of salt type on the thermal transition temperature can be used to prepare a liposome in one salt type such as sodium bromide that when diluted into a second salt type such as sodium chloride, alters the transition temperature of the bilayer. This can be used to prepare a liposome that release a significant fraction of its encapsulated contents in less than 30 seconds when the temperature is raised from 37 C to 41 C. This property can be used to make a temperature sensitive liposome for drug delivery in areas of the body where the temperature is greater than the normal body temperature of 37 C.

Synthesis of Sulfobetaine Lipids

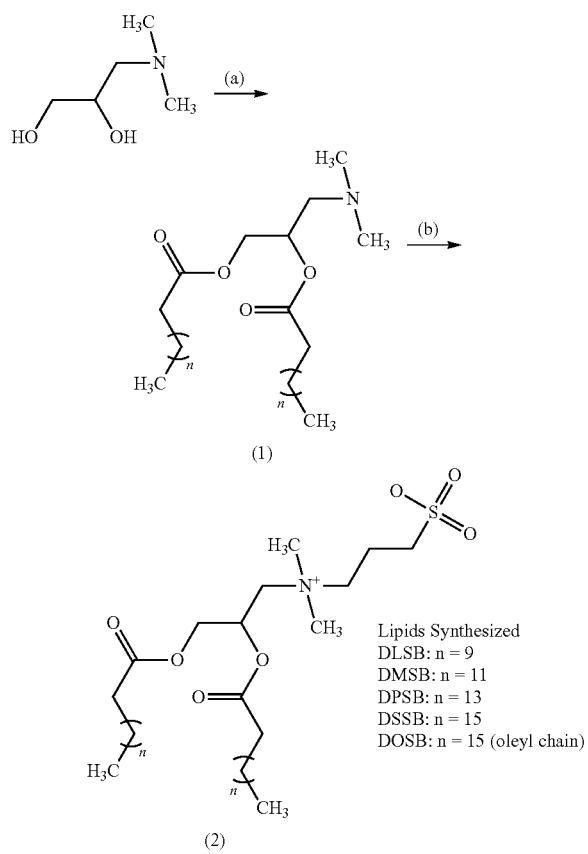

Chemical Synthesis (a) $C_{n+3}$ alkyl acid, DCC, DMAP, $CH_2Cl_2$, r.t. 4 hrs.
(b) 1,3-Propanesultone, DIPEA, $CH_2Cl_2$, MeOH (4:1), 40° C., 18 hrs.

The SB lipid library was synthesized from a 3-(dimethylamino)-1,2-propanediol core via a two step synthesis without the need for column purification for the saturated chain versions. After the alkylation with 1,3-propanesultone in the presence of DIPEA, the reaction was washed with 1 M HCl and 1M $Na_2CO_3$, and then precipitated from acetone, hexanes, and acetonitrile sequentially, to afford pure SBL products in moderate yields. Five SBLs were made varying only at the alkyl chains (lauric acid=DLSB ($C_{12}$), myristic acid=DMSB ($C_{14}$), palmitic acid=DPSB ($C_{16}$), stearic acid=DSSB ($C_{18}$), and oleic acid=DOSB ($C_{1:81}$)). This straightforward synthesis requires relatively inexpensive materials and a purification that could make it suitable for cost-effective scale-up and result in a less expensive alternative to PCLs for some applications.

Materials and Methods

Materials

DPPC, DSPC, and DSPG were purchased from Avanti Polar Lipid. DiD (D-307) was purchased from Molecular Probes (Eugene, Oreg.). Solvents were purchased from VWR Scientific. All other chemicals were purchased from Sigma Aldrich. All buffers were made with MilliQ water and passed through a filtration system. NMR measurements were taken on a Bruker 300 MHz Avance system and analyzed with Topspin software. Chemical shifts are expressed as parts per million with tetramethylsilane as internal standard. HPFC column purifications were performed on a Reveleris Flash System (Grace Division Biosciences) with pre-packed GraceResolv silica cartridges (67 Å, 40.5 μm).

Methods

General Synthetic Procedure:

1 g of N,N-dimethylamino-1,2-propanediol (8.3 mmoles) and 2.2 molar equivalent of alkyl acid chain were dissolved in methylene chloride while stirring at room temperature. Then, 0.1 g DMAP and 2.2 molar equivalent of DCC were added and the solution was stirred for 3-4 hours or until complete by TLC. Additional small portions of DCC were added if necessary to drive the reaction to completion. The solution was then filtered to remove the precipitated DCU and washed 2× with 1M HCl. The organic layer was collected and dried with sodium sulfate and solvent was removed by rotary evaporation. The di-substituted dimethylaminoglycerol product (1) was moved forward with no further purification.

To (1) was added 2 molar equivalents 1,3-propanesultone with 0.5 mL DIPEA in minimal methylene chloride/methanol (4:1). The reactions were stirred while heating at 40° C. for 18 hours. The solutions were diluted with the reaction solvent mixture and washed with 1M HCl followed by 1 M $Na_2CO_3$. The organic layer was collected and concentrated under rotary evaporation. DLSB, DMSB, DPSB, DSSB were purified through a series of precipitation from methylene chloride in acetone, acetonitrile, and hexanes. Small amounts of product were lost in each precipitation step and overall yields for the entire synthesis were 20%, 66%, 32%, and 38% for the (C12) DLSB, (C14) DMSB, (16) DPSB, and (C18) DSSB respectively. (C18:1) DOSB could not be purified by precipitation and was instead purified by HPFC, and was eluted with 30% methanol in methylene chloride with a yield of 7.6%. In the DOSB synthesis, a significant amount of side product with a molecular weight corresponding to two additions of the 1,3-propanesultone was observed on MALDI and it is possible that the 1,3-propanesultone was added across the alkene in one of the oleyl chains.

DLSB: $^1$H NMR (CDCl$_3$/CD$_3$OD ~10:3): δ 0.87 (t, 6H); δ 1.26 (m, 32H); δ 1.60 (m, 4H); δ 2.23 (m, 2H); δ 2.32 (m, 4H); δ 2.90 (t, 2H); δ 3.14 (d, 6H); δ 3.66-3.78 (m, 4H); δ 4.05-4.09

(m, 1H); δ 4.43-4.48 (m, 1H); δ 5.60 (m, 1H). MALDI-MS calc'd mass 606.9, found 607.87.

DMSB: $^1$H NMR (CDCl$_3$/CD$_3$OD ~10:3): δ 0.89 (t, 6H); δ 1.27 (m, 40H); δ 1.62 (m, 4H); δ 2.22 (m, 2H); δ 2.38 (m, 4H); δ 2.87 (t, 2H); δ 3.14 (d, 6H); δ 3.59 (m, 2H); δ 3.71 (m, 2H); δ 4.04-4.08 (m, 1H); δ 4.46-4.47 (m, 1H); δ 5.62 (m, 1H). MALDI-MS calc'd mass 663.02, found 664.62.

DPSB: $^1$H NMR (CDCl$_3$/CD$_3$OD ~10:3): δ 0.88 (t, 6H); δ 1.26 (m, 48H); δ 1.60 (m, 4H); δ 2.21 (m, 2H); δ 2.33 (m, 4H); δ 2.88 (t, 2H); δ 3.14 (d, 6H); δ 3.60-3.70 (m, 4H); δ 4.02-4.08 (m, 1H); δ 4.43-4.48 (m, 1H); δ 5.60 (m, 1H). MALDI-MS calc'd mass 719.12, found 721.49.

DSSB: $^1$H NMR (CDCl$_3$/CD$_3$OD ~10:3): δ 0.83 (t, 6H); δ 1.20 (m, 56H); δ 1.56 (m, 4H); δ 2.15 (m, 2H); δ 2.29 (m, 4H); δ 2.84 (t, 2H); δ 3.07 (d, 6H); δ 3.6 (m, 4H); δ 3.96-4.02 (m, 1H); δ 4.38-4.42 (m, 1H); δ 5.50 (m, 1H). MALDI-MS calc'd mass 775.23, found 776.51.

DOSB: $^1$H NMR (CDCl$_3$/CD$_3$OD ~10:3): δ 0.90 (t, 6H); δ 1.30 (m, 40H); δ 1.60 (m, 4H); δ 2.03 (m, 8H); δ 2.33 (m, 6H); δ 2.90 (m, 2H); δ 3.27 (d, 6H); δ 3.6-3.87 (m, 3H); δ 4.00 (m, 1H); δ 4.13 (m, 1H); δ 4.50 (m, 1H); δ 4.36 (m, 4H); δ 5.64 (m, 1H). MALDI-MS calc'd mass 771.20, found 772.88.

TABLE 3

Elemental Analysis

| sampleID | calculated % C | observed % C | calculated % H | observed % H | calculated % N | observed % N |
|---|---|---|---|---|---|---|
| DSSB | 68.3 | 68.08 | 11.3 | 11.46 | 1.81 | 1.84 |
| DMSB | 65.3 | 64.92 | 10.8 | 10.54 | 2.12 | 2.13 |
| DPSB | 66.9 | 66.62 | 11.09 | 11.31 | 1.95 | 1.99 |
| DLSB | 63.4 | 62.54 | 10.5 | 10.72 | 2.31 | 2.34 |
| DOSB | 68.61 | 67.4 | 10.86 | 10.95 | 1.82 | 1.85 |

Vesicle Formation

The five SBLs were first examined for their ability to make vesicles under standard buffer conditions (10 mM HEPES, 140 mM NaCl, pH 7.4). We observed that none of the five SBLs were able to form stable liposomes after thin film rehydration in this buffer followed by sonication at 80° C. DLSB showed the most promise, but still formed large, polydisperse structures. To test if the SB headgroup inner salt interactions could be disrupted by an increase in salt concentration, the same liposome formation process was performed at increasing NaCl concentrations. Salts with different anions were also tested to determine if those predicted to have greater binding than Cl$^-$ would allow for liposome formation at concentrations where NaCl was not able to. Liposome-formation results are shown in Table 4 for all five SBLs with a variety of salts and at various NaCl concentrations.

TABLE 4

Liposome diameter (nm), PDI in Various NaCl Concentrations

| Lipid | 1000 mM NaCl | 500 mM NaCl | 150 mM NaCl | 0 mM NaCl |
|---|---|---|---|---|
| DLSB | 56.5, 0.361 | 41.7, 0.296 | 1728, 0.708 | DNF |
| DMSB | 76.8, 0.233 | 63.92, 0.385 | DNF | DNF |
| DPSB | 92.53, 0.275 | 66.95, 0.253 | DNF | DNF |
| DSSB | 137.9, 0.404 | 122.7, 0.285 | DNF | DNF |
| DOSB | 118.9, 0.176 | 126.9, 0.197 | DNF | DNF |

Table 5 shows liposome diameters and PDIs in various concentrations of NaCl. Liposome preparations were made at 26 mM lipid in 10 mM HEPES buffer, pH 7.4 with the specified salt concentration. All preparations were rehydrated and sonicated at 80° C. for 7 minutes, allowed to cool for 5 minutes and then measured. DNF=Did Not Form, no liposomes formed.

TABLE 5

Liposome diameter (nm), PDI In Various Salts Following Sonication and at 24 Hours

| Lipid | 150 mM NaClO$_4$ | 150 mM NaClO$_4$ (24 h) | 150 mM NaI | 150 mM NaI (24 h) | 150 mM KBr | 150 mM KBr (24 h) | 150 mM NaF |
|---|---|---|---|---|---|---|---|
| DLSB | 30.46, 0.205 | 37.32, 0.251 | 28.93, 0.163 | 39.24, 0.215 | 54.56, 0.276 | 74.35, 0.254 | DNF |
| DMSB | 41.76, 0.239 | 43.68, 0.24 | 35.3, 0.232 | 38.69, 0.250 | 28.53, 0.160 | 31.67, 0.181 | DNF |
| DPSB | 35.1, 0.220 | 42.71, 0.353 | 57.45, 0.296 | Formed Gel | 64.35, 0.134 | Precipitated | DNF |
| DSSB | 42.45, 0.258 | 71.96, 0.282 | 43.31, 0.231 | Formed Gel | 102.3, 0.123 | Precipitated | DNF |
| DOSB | 67.7, 0.250 | 69.18, 0.235 | 90.58, 0.246 | 99.24, 0.253 | 120.8, 0.260 | 137.6, 0.353 | DNF |

Table 5 shows liposome diameters and PDIs in various salts. Liposome diameters were measured both five minutes after sonication and at 24 hours. DPSB and DSSB in NaI both formed gels and could not be measured and DPSB and DSSB with KBr precipitated into particles too large and polydisperse for measurement. DNF=Did Not Form, no liposomes formed.

Increasing the NaCl concentration to 500 mM resulted in the ability of every SBL to form small-diameter liposomes with low PDIs upon brief heating and sonication at 80° C. Very small vesicles were observed for both of the higher NaCl concentrations for the C$_{12}$-C$_{16}$ SB lipids. Changing the salt form from NaCl to NaClO$_4$, NaI, or NaBr at 150 mM resulted in a significant increase in the ability to make liposomes. The vesicles formed in these three salts were all reasonably small, with those formed in KBr having, on average, a slighter larger diameter. This may be due the weaker binding of Br$^-$ to the cationic region of the SBLs relative to I$^-$ and ClO$_4^-$, which would result in a higher percentage of SBLs in the inner-salt conformation. This is supported by zeta-potential measurements of DMSB in the various salt solutions (data not shown) that revealed the surface potential of the liposomes was most negative for ClO$_4^-$>I$^-$>Br$^-$>Cl$^-$, insinuating a higher degree of anion binding in the same order. As expected, lipid preparations made in 150 mM NaF performed more poorly than in NaCl and did not support the formation of liposomes. Even at 500 mM NaF, DMSB was unable to form liposomes.

Based on our observations that SBL liposome formation and stability is largely dependent on salt composition and concentration we sought to determine if these effects changed the transition temperatures of the liposomes. The data in FIG. 3 clearly depicts a bi-modal phase transition behavior for the SBLs. Without salt, the majority of the SBLs are likely in one of the inner salt forms supported by the observed elevated transition temperatures. The switch from high (inner salt) to low (outer salt) transition temperature seems to occur at different NaCl thresholds for the different chain lengths, with the shortest, DMSB ($C_{14}$), existing as the outer salt with a high transition temperature for all NaCl concentrations up to 1M. DPSB ($C_{16}$), however, switches from the inner salt to the outer salt at 500 mM with a small hint of inner salt still present at 58° C. DSSB ($C_{18}$) never exists completely as the inner salt conformation, but does reside as the outer salt form at 500 mM. Interestingly, DSSB shows a small low transition peak in a buffer without NaCl. These data show that it is more difficult to break up the inner salt form for shorter chain SBLs and that the effect on the transition temperature relative to PC is greatest for shorter chain lengths.

TABLE 6

Transition Temperatures (° C.) for Hypothesized Inner and Outer Salt SBL Forms Compared to PE and PC Headgroups

| Chain Length | PE | SB Inner Salt | PC | SB Outer Salt |
|---|---|---|---|---|
| C14 | 49.4 | 48 | 24.2 | 25-30 |
| C16 | 63.5 | 60 | 41.7 | 43 |
| C18 | 74.4 | 68 | 55.3 | 57 |

Table 6 shows literature values for the phase transition temperatures of PELs and PCLs compared to those found for SBLs. Inner and outer salt conformations of the SBLs are hypothesized to coordinate to the observed high and low phase transitions, respectively.

The same chain-dependent trends occur with the other salts with DMSB and DPSB having only the low transition in NaF and only the high transition in $NaClO_4$. DSSB has both transitions for all salts except $NaClO_4$. It is unclear what the two smaller peaks in the DPSB traces with NaI and KBr are, but they may be due to a small amount of an inner salt form mixed in with primarily outer-salt SBLs, creating an intermediate transition temperature as has been observed in DPPC/DPPE mixed systems. However, for the majority of the SBLs, there seems to be a phase separation of the two SBL forms resulting in two distinct peaks and not one intermediary peak.

To prepare liposomes from the DPSB lipid (C16 chain length) that retained carboxyfluorescein, a lipid formulation consisting of DPSB/Cholesterol/PEG-DSPE at a molar ratio of 85/10/5 were prepared and liposomes were made as described above in a self-quenched 100 mM carboxyfluorescein-10 mM Tris/HCl pH 7.4-150 mM KBr solution and dialyzed against a solution of 150 mM Kbr-110 mM NaCl 110 mM hepes buffer pH 7.4 isotonic with the self-quenched carboxyfluorescein solution to remove unencapsulated carboxyfluorescein. This created a condition where there was KBr on the inside and sodium chloride on the outside. An aliquot of this liposome suspension was diluted into a 50% bovine serum solution in 140 mM sodium chloride-10 mM hepes buffer pH 7.4 (release buffer) at 37 C or into the release buffer at 43 C and the leakage of the self-quenched carboxyfluorescein from the liposome was followed by measuring the change in fluorescence (Ex. 485 Em. 520) as a function of time after addition of the liposomes. The leakage kinetics are shown in FIG. 35.

Upon diluting the liposome sample into the 37 C buffer system, there was approximately 10% of the contents released by 20 seconds after dilution. Diluting an aliquot of the liposomes into the 43 C buffer released approximately 40% of the contents 20 seconds after dilution. This temperature dependent release can be used to deliver liposome encapsulated drugs from liposomes prepared from the DPSB lipid with other lipids such as DPPC. Alternatively the temperature sensitive release system can be created from the DMSB lipid by preparing the liposome in the KBr buffer and replacing the KBr buffer with an NaCL buffer in a similar process as that described to form the DPSB liposome.

The thermal sensitive liposome can also be produced from liposomes composed of the sulfobetaine lipids with one salt type encapsulated in the liposome and a second salt type on the outside. For instance, the liposomes can be prepared in a buffer containing 150 mM sodium bromide and completely replacing the sodium bromide on the outside with 150 mM sodium chloride. This asymmetry of salt type creates conditions where when the liposomes are placed in a fluid that promotes the upper transition temperature, at a temperature that is below the lower transition temperature, the liposomes are poised to change their properties when the temperature is raised above the lower transition temperature. This change in organization that occurs at the low transition temperature leads to release of encapsulated contents as the lipids rearrange from a solid state into a fluid state.

Other inverse lipids with saturated acyl chains such as the dimyristoylbetaine (example 5) when mixed with normal phosphatidylcholine lipids (PC) with saturated acyl lipids such as dimyristoylPC or phosphatidylethanolamine (PE) lipids with saturated chains such as dimyristoylPE could also be used to prepare liposome for rapid contents release when the temperature is increased from 37 C to preferably between 41 C-45 C.

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in the entirety.

What is claimed is:

1. A zwitterionic lipid having the formula:

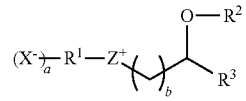

wherein $X^-$ is a member selected from:

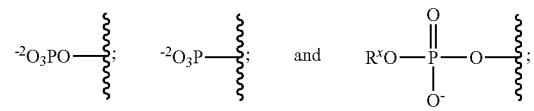

wherein $R^x$ is selected from H and substituted or unsubstituted alkyl;

a is selected from the integers from 1 to 6;

b is selected from the integers from 0 to 18;

$R^I$ is a member selected from substituted alkyl, substituted or unsubstituted heteroalkyl, substituted aryl, and substituted heteroaryl, wherein $R^I$ includes the moiety;

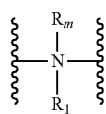

in which
R$^l$ and R$^m$ are independently selected from H and alkyl;
Z$^+$ is:

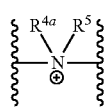

wherein
R$^4$ and R$^5$ are members independently selected from H, substituted or unsubstituted alkyl; and
R$^2$ and R$^3$ are members independently selected from H, and substituted or unsubstituted alkyl,
with the proviso that at least one of R$^2$ and R$^3$ is other than H.

2. The zwitterionic lipid according to claim 1, wherein a member selected from R$^2$ and R$^3$ is unbranched and the other member is branched.

3. The zwitterionic lipid according to claim 2, wherein said unbranched chain comprises a subunit which is terminated with a functional group, said subunit being a member selected from a C$_6$-C$_{12}$ fluorocarbyl and a C$_6$-C$_{18}$ hydrocarbyl moiety.

4. The zwitterionic lipid according to claim 3, wherein said functional group is a member selected from hydroxyl, amine, carboxylic acid, aldehyde, carboxylic acid ester, and thiol.

5. The zwitterionic lipid according to claim 1, wherein a member selected from R$^2$, R$^3$ and a combination thereof comprises a guanadinyl moiety.

6. The zwitterionic lipid according to claim 1, wherein a member selected from R$^2$, R$^3$ and a combination thereof comprises a thioether moiety.

7. The zwitterionic lipid according to claim 1, having the formula:

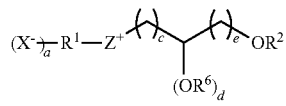

wherein
c and e are independently selected from the integers from 1 to 18;
d is selected from the integers 0 and 1;
R$^6$ is a member selected from selected from substituted or unsubstituted alkyl.

8. The zwitterionic lipid according to claim 1, wherein a member selected from R$^4$, R$^5$ and a combination thereof is H.

9. The zwitterionic lipid according to claim 1, said lipid having a pKa of greater than 5.

10. The zwitterionic lipid according to claim 1, said lipid having a pKa of from about 6 to about 7.

11. A pharmaceutical formulation comprising a zwitterionic lipid according to claim 1 and a pharmaceutically acceptable carrier.

12. The pharmaceutical formulation according to claim 11, further comprising a bioactive compound.

13. An encapsulator particle selected from the group consisting of liposomes, emulsions, micelles and lipidic bodies, wherein the encapsulator particle comprises the zwitterionic lipid according to claim 1.

14. The encapsulator particle of claim 13 further comprising a bioactive agent encapsulated in said particle.

15. A zwitterionic lipid having the formula:

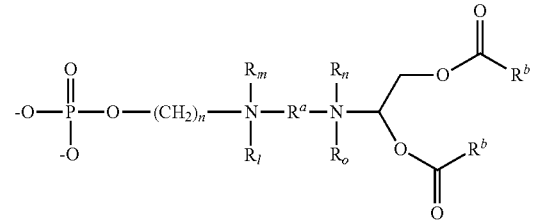

in which
R$^a$ is an alkylene linker moiety;
R$^l$, R$^m$, R$^n$ and R$^o$ are independently selected from H and alkyl;
each R$^b$ is independently selected from substituted or unsubstituted alkyl an substituted or unsubstituted heteroalkyl; and
n is 2.

16. The zwitterionic lipid of claim 15, wherein each R$^b$ is a linoleoyl.

17. The zwitterionic lipid of claim 15, wherein each of R$^l$, R$^m$, R$^n$ and R$^o$ is methyl.

\* \* \* \* \*